US010650312B2

(12) United States Patent
Roquet et al.

(10) Patent No.: US 10,650,312 B2
(45) Date of Patent: May 12, 2020

(54) NUCLEIC ACID-BASED DATA STORAGE

(71) Applicant: Catalog Technologies, Inc., Boston, MA (US)

(72) Inventors: Nathaniel Roquet, San Francisco, CA (US); Hyunjun Park, Cambridge, MA (US); Swapnil P. Bhatia, Boston, MA (US)

(73) Assignee: CATALOG TECHNOLOGIES, INC., Boston, MA (US)

( * ) Notice: Subject to any disclaimer, the term of this patent is extended or adjusted under 35 U.S.C. 154(b) by 0 days.

(21) Appl. No.: 15/850,112

(22) Filed: Dec. 21, 2017

(65) Prior Publication Data
US 2018/0137418 A1   May 17, 2018

Related U.S. Application Data

(63) Continuation of application No. PCT/US2017/062098, filed on Nov. 16, 2017.

(60) Provisional application No. 62/466,304, filed on Mar. 2, 2017, provisional application No. 62/457,074, filed on Feb. 9, 2017, provisional application No. 62/423,058, filed on Nov. 16, 2016.

(51) Int. Cl.
G06N 3/12       (2006.01)
C12N 9/22       (2006.01)
G06F 5/08       (2006.01)
G16B 20/00      (2019.01)

(52) U.S. Cl.
CPC ............... *G06N 3/123* (2013.01); *C12N 9/22* (2013.01); *G06F 5/08* (2013.01); *C12N 2310/20* (2017.05); *G16B 20/00* (2019.02)

(58) Field of Classification Search
CPC ...... G06N 3/123; C12N 2310/20; C12N 9/22; C07K 2319/80; C07K 2319/81
See application file for complete search history.

(56) References Cited

U.S. PATENT DOCUMENTS

| | | | |
|---|---|---|---|
| 6,187,537 B1 | 2/2001 | Zinn, Jr. et al. | |
| 6,221,653 B1 | 4/2001 | Caren et al. | |
| 6,309,828 B1 | 10/2001 | Schleifer et al. | |
| 6,384,210 B1 | 5/2002 | Blanchard | |
| 6,419,883 B1 | 7/2002 | Blanchard | |
| 6,446,642 B1 | 9/2002 | Caren et al. | |
| 6,458,583 B1 | 10/2002 | Bruhn et al. | |
| 6,537,747 B1 | 3/2003 | Mills, Jr. et al. | |
| 6,796,634 B2 | 9/2004 | Caren et al. | |
| 7,176,297 B2 | 2/2007 | Li et al. | |
| 7,306,316 B2 | 12/2007 | Doak | |
| 7,491,422 B2 | 2/2009 | Zhang et al. | |
| 7,600,840 B2 | 10/2009 | Kim et al. | |
| 7,802,517 B2 | 9/2010 | Wessels et al. | |
| 7,833,701 B2 | 11/2010 | Oshima | |
| 7,909,427 B2 | 3/2011 | Kim et al. | |
| 7,951,334 B2 | 5/2011 | Mirkin et al. | |
| 8,071,168 B2 | 12/2011 | Cruchon-Dupeyrat et al. | |
| 8,114,207 B2 | 2/2012 | Josten | |
| 8,136,936 B2 | 3/2012 | Hook et al. | |
| 8,496,326 B2 | 7/2013 | Hook et al. | |
| 8,769,689 B2 | 7/2014 | Hoglund | |
| 8,806,127 B2 | 8/2014 | Brownell et al. | |
| 8,856,940 B2 | 10/2014 | Kencl et al. | |
| 9,061,494 B2 | 6/2015 | Rogers et al. | |
| 9,062,218 B2 | 6/2015 | Oshima et al. | |
| 9,187,777 B2 | 11/2015 | Jacobson et al. | |
| 9,266,370 B2 | 2/2016 | Jung et al. | |
| 9,403,180 B2 | 8/2016 | Ha et al. | |
| 9,487,002 B2 | 11/2016 | Rogers et al. | |
| 9,616,661 B2 | 4/2017 | Pierik et al. | |
| 9,904,734 B2 | 2/2018 | Murrah et al. | |
| 10,027,347 B2 | 7/2018 | Le Scouarnec et al. | |
| 10,047,235 B2 | 8/2018 | Wilsher et al. | |
| 10,050,959 B2 | 8/2018 | Soon-Shiong et al. | |
| 2003/0116630 A1 | 6/2003 | Carey et al. | |
| 2004/0244623 A1 | 12/2004 | Hayashizaki | |
| 2005/0019760 A1 | 1/2005 | Southern | |
| 2005/0166782 A2 | 8/2005 | Hayashizaki | |
| 2005/0243618 A1* | 11/2005 | Boland .................. B82Y 10/00 365/201 |
| 2006/0263534 A1 | 11/2006 | Laurent et al. | |
| 2008/0252679 A1 | 10/2008 | Pierik et al. | |
| 2008/0269152 A1 | 10/2008 | Verdine et al. | |
| 2008/0303870 A1 | 12/2008 | Verbeek et al. | |
| 2008/0309701 A1 | 12/2008 | Pierik et al. | |
| 2009/0023607 A1 | 1/2009 | Rozhok et al. | |
| 2009/0033690 A1 | 2/2009 | Pierik et al. | |
| 2009/0253141 A1 | 10/2009 | Quake | |

(Continued)

FOREIGN PATENT DOCUMENTS

EP  1512749        3/2005
EP  2329425 B1    7/2013

(Continued)

OTHER PUBLICATIONS

Sands, B. and Brent, R. Jan. 4, 2016. Overview of post Cohen-Boyer methods for single segment cloning and for multisegment DNA assembly. Current Protocols in Molecular Biology, vol. 113, pp. 3.26.1-3.26-20. (Year: 2016).*

(Continued)

*Primary Examiner* — Jennifer Dunston
(74) *Attorney, Agent, or Firm* — White & Case LLP

(57) ABSTRACT

Methods and systems for encoding digital information in nucleic acid (e.g., deoxyribonucleic acid) molecules without base-by-base synthesis, by encoding bit-value information in the presence or absence of unique nucleic acid sequences within a pool, comprising specifying each bit location in a bit-stream with a unique nucleic sequence and specifying the bit value at that location by the presence or absence of the corresponding unique nucleic acid sequence in the pool But, more generally, specifying unique bytes in a bytestream by unique subsets of nucleic acid sequences. Also disclosed are methods for generating unique nucleic acid sequences without base-by-base synthesis using combinatorial genomic strategies (e.g., assembly of multiple nucleic acid sequences or enzymatic-based editing of nucleic acid sequences).

26 Claims, 32 Drawing Sheets

(56) References Cited

U.S. PATENT DOCUMENTS

| | | |
|---|---|---|
| 2010/0029490 A1 | 2/2010 | Pierik et al. |
| 2010/0056381 A1 | 3/2010 | Kurt et al. |
| 2011/0195850 A1 | 8/2011 | Rozhok et al. |
| 2011/0312779 A1 | 12/2011 | Silverbrook et al. |
| 2011/0312782 A1 | 12/2011 | Azimi et al. |
| 2011/0312847 A1 | 12/2011 | Silverbrook et al. |
| 2011/0312851 A1 | 12/2011 | Silverbrook et al. |
| 2011/0312853 A1 | 12/2011 | Azimi et al. |
| 2011/0312855 A1 | 12/2011 | Silverbrook et al. |
| 2011/0312856 A1 | 12/2011 | Silverbrook et al. |
| 2012/0164396 A1 | 6/2012 | Mirkin et al. |
| 2012/0329561 A1 | 12/2012 | Evans et al. |
| 2013/0231254 A1 | 9/2013 | Kawashima et al. |
| 2014/0296087 A1 | 10/2014 | Verdine et al. |
| 2014/0371100 A1 | 12/2014 | Kawashima et al. |
| 2015/0261664 A1 | 9/2015 | Goldman et al. |
| 2015/0269313 A1 | 9/2015 | Church |
| 2015/0312212 A1 | 10/2015 | Holmes et al. |
| 2016/0007893 A1 | 1/2016 | Roberts |
| 2016/0051985 A1 | 2/2016 | Knight et al. |
| 2016/0168579 A1 | 6/2016 | Hutchison et al. |
| 2016/0371434 A1* | 12/2016 | Strauss .................. G06F 19/28 |
| 2017/0017436 A1 | 1/2017 | Church |
| 2017/0081716 A1 | 3/2017 | Peck |
| 2017/0093851 A1 | 3/2017 | Allen |
| 2017/0136452 A1 | 5/2017 | Niles et al. |
| 2017/0140095 A1 | 5/2017 | Kim |
| 2017/0218228 A1 | 8/2017 | Jose et al. |
| 2017/0363953 A1 | 12/2017 | Steinhart et al. |
| 2018/0068060 A1 | 3/2018 | Ceze et al. |
| 2018/0086781 A1 | 3/2018 | Liss |
| 2018/0101487 A1 | 4/2018 | Peck |
| 2018/0121478 A1 | 5/2018 | Walder et al. |
| 2018/0253563 A1 | 9/2018 | Peck et al. |
| 2019/0020651 A1 | 1/2019 | Soon-Shiong et al. |

FOREIGN PATENT DOCUMENTS

| | | |
|---|---|---|
| EP | 2856375 B1 | 7/2018 |
| EP | 3346404 A1 | 7/2018 |
| WO | WO-03025123 A2 | 3/2003 |
| WO | WO-2014014991 | 1/2014 |
| WO | WO-2015144858 A1 | 10/2015 |
| WO | WO-2016015701 A1 | 2/2016 |
| WO | WO-2016059610 | 4/2016 |
| WO | WO-2016081834 A3 | 8/2016 |
| WO | WO-2016164779 A1 | 10/2016 |
| WO | WO-2016182814 A2 | 11/2016 |
| WO | WO-2017151195 A1 | 9/2017 |
| WO | WO-2017190297 A1 | 11/2017 |
| WO | WO-2018017131 A1 | 1/2018 |
| WO | WO-2018049272 A1 | 3/2018 |
| WO | WO-2018094108 A1 | 5/2018 |
| WO | WO-2018148260 A1 | 8/2018 |
| WO | WO-2018148458 A1 | 8/2018 |
| WO | WO-2018213856 A2 | 11/2018 |

OTHER PUBLICATIONS

Yang et al. Permanent genetic memory with >1-byte capacity. Nature Methods, vol. 11, No. 12, pp. 1261-1266, Oct. 26, 2014, including pp. 1/3-3/3 of Online Methods, and pp. 1/30-30/30 of Supplementary Figures and Text. (Year: 2014).*

Fogg et al. New applications for phage integrases. Journal of Molecular Biology, vol. 426, No. 15, pp. 2703-2716, May 2014. (Year: 2014).*

Yazdi et al. A rewritable, random-access DNA-based storage system. Scientific Reports, vol. 5, 14138, Sep. 18, 2015, printed as pp. 1/10-10/10, including pp. 1/19-19/19 of Supplementary Information. (Year: 2015).*

Sun et al. Recent advances in targeted genome engineering in mammalian systems. Biotechnology Journal, vol. 7, pp. 1074-1087, 2012. (Year: 2012).*

Quetier et al. The CRISPR-Cas9 technology: Closer to the ultimate toolkit for targeted genome editing. Plant Science, vol. 242, pp. 65-76, Sep. 8, 2015. (Year: 2015).*

Sorek et al. CRISPR-Mediated Adaptive Immune Systems in Bacteria and Archaea. Annual Review of Biochemistry, vol. 82, pp. 237-266, Mar. 11, 2013. (Year: 2013).*

Bonnet et al. Rewritable digital data storage in live cells via engineered control of recombination directionality. Proceeding of the National Academy of Sciences, USA, vol. 109, No. 23, pp. 8884-8889, Jun. 2012. (Year: 2012).*

Yim et al. The essential component in DNA-based information storage system: robust error-tolerating module. Frontiers in Bioengineering and Biotechnology, vol. 2, Article 49, Nov. 6, 2014, printed as pp. 1/5-5/5. (Year: 2014).*

Engler et al. A one pot, one step, precision cloning method with high-throughput capability. PLoS ONE, vol. 3, No. 11, E3647, Nov. 5, 2008, printed as pp. 1/7-7/7. (Year: 2008).*

Kivioja et al. Counting absolute Nos. Of molecules using unique molecular identifiers. Nature Methods, vol. 9, No. 1, pp. 72-74, Nov. 20, 2011, including pp. 1/2-2/2 of Online Methods, and pp. 1/14-14/-14 of Supplementary Information. (Year: 2011).*

Leier et al. Cryptography with DNA binary strands. BioSystems, vol. 57, pp. 13-22, 2000. (Year: 2000).*

Engler et al. Chapter 12: Combinatorial DNA assembly using Golden Gate cloning. Karen M. Polizzi and Cleo Kontoravadi (eds.), Synthetic Biology, Methods in Molecular Biology, vol. 1073, Springer Science+Business Media, New York, 2013, pp. 141-156. (Year: 2013).*

Deorowicz, et al. Data compression for sequencing data, Deorowicz and Grabowski Algorithms for Molecular Biology, 2013, 8:25, 13 pages.

Goldman, et al. Towards practical, high-capacity, low-maintenance information storage in synthesized DNA, Nature, Feb. 7, 2013, 494:77-80.

Roquet, et al. Synthetic recombinase-based state machines in living cells, Science, Jul. 22, 2016, vol. 353, Issue 6297 and 8559.

Zhu, et al. High-throughput DNA sequence data compression, Briefings in Bioinformatics, Jan. 1, 2015, 16(1):1-15.

Bornholt et al., A DNA-Based Archival Storage System, in International Conference on Architectural Support for Programming Languages and Operating Systems (ASPLOS), Apr. 2-6, 2016, Atlanta, GA, 2016, 637-649.

PCT/US2017/062098 International Search Report and Written Opinion dated Mar. 14, 2018.

Yazdi, S. M. Hossein Tabatabaei et al., 'DNA-based storage: trends and methods', IEEE Transactions on Molecular, Biological, and Multi-Scale Communications, Sep. 2015, vol. 1, No. 3, pp. 230-248.

Bystrykh, et al., "Generalized DNA Barcode Design Based on Hamming Codes", PLOS One, vol. 7, No. 5, pp. 1-8, (May 2012).

Buschmann, et al., "Levenshtein Error-Correcting Barcodes for Multiplexed DNA Sequencing", BMC Bioinformatics, vol. 14, No. 1., pp. 1-10 (2013).

Casini, A. "Advanced DNA assembly strategies and standards for synthetic biology," Thesis, Department of Life Sciences, Imperial College London: 1-178 (2014).

PCT/US2017/062106 International Search Report and Written Opinion dated Feb. 22, 2018.

PCT/US2019/022596 International Search Report and Written Opinion dated Jun. 28, 2019.

PCT/US2019/032756 International Search Report and Written Opinion dated Sep. 4, 2019.

Tulpan, et al., "HyDEn: A Hybrid Steganocryptographic Approach for Data Encryption Using Randomized Error Correcting DNA Codes,", Biomed Research International, vol. 32, No. 4839, pp. 1-11, (2013).

* cited by examiner $C_{xy}$ is the yth component in layer x. For a starting library with M layers, each with N components, the identifiers would have the following architecture:

where a, b, c represent elements in the set {1, 2, ..., N}

$C_{xy}$ is the yth component in layer x. For a starting library with M layers, each with N components, the identifiers would have the following architecture:

where *b, e, h* are elements in the set {1, 2, ..., N}, and *a, d, f* are unique elements in the set {1, 2, ..., M}.

The combinatorial space of possible identifiers is $N^M M!$ $C_{xy}$ is the yth component in layer x. For a starting library with M layers, each with N components, Identifiers assemble a fixed number of components, k, and have the following architecture:

where b, e, h are elements in the set {1, 2, ..., N}, and a, d, f among k unique, rank-ordered elements in the set {1, 2, ..., M}.

The combinatorial space of possible identifiers is $N^k M choose k$

NUCLEIC ACID-BASED DATA STORAGE

CROSS-REFERENCE

This application is a Continuation Application of International Patent Application No. PCT/US17/062098 filed Nov. 16, 2017, which claims the benefit of U.S. Provisional Patent Application Ser. No. 62/423,058, filed Nov. 16, 2016, U.S. Provisional Patent Application Ser. No. 62/457,074, filed Feb. 9, 2017, and U.S. Provisional Patent Application Ser. No. 62/466,304, filed Mar. 2, 2017, each of which is entirely incorporated herein by reference.

BACKGROUND

Nucleic acid digital data storage is a stable approach for encoding and storing information for long periods of time, with data stored at higher densities than magnetic tape or hard drive storage systems. Additionally, digital data stored in nucleic acid molecules that are stored in cold and dry conditions can be retrieved as long as 60,000 years later or longer.

To access digital data stored in nucleic acid molecules, the nucleic acid molecules may be sequenced. As such, nucleic acid digital data storage may be an ideal method for storing data that is not frequently accessed but may have a high volume of information to be stored or archived for long periods of time.

Current methods rely on encoding the digital information (e.g., binary code) into base-by-base nucleic acids sequences, such that the base to base relationship in the sequence directly translates into the digital information (e.g., binary code). Sequencing of digital data stored in base-by-base sequences that can be read into bit-streams or bytes of digitally encoded information can be error prone and costly to encode since the cost of de novo base-by-base nucleic acid synthesis can be expensive. Opportunities for new methods of performing nucleic acid digital data storage may provide approaches for encoding and retrieving data that are less costly and easier to commercially implement.

SUMMARY

Methods and systems for encoding digital information in nucleic acid (e.g., deoxyribonucleic acid, DNA) molecules without base-by-base synthesis, by encoding bit-value information in the presence or absence of unique nucleic acid sequences within a pool, comprising specifying each bit location in a bit-stream with a unique nucleic sequence and specifying the bit value at that location by the presence or absence of the corresponding unique nucleic acid sequence in the pool. But, more generally, specifying unique bytes in a byte stream by unique subsets of nucleic acid sequences. Also disclosed are methods for generating unique nucleic acid sequences without base-to-base synthesis using combinatorial genomic strategies (e.g., assembly of multiple nucleic acid sequences or enzymatic-based editing of nucleic acid sequences).

In an aspect, the present disclosure provides a method for writing information into nucleic acid sequence(s), comprising: (a) translating the information into a string of symbols; (b) mapping the string of symbols to a plurality of identifiers, wherein an individual identifier of the plurality of identifiers comprises one or more components, wherein an individual component of the one or more components comprises a nucleic acid sequence, and wherein the individual identifier of the plurality of identifiers corresponds to an individual symbol of the string of symbols; and (c) constructing an identifier library comprising at least a subset of the plurality of identifiers.

In some embodiments, each symbol in the string of symbols is one of two possible symbol values. In some embodiments, one symbol value at each position of the string of symbols may be represented by the absence of a distinct identifier in the identifier library. In some embodiments, the two possible symbol values are a bit-value of 0 and 1, wherein the individual symbol with the bit-value of 0 in the string of symbols may be represented by an absence of a distinct identifier in the identifier library, wherein the individual symbol with the bit-value of 1 in the string of symbols may be represented by a presence of the distinct identifier in the identifier library, and vice versa. In some embodiments, each symbol of the string of symbols is one of one or more possible symbol values. In some embodiments, a presence of an individual identifier in the identifier library corresponds to a first symbol value in a binary string and an absence of the individual identifier corresponds to a second symbol value in a binary string. In some embodiments, the first symbol value is a bit value of 1 and the second symbol value is a bit value of 0. In some embodiments, the first symbol value is a bit value of 0 and the second symbol value is a bit value of 1.

In some embodiments, constructing the individual identifier in the identifier library comprises assembling the one or more components from one or more layers and wherein each layer of the one or more layers comprises a distinct set of components. In some embodiments, the individual identifier from the identifier library comprises one component from each layer of the one or more layers. In some embodiments, the one or more components are assembled in a fixed order. In some embodiments, the one or more components are assembled in a random order. In some embodiments, the one or more components are assembled with one or more partitioning components disposed between two components from different layers of the one or more layers. In some embodiments, the individual identifier comprises one component from each layer of a subset of the one or more layers. In some embodiments, the individual identifier comprises at least one component from each of the one or more layers. In some embodiments, the one or more components are assembled using overlap-extension polymerase chain reaction (PCR), polymerase cycling assembly, sticky end ligation, biobricks assembly, golden gate assembly, gibson assembly, recombinase assembly, ligase cycling reaction, or template directed ligation.

In some embodiments, constructing the individual identifier in the identifier library comprises deleting, replacing, or inserting at least one component in a parent identifier by applying nucleic acid editing enzymes to the parent identifier. In some embodiments, the parent identifier comprises a plurality of components flanked by nuclease-specific target sites, recombinase recognition sites, or distinct spacer sequences. In some embodiments, the nucleic acid editing enzymes are selected from the group consisting of CRISPR-Cas, TALENs, Zinc Finger Nucleases, Recombinases, and functional variants thereof.

In some embodiments, the identifier library comprises a plurality of nucleic acid sequences. In some embodiments, the plurality of nucleic acid sequences stores metadata of the information and/or conceals the information. In some embodiments, the metadata comprises secondary information corresponding to a source of the information, an intended recipient of the information, an original format of the information, instrumentation and methods used to encode the information, a date and a time of writing the information into the identifier library, modifications made to the information, and/or a reference to other information.

In some embodiments, one or more identifier libraries are combined and wherein each identifier library of the one or more identifier libraries is tagged with a distinct barcode. In some embodiments, each individual identifier in the identifier library comprises the distinct barcode. In some embodiments, the plurality of identifiers is selected for ease of read, write, access, copy, and deletion operations. In some embodiments, the plurality of identifiers is selected to minimize write errors, mutations, degradation, and read errors.

In another aspect, the present disclosure provides a method for copying information encoded in nucleic acid sequence(s), comprising: (a) providing an identifier library encoding a string of symbols, wherein the identifier library comprises a plurality of identifiers, wherein an individual identifier of the plurality of identifiers comprises one or more components, wherein an individual component of the one or more components comprises a nucleic acid sequence, and wherein the individual identifier of the plurality of identifiers corresponds to an individual symbol of the string of symbols; and (b) constructing one or more copies of the identifier library.

In some embodiments, the plurality of identifiers comprises one or more primer binding sites. In some embodiments, the identifier library is copied using polymerase chain reaction (PCR). In some embodiments, the PCR is conventional PCR or linear PCR and wherein a number of copies of the identifier library double or increase linearly, respectively, with each PCR cycle. In some embodiments, the individual identifier in the identifier library is ligated into a circular vector prior to PCR and wherein the circle vector comprises a barcode at each end of the individual identifier.

In some embodiments, the identifier library comprises a plurality of nucleic acid sequences. In some embodiments, the plurality of nucleic acid sequences is copied. In some embodiments, one or more identifier libraries are combined prior to copying and wherein each library of the one or more identifier libraries comprises a distinct barcode.

In another aspect, the present disclosure provides a method for accessing information encoded in nucleic acid sequence(s), comprising: (a) providing an identifier library encoding a string of symbols, wherein the identifier library comprises a plurality of identifiers, wherein an individual identifier of the plurality of identifiers comprises one or more components, wherein an individual component of the one or more components comprises a nucleic acid sequence, and wherein the individual identifier of the plurality of identifiers corresponds to an individual symbol of the string of symbols; and (b) extracting a targeted subset of the plurality of identifiers from the identifier library.

In some embodiments, a plurality of probes is combined with the identifier library. In some embodiments, the plurality of probes share complementarity with the targeted subset of the plurality of identifiers from the identifier library. In some embodiments, the plurality of probes hybridizes the targeted subset of the plurality of identifiers in the identifier library. In some embodiments, the plurality of probes comprises one or more affinity tags and wherein the one or more affinity tags is captured by an affinity bead or an affinity column.

In some embodiments, the identifier library is sequentially combined with one or more subsets of the plurality of probes and wherein a portion of the identifier library binds to the one or more subsets of the plurality of probes. In some embodiments, the portion of the identifier library that binds to the one or more subsets of the plurality of probes is removed prior to the addition of another subset of the plurality of probes to the identifier library.

In some embodiments, the individual identifier of the plurality of identifiers comprises one or more common primer binding regions, one or more variable primer binding regions, or any combination thereof. In some embodiments, the identifier library is combined with primers that bind to the one or more common primer binding regions or to the one or more variable primer binding regions. In some embodiments, the primers that bind to the one or more variable primer binding regions are used to selectively amplify the targeted subset of the identifier library.

In some embodiments, a portion of identifiers is removed from the identifier library by selective nuclease cleavage. In some embodiments, the identifier library is combined with Cas9 and guide probes and wherein the guide probes guide the Cas9 to remove specified identifiers from the identifier library. In some embodiments, the individual identifiers are single-stranded and wherein the identifier library is combined with a single-strand specific endonuclease(s). In some embodiments, the identifier library is mixed with a complementary set of individual identifiers that protect target individual identifiers from degradation prior to the addition of the single-strand specific endonuclease(s). In some embodiments, the individual identifiers that are not cleaved by the selective nuclease cleavage are separated by size-selective chromatography. In some embodiments, the individual identifiers that are not cleaved by the selective nuclease cleavage are amplified and wherein the individual identifiers that are cleaved by the selective nuclease cleavage are not amplified. In some embodiments, the identifier library comprises a plurality of nucleic acid sequences and wherein the plurality of nucleic acid sequences are extracted with the targeted subset of the plurality of identifiers in the identifier library.

In another aspect, the present disclosure provides a method for reading information encoded in nucleic acid sequence(s), comprising: (a) providing an identifier library comprising a plurality of identifiers, wherein an individual identifier of the plurality of identifiers comprises one or more components, wherein an individual component of the one or more components comprises a nucleic acid sequence; (b) identifying the plurality of identifiers in the identifier library; (c) generating a plurality of symbols from the plurality of identifiers identified in (b), wherein an individual symbol of the plurality of symbols corresponds to the individual identifier of the plurality of identifiers; and (d) compiling the information from the plurality of symbols.

In some embodiments, each symbol in the string of symbols is one of two possible symbol values. In some embodiments, one symbol value at each position of the string of symbols may be represented by the absence of a distinct identifier in the identifier library. In some embodiments, the two possible symbol values are a bit-value of 0 and 1, wherein the individual symbol with the bit-value of 0 in the string of symbols may be represented by an absence of a distinct identifier in the identifier library, wherein the individual symbol with the bit-value of 1 in the string of symbols may be represented by a presence of the distinct identifier in the identifier library, and vice versa. In some embodiments, a presence of an individual identifier in the identifier library corresponds to a first symbol value in a binary string and an absence of the individual identifier in the identifier library corresponds to a second symbol value in a binary string. In some embodiments, the first symbol value is a bit value of 1 and the second symbol value is a bit value of 0. In some embodiments, the first symbol value is a bit value of 0 and the second symbol value is a bit value of 1.

In some embodiments, identifying the plurality of identifiers comprises sequencing the plurality of identifiers in the identifier library. In some embodiments, sequencing comprises digital polymerase chain reaction (PCR), quantitative PCR, a microarray, sequencing by synthesis, or massively-parallel sequencing. In some embodiments, the identifier library comprises a plurality of nucleic acid sequences. In some embodiments, the plurality of nucleic acid sequences store metadata of the information and/or conceal the information. In some embodiments, one or more identifier libraries are combined and wherein each identifier library in the one or more identifier libraries comprises a distinct barcode. In some embodiments, the barcode stores metadata of the information.

In another aspect, the present disclosure provides a method for nucleic acid-based computer data storage, comprising: (a) receiving computer data, (b) synthesizing nucleic acid molecules comprising nucleic acid sequences encoding the computer data, wherein the computer data is encoded in at least a subset of nucleic acid molecules synthesized and not in a sequence of each of the nucleic acid molecules, and (c) storing the nucleic acid molecules having the nucleic acid sequences.

In some embodiments, the at least the subset of the nucleic acid molecules are grouped together. In some embodiments, the method further comprises sequencing the nucleic acid molecule(s) to determine the nucleic acid sequence(s), thereby retrieving the computer data. In some embodiments, (b) is performed in a time period that is less than about 1 day. In some embodiments, (b) is performed at an accuracy of at least about 90%.

In another aspect, the present disclosure provides a method for nucleic acid-based computer data storage, comprising: (a) receiving computer data, (b) synthesizing a nucleic acid molecule comprising at least one nucleic acid sequence encoding the computer data, which synthesizing the nucleic acid molecule is in the absence of base-by-base nucleic acid synthesis, and (c) storing the nucleic acid molecule comprising the at least one nucleic acid sequence.

In some embodiments, the method further comprises sequencing the nucleic acid molecule to determine the nucleic acid sequence, thereby retrieving the computer data. In some embodiments, (b) is performed in a time period that is less than about 1 day. In some embodiments, (b) is performed at an accuracy of at least about 90%.

In another aspect, the present disclosure provides a system for encoding binary sequence data using nucleic acids, comprising: a device configured to construct an identifier library, wherein the identifier library comprises a plurality of identifiers, wherein an individual identifier of the plurality of identifiers comprises one or more components, and wherein an individual component of the one or more components is a nucleic acid sequence; and one or more computer processors operatively coupled to the device, wherein the one or more computer processors are individually or collectively programmed to (i) translate the information into a string of symbols, (ii) map the string of symbols to the plurality of identifiers, wherein the individual identifier of the plurality of identifiers corresponds to an individual symbol of the string of symbols, and (iii) construct an identifier library comprising the plurality of identifiers.

In some embodiments, the device comprises a plurality of partitions and wherein the identifier library is generated in one or more of the plurality of partitions. In some embodiments, the plurality of partitions comprises wells. In some embodiments, constructing the individual identifier in the identifier library comprises assembling the one or more components from one or more layers and wherein each layer of the one or more layers comprises a distinct set of components. In some embodiments, each layer of the one or more layers is stored in a separate portion of the device and wherein the device is configured to combine the one or more components from the one or more layers. In some embodiments, the identifier library comprises a plurality of nucleic acid sequences. In some embodiments, one or more identifier libraries are combined in a single area of the device and wherein each identifier library of the one or more identifier libraries comprises a distinct barcode.

In another aspect, the present disclosure provides a system for reading information encoded in nucleic acid sequence(s), comprising: a database that stores an identifier library comprising a plurality of identifiers, wherein an individual identifier of the plurality of identifiers comprises one or more components, wherein an individual component of the one or more components comprises a nucleic acid sequence; and one or more computer processors operatively coupled to the database, wherein the one or more computer processors are individually or collectively programmed to (i) identify the plurality of identifiers in the identifier library, (ii) generate a plurality of symbols from the plurality of identifiers identified in (i), wherein an individual symbol of the plurality of symbols corresponds to the individual identifier of the plurality of identifiers, and (iii) compile the information from the plurality of symbols.

In some embodiments, the system further comprises a plurality of partitions. In some embodiments, the partitions are wells. In some embodiments, a given partition of the plurality of partitions comprises one or more identifier libraries and wherein each identifier library of the one or more identifier libraries comprises a distinct barcode. In some embodiments, the system further comprises a detection unit configured to identify the plurality of identifiers in the identifier library.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 2A illustrates combining a rank object (or address object) with a byte-value object (or data object) to create an identifier; FIG. 2B illustrates an embodiment of the data at address method wherein the rank objects and byte-value objects are themselves combinatorial concatenations of other objects;

FIG. 3A illustrates encoding digital information using a rank object as an identifier; FIG. 3B illustrates an embodiment of the encoding method wherein the address objects are themselves combinatorial concatenations of other objects;

FIG. 6A illustrates the architecture of identifiers constructed using the product scheme; FIG. 6B illustrates an example of the combinatorial space of identifiers that may be constructed using the product scheme;

FIG. 10A schematically illustrates the use of template directed ligation to construct identifiers (e.g., nucleic acid molecules) from components (e.g., nucleic acid sequences); FIG. 10B shows a histogram of the copy numbers (abundances) of 256 distinct nucleic acid sequences that were each combinatorially assembled from six nucleic acid sequences (e.g., components) in one pooled template directed ligation reaction;

FIG. 11A illustrates the architecture of identifiers constructed using the permutation scheme; FIG. 11B illustrates an example of the combinatorial space of identifiers that may be constructed using the permutation scheme; FIG. 11C shows an example implementation of the permutation scheme with template directed ligation; FIG. 11D shows an example of how the implementation from FIG. 11C may be modified to construct identifiers with permuted and repeated components; FIG. 11E shows how the example implementation from FIG. 11D may lead to unwanted byproducts that may be removed with nucleic acid size selection; FIG. 11F shows another example of how to use template directed ligation and size selection to construct identifiers with permuted and repeated components; FIG. 11G shows an example of when size selection may fail to isolate a particular identifier from unwanted byproducts;

FIG. 12A illustrates the architecture of identifiers constructed using the MchooseK scheme; FIG. 12B illustrates an example of the combinatorial space of identifiers that may be constructed using the MchooseK scheme; FIG. 12C shows an example implementation of the MchooseK scheme using template directed ligation; FIG. 12D shows how the example implementation from FIG. 12C may lead to unwanted byproducts that may be removed with nucleic acid size selection;

FIG. 13A shows an example of the combinatorial space of identifiers that may be constructed using the partition scheme; FIG. 13B shows an example implementation of the partition scheme using template directed ligation;

FIG. 14A shows an example of the combinatorial space of identifiers that may be constructed using the USS scheme; FIG. 14B shows an example implementation of the USS scheme using template directed ligation;

FIG. 15A shows an example of the combinatorial space of identifiers that may be constructed using the component deletion scheme; FIG. 15B shows an example implementation of the component deletion scheme using double stranded targeted cleavage and repair;

FIG. 17A shows example methods for using polymerase chain reaction, affinity tagged probes, and degradation targeting probes to access identifiers containing a specified component; FIG. 17B shows example methods for using polymerase chain reaction to perform 'OR' or 'AND' operations to access identifiers containing multiple specified components; FIG. 17C shows example methods for using affinity tags to perform 'OR' or 'AND' operations to access identifiers containing multiple specified components;

FIG. 18A shows an example of encoding, writing, and reading 5,856 bits of data; FIG. 18b shows an example of encoding, writing, and reading 62,824 bits of data.

DETAILED DESCRIPTION

Figure 1:
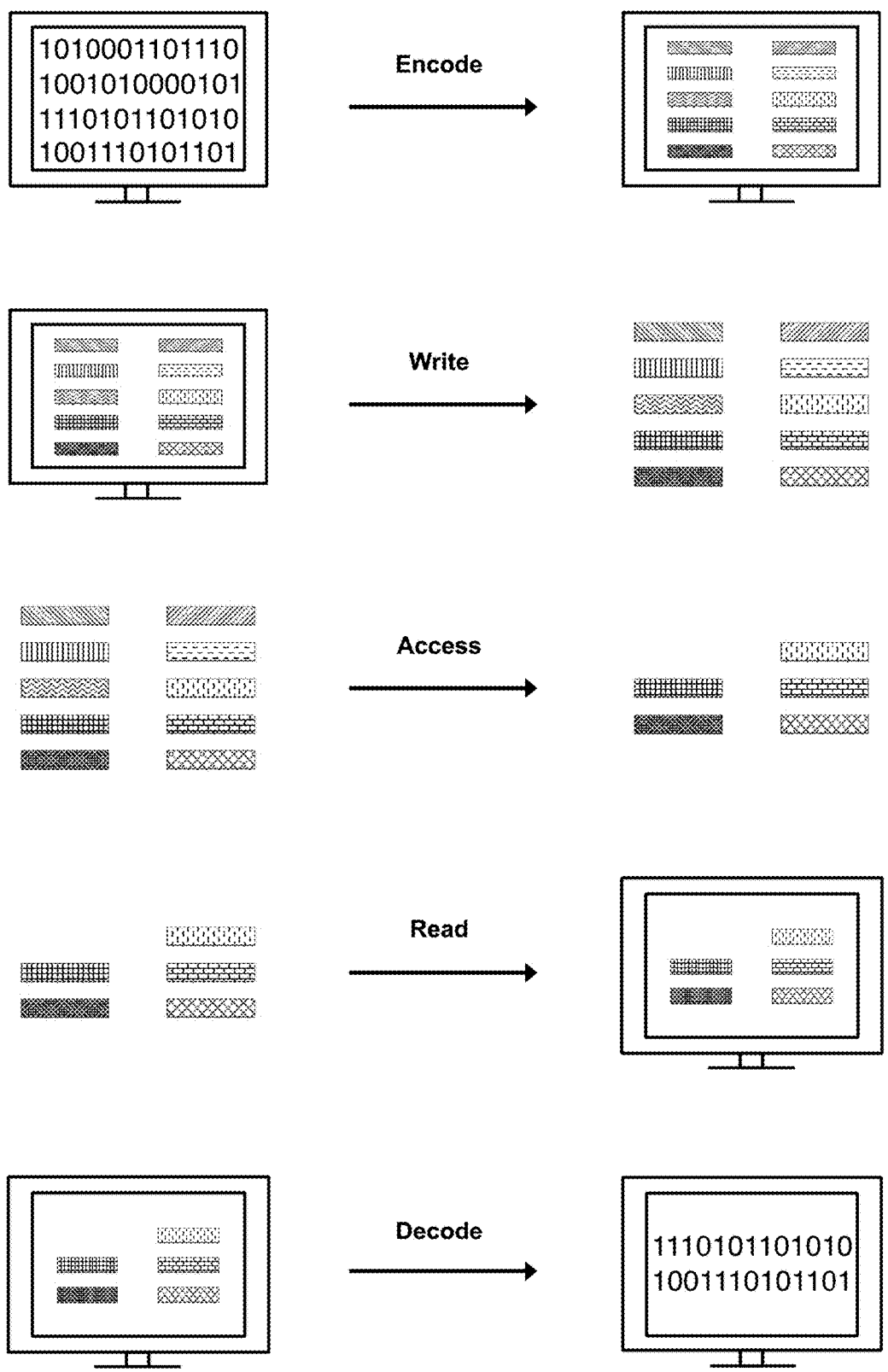
FIG. 1 schematically illustrates an overview of a process for encoding, writing, accessing, reading, and decoding digital information stored in nucleic acid sequences.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "symbol," as used herein, generally refers to a representation of a unit of digital information. Digital information may be divided or translated into a string of symbols. In an example, a symbol may be a bit and the bit may have a value of '0' or '1'.

The term "distinct," or "unique," as used herein, generally refers to an object that is distinguishable from other objects in a group. For example, a distinct, or unique, nucleic acid sequence may be a nucleic acid sequence that does not have the same sequence as any other nucleic acid sequence. A distinct, or unique, nucleic acid molecule may not have the same sequence as any other nucleic acid molecule. The distinct, or unique, nucleic acid sequence or molecule may share regions of similarity with another nucleic acid sequence or molecule.

The term "component," as used herein, generally refers to a nucleic acid sequence. A component may be a distinct nucleic acid sequence. A component may be concatenated or assembled with one or more other components to generate other nucleic acid sequence or molecules.

The term "layer," as used herein, generally refers to group or pool of components. Each layer may comprise a set of distinct components such that the components in one layer are different from the components in another layer. Components from one or more layers may be assembled to generate one or more identifiers.

The term "identifier," as used herein, generally refers to a nucleic acid molecule or a nucleic acid sequence that represents the position and value of a bit-string within a larger bit-string. More generally, an identifier may refer to any object that represents or corresponds to a symbol in a string of symbols. In some embodiments, identifiers may comprise one or multiple concatenated components.

The term "combinatorial space," as used herein generally refers to the set of all possible distinct identifiers that may be generated from a starting set of objects, such as components, and a permissible set of rules for how to modify those objects to form identifiers. The size of a combinatorial space of identifiers made by assembling or concatenating components may depend on the number of layers of components, the number of components in each layer, and the particular assembly method used to generate the identifiers.

The term "identifier rank," as used herein generally refers to a relation that defines the order of identifiers in a set.

The term "identifier library," as used herein generally refers to a collection of identifiers corresponding to the symbols in a symbol string representing digital information. In some embodiments, the absence of a given identifier in the identifier library may indicate a symbol value at a particular position. One or more identifier libraries may be combined in a pool, group, or set of identifiers. Each identifier library may include a unique barcode that identifies the identifier library.

The term "nucleic acid," as used herein, general refers to deoxyribonucleic acid (DNA), ribonucleic acid (RNA), or a variant thereof. A nucleic acid may include one or more subunits selected from adenosine (A), cytosine (C), guanine (G), thymine (T), and uracil (U), or variants thereof. A nucleotide can include A, C, G, T, or U, or variants thereof. A nucleotide can include any subunit that can be incorporated into a growing nucleic acid strand. Such subunit can be A, C, G, T, or U, or any other subunit that may be specific to one of more complementary A, C, G, T, or U, or complementary to a purine (i.e., A or G, or variant thereof) or pyrimidine (i.e., C, T, or U, or variant thereof). In some examples, a nucleic acid may be single-stranded or double stranded, in some cases, a nucleic acid is circular.

The terms "nucleic acid molecule" or "nucleic acid sequence," as used herein, generally refer to a polymeric form of nucleotides, or polynucleotide, that may have various lengths, either deoxyribonucleotides (DNA) or ribonucleotides (RNA), or analogs thereof. The term "nucleic acid sequence" may refer to the alphabetical representation of a polynucleotide; alternatively, the term may be applied to the physical polynucleotide itself. This alphabetical representation can be input into databases in a computer having a central processing unit and used for mapping nucleic acid sequences or nucleic acid molecules to symbols, or bits, encoding digital information. Nucleic acid sequences or oligonucleotides may include one or more non-standard nucleotide(s), nucleotide analog(s) and/or modified nucleotides.

An "oligonucleotide", as used herein, generally refers to a single-stranded nucleic acid sequence, and is typically composed of a specific sequence of four nucleotide bases: adenine (A); cytosine (C); guanine (G), and thymine (T) or uracil (U) when the polynucleotide is RNA.

Examples of modified nucleotides include, but are not limited to diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexylacrylamide-dCTP (aha-dCTP) to allow covalent attachment of amine reactive moieties, such as N-hydroxy succinimide esters (NHS).

The term "primer," as used herein, generally refers to a strand of nucleic acid that serves as a starting point for nucleic acid synthesis, such as polymerase chain reaction (PCR). In an example, during replication of a DNA sample, an enzyme that catalyzes replication starts replication at the 3'-end of a primer attached to the DNA sample and copies the opposite strand.

The term "polymerase" or "polymerase enzyme," as used herein, generally refers to any enzyme capable of catalyzing a polymerase reaction. Examples of polymerases include, without limitation, a nucleic acid polymerase. The polymerase can be naturally occurring or synthesized. An example polymerase is a Φ29 polymerase or derivative thereof. In some cases, a transcriptase or a ligase is used (i.e., enzymes which catalyze the formation of a bond) in conjunction with polymerases or as an alternative to polymerases to construct new nucleic acid sequences. Examples of polymerases include a DNA polymerase, a RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase Pwo polymerase, VENT polymerase, DEEPVENT polymerase, Ex-Taq polymerase, LA-Taw polymerase, Sso polymerase Poc polymerase, Pab polymerase, Mth polymerase ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Pfutubo polymerase, Pyrobest polymerase, KOD polymerase, Bst polymerase, Sac polymerase, Klenow fragment polymerase with 3' to 5' exonuclease activity, and variants, modified products and derivatives thereof.

Digital information, such as computer data, in the form of binary code can comprise a sequence or string of symbols. A binary code may encode or represent text or computer processor instructions using, for example, a binary number system having two binary symbols, typically 0 and 1, referred to as bits. Digital information may be represented in the form of non-binary code which can comprise a sequence of non-binary symbols. Each encoded symbol can be re-assigned to a unique bit string (or "byte"), and the unique bit string or byte can be arranged into strings of bytes or byte streams. A bit value for a given bit can be one of two symbols (e.g., 0 or 1). A byte, which can comprise a string of N bits, can have a total of $2^N$ unique byte-values. For example, a byte comprising 8 bits can produce a total of $2^8$ or 256 possible unique byte-values, and each of the 256 bytes can correspond to one of 256 possible distinct symbols, letters, or instructions which can be encoded with the bytes. Raw data (e.g., text files and computer instructions) can be represented as strings of bytes or byte streams. Zip files, or compressed data files comprising raw data can also be stored in byte streams, these files can be stored as byte streams in a compressed form, and then decompressed into raw data before being read by the computer.

Methods and systems of the present disclosure may be used to encode computer data or information in a plurality of identifiers, each of which may represent one or more bits of the original information. In some examples, methods and systems of the present disclosure encode data or information using identifiers that each represents two bits of the original information.

Previous methods for encoding digital information into nucleic acids have relied on base-by-base synthesis of the nucleic acids, which can be costly and time consuming. Alternative methods may improve the efficiency, improve the commercial viability of digital information storage by reducing the reliance on base-by-base nucleic acid synthesis for encoding digital information, and eliminate the de novo synthesis of distinct nucleic acid sequences for every new information storage request.

New methods can encode digital information (e.g., binary code) in a plurality of identifiers, or nucleic acid sequences, comprising combinatorial arrangements of components instead of relying on base-by-base or de-novo nucleic acid synthesis (e.g., phosphoramidite synthesis). As such, new strategies may produce a first set of distinct nucleic acid sequences (or components) for the first request of information storage, and can there-after re-use the same nucleic acid sequences (or components) for subsequent information storage requests. These approaches can significantly reduce the cost of DNA-based information storage by reducing the role of de-novo synthesis of nucleic acid sequences in the information-to-DNA encoding and writing process. Moreover, unlike implementations of base-by-base synthesis, such as phosphoramidite chemistry- or template-free polymerase-based nucleic acid elongation, which may use cyclical delivery of each base to each elongating nucleic acid, new methods of information-to-DNA writing using identifier construction from components are highly parallelizable processes that do not necessarily use cyclical nucleic acid elongation. Thus, new methods may increase the speed of writing digital information to DNA compared to older methods.

Methods for Encoding and Writing Information to Nucleic Acid Sequence(s)

In an aspect, the present disclosure provides methods for encoding information into nucleic acid sequences. A method for encoding information into nucleic acid sequences may comprise (a) translating the information into a string of symbols, (b) mapping the string of symbols to a plurality of identifiers, and (c) constructing an identifier library comprising at least a subset of the plurality of identifiers. An individual identifier of the plurality of identifiers may comprise one or more components. An individual component of the one or more components may comprise a nucleic acid sequence. Each symbol at each position in the string of symbols may correspond to a distinct identifier. The individual identifier may correspond to an individual symbol at an individual position in the string of symbols. Moreover, one symbol at each position in the string of symbols may correspond to the absence of an identifier. For example, in a string of binary symbols (e.g., bits) of '0's and '1's, each occurrence of '0' may correspond to the absence of an identifier.

In another aspect, the present disclosure provides methods for nucleic acid-based computer data storage. A method for nucleic acid-based computer data storage may comprise (a) receiving computer data, (b) synthesizing nucleic acid molecules comprising nucleic acid sequences encoding the computer data, and (c) storing the nucleic acid molecules having the nucleic acid sequences. The computer data may be encoded in at least a subset of nucleic acid molecules synthesized and not in a sequence of each of the nucleic acid molecules.

In another aspect, the present disclosure provides methods for writing and storing information in nucleic acid sequences. The method may comprise, (a) receiving or encoding a virtual identifier library that represents information, (b) physically constructing the identifier library, and (c) storing one or more physical copies of the identifier library in one or more separate locations. An individual identifier of the identifier library may comprise one or more components. An individual component of the one or more components may comprise a nucleic acid sequence.

In another aspect, the present disclosure provides methods for nucleic acid-based computer data storage. A method for nucleic acid-based computer data storage may comprise (a) receiving computer data, (b) synthesizing a nucleic acid molecule comprising at least one nucleic acid sequence encoding the computer data, and (c) storing the nucleic acid molecule comprising the at least one nucleic acid sequence. Synthesizing the nucleic acid molecule may be in the absence of base-by-base nucleic acid synthesis.

In another aspect, the present disclosure provides methods for writing and storing information in nucleic acid sequences. A method for writing and storing information in nucleic acid sequences may comprise, (a) receiving or encoding a virtual identifier library that represents information, (b) physically constructing the identifier library, and (c) storing one or more physical copies of the identifier library in one or more separate locations. An individual identifier of the identifier library may comprise one or more components. An individual component of the one or more components may comprise a nucleic acid sequence.

FIG. 1 illustrates an overview process for encoding information into nucleic acid sequences, writing information to the nucleic acid sequences, reading information written to nucleic acid sequences, and decoding the read information. Digital information, or data, may be translated into one or more strings of symbols. In an example, the symbols are bits and each bit may have a value of either '0' or '1'. Each symbol may be mapped, or encoded, to an object (e.g., identifier) representing that symbol. Each symbol may be represented by a distinct identifier. The distinct identifier may be a nucleic acid molecule made up of components. The components may be nucleic acid sequences. The digital information may be written into nucleic acid sequences by generating an identifier library corresponding to the information. The identifier library may be physically generated by physically constructing the identifiers that correspond to each symbol of the digital information. All or any portion of the digital information may be accessed at a time. In an example, a subset of identifiers is accessed from an identifier library. The subset of identifiers may be read by sequencing and identifying the identifiers. The identified identifiers may be associated with their corresponding symbol to decode the digital data.

A method for encoding and reading information using the approach of FIG. 1 can, for example, include receiving a bit stream and mapping each one-bit (bit with bit-value of '1') in the bit stream to a distinct nucleic acid identifier using an identifier rank or a nucleic acid index. Constructing a nucleic acid sample pool, or identifier library, comprising copies of the identifiers that correspond to bit values of 1 (and excluding identifiers for bit values of 0). Reading the sample can comprise using molecular biology methods (e.g., sequencing, hybridization, PCR, etc), determining which identifiers are represented in the identifier library, and assigning bit-values of '1' to the bits corresponding to those identifiers and bit-values of '0' elsewhere (again referring to the identifier rank to identify the bits in the original bit-stream that each identifier corresponds to), thus decoding the information into the original encoded bit stream.

Encoding a string of N distinct bits, can use an equivalent number of unique nucleic acid sequences as possible identifiers. This approach to information encoding may use de-novo synthesis of identifiers (e.g., nucleic acid molecules) for each new item of information (string of N bits) to store. In other instances, the cost of newly synthesizing identifiers (equivalent in number to or less than N) for each new item of information to store can be reduced by the one-time de-novo synthesis and subsequent maintenance of all possible identifiers, such that encoding new items of information may involve mechanically selecting and mixing together pre-synthesized (or pre-fabricated) identifiers to form an identifier library. In other instances, both the cost of (1) de-novo synthesis of up to N identifiers for each new item of information to store or (2) maintaining and selecting from N possible identifiers for each new item of information to store, or any combination thereof, may be reduced by synthesizing and maintaining a number (less than N, and in some cases much less than N) of nucleic acid sequences and then modifying these sequences through enzymatic reactions to generate up to N identifiers for each new item of information to store.

The identifiers may be rationally designed and selected for ease of read, write, access, copy, and deletion operations. The identifiers may be designed and selected to minimize write errors, mutations, degradation, and read errors.

Figure 2A:
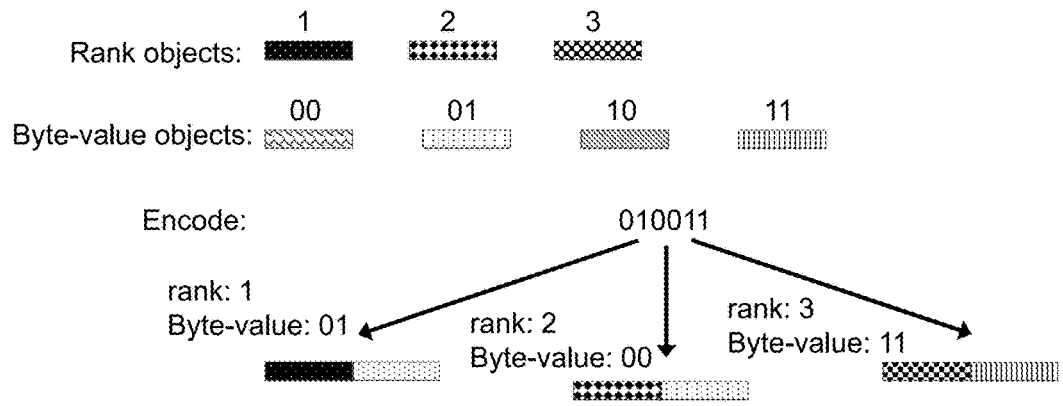
FIGS. 2A and 2B schematically illustrate an example method of encoding digital data, referred to as "data at address", using objects or identifiers (e.g., nucleic acid molecules)
Figure 2B:
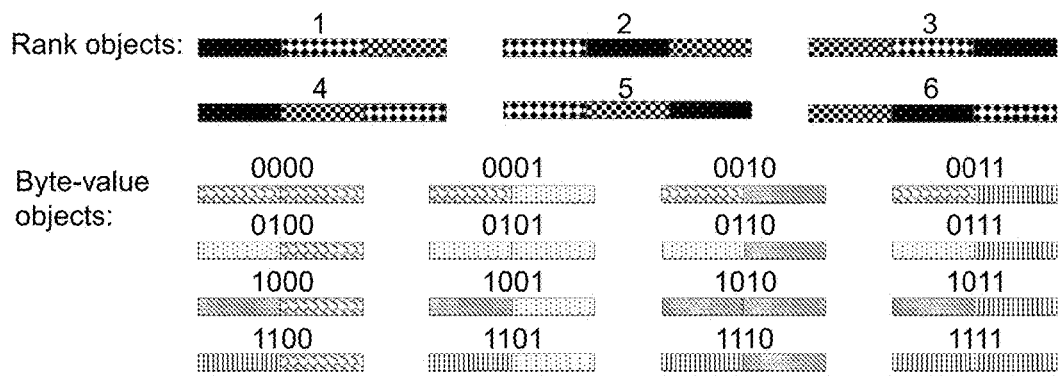

FIGS. 2A and 2B schematically illustrate an example method, referred to as "data at address", of encoding digital data in objects or identifiers (e.g., nucleic acid molecules). FIG. 2A illustrates encoding a bit stream into an identifier library wherein the individual identifiers are constructed by concatenating or assembling a single component that specifies an identifier rank with a single component that specifies a byte-value. In general, the data at address method uses identifiers that encode information modularly by comprising two objects: one object, the "byte-value object" (or "data object"), that identifies a byte-value and one object, the "rank object" (or "address object"), that identifies the identifier rank (or the relative position of the byte in the original bit-stream). FIG. 2B illustrates an example of the data at address method wherein each rank object may be combinatorially constructed from a set of components and each byte-value object may be combinatorially constructed from a set of components. Such combinatorial construction of rank and byte-value objects enables more information to be written into identifiers than if the objects where made from the single components alone (e.g., FIG. 2A).

Figure 3A:
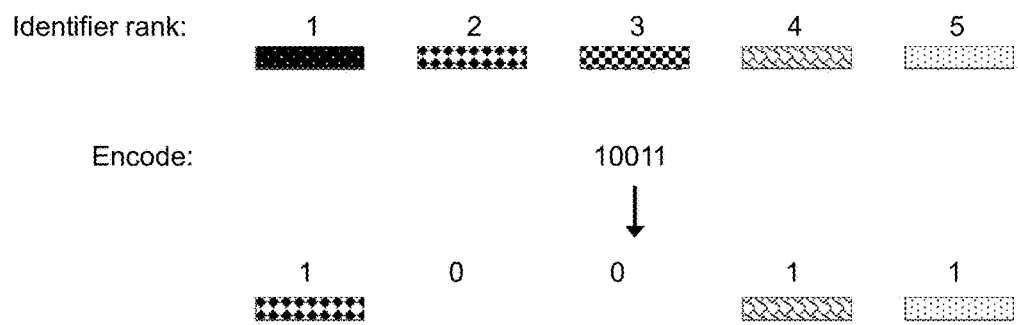
FIGS. 3A and 3B schematically illustrate an example method of encoding digital information using objects or identifiers (e.g., nucleic acid sequences)
Figure 3B:
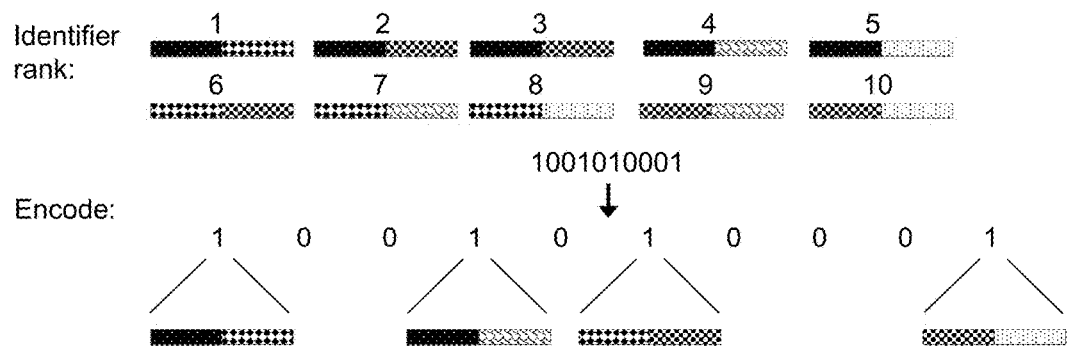

FIGS. 3A and 3B schematically illustrate another example method of encoding digital information in objects or identifiers (e.g., nucleic acid sequences). FIG. 3A illustrates encoding a bit stream into an identifier library wherein identifiers are constructed from single components that specify identifier rank. The presence of an identifier at a particular rank (or address) specifies a bit-value of '1' and the absence of an identifier at a particular rank (or address) specifies a bit-value of '0'. This type of encoding may use identifiers that solely encode rank (the relative position of a bit in the original bit stream) and use the presence or absence of those identifiers in an identifier library to encode a bit-value of '1' or '0', respectively. Reading and decoding the information may include identifying the identifiers present in the identifier library, assigning bit-values of '1' to their corresponding ranks and assigning bit-values of '0' elsewhere. FIG. 3B illustrates an example encoding method where each identifier may be combinatorially constructed from a set of components such that each possible combinatorial construction specifies a rank. Such combinatorial construction enables more information to be written into identifiers than if the identifiers where made from the single components alone (e.g., FIG. 3A). For example, a component set may comprise five distinct components. The five distinct components may be assembled to generate ten distinct identifiers, each comprising two of the five components. The ten distinct identifiers may each have a rank (or address) that corresponds to the position of a bit in a bit stream. An identifier library may include the subset of those ten possible identifiers that corresponds to the positions of bit-value '1', and exclude the subset of those ten possible identifiers that corresponds to the positions of the bit-value '0' within a bit stream of length ten.

Figure 4:
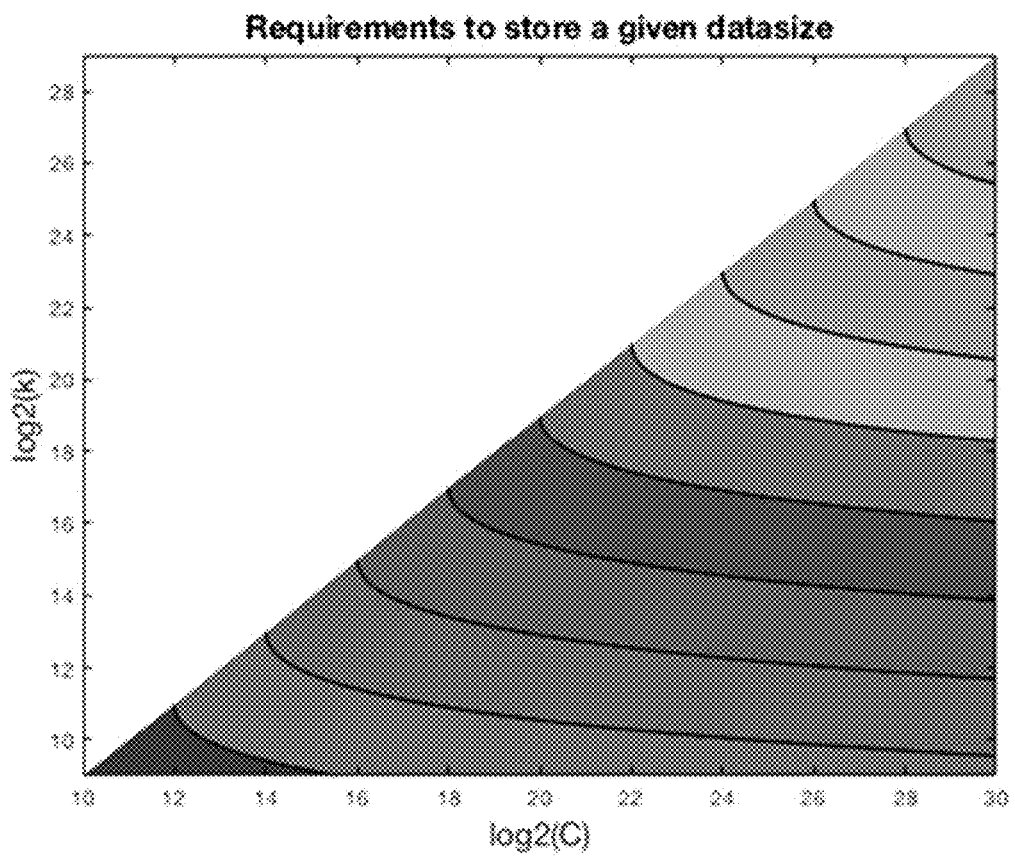
FIG. 4 shows a contour plot, in log space, of a relationship between the combinatorial space of possible identifiers (C, x-axis) and the average number of identifiers (k, y-axis) that may be constructed to store information of a given size (contour lines)

FIG. 4 shows a contour plot, in log space, of a relationship between the combinatorial space of possible identifiers (C, x-axis) and the average number of identifiers (k, y-axis) to be physically constructed in order to store information of a given original size in bits (D, contour lines) using the encoding method shown in FIGS. 3A and 3B. This plot assumes that the original information of size D is re-coded into a string of C bits (where C may be greater than D) where a number of bits, k, has a bit-value of '1'. Moreover, the plot assumes that information-to-nucleic-acid encoding is performed on the re-coded bit string and that identifiers for positions where the bit-value is '1' are constructed and identifiers for positions where the bit-value is '0' are not constructed. Following the assumptions, the combinatorial space of possible identifiers has size C to identify every position in the re-coded bit string, and the number of identifiers used to encode the bit string of size D is such that $D=\log_2(C\text{choose}k)$, where Cchoosek may be the mathematical formula for the number of ways to pick k unordered outcomes from C possibilities. Thus, as the combinatorial space of possible identifiers increases beyond the size (in bits) of a given item of information, a decreasing number of physically constructed identifiers may be used to store the given information.

Figure 5:
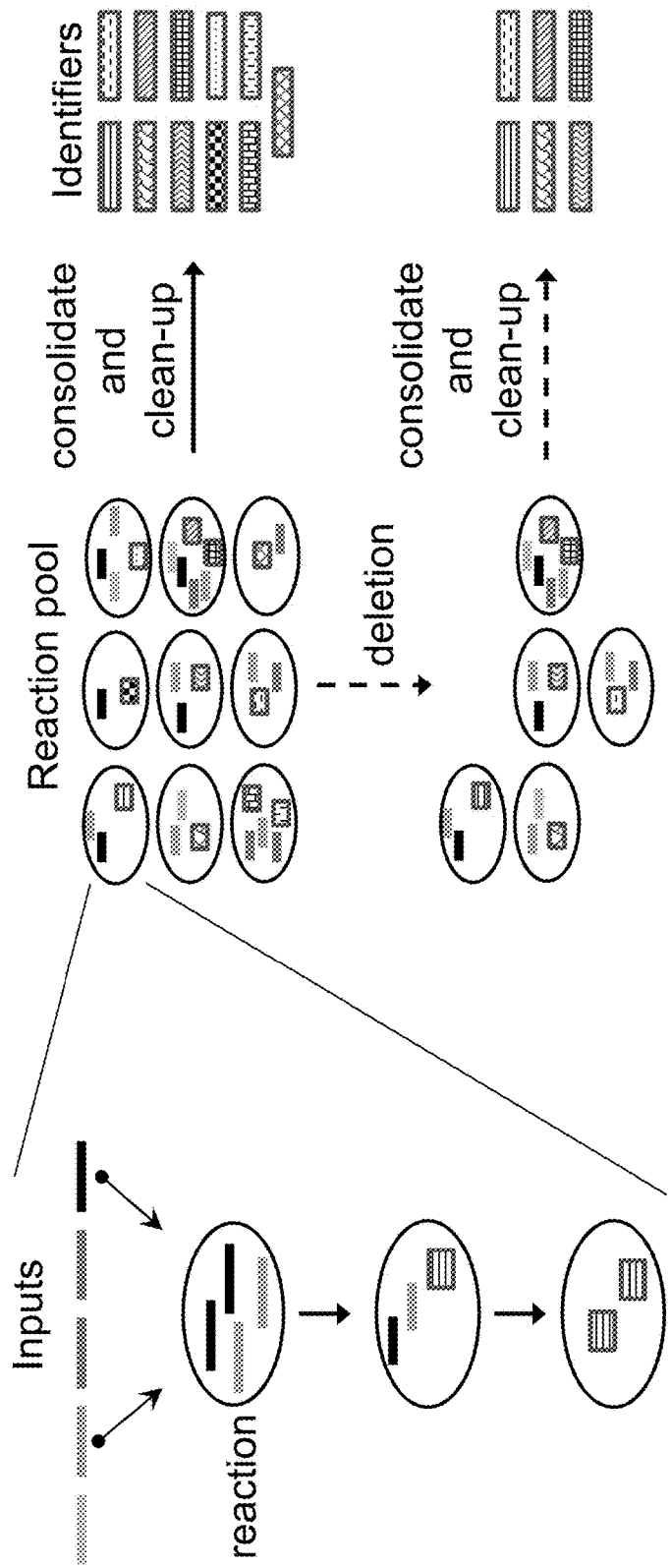
FIG. 5 schematically illustrates an overview of a method for writing information to nucleic acid sequences (e.g., deoxyribonucleic acid)

FIG. 5 shows an overview method for writing information into nucleic acid sequences. Prior to writing the information, the information may be translated into a string of symbols and encoded into a plurality of identifiers. Writing the information may include setting up reactions to produce possible identifiers. A reaction may be set up by depositing inputs into a compartment. The inputs may comprise nucleic acids, components, templates, enzymes, or chemical reagents. The compartment may be a well, a tube, a position on a surface, a chamber in a microfluidic device, or a droplet within an emulsion. Multiple reactions may be set up in multiple compartments. Reactions may proceed to produce identifiers through programmed temperature incubation or cycling. Reactions may be selectively or ubiquitously removed (e.g., deleted). Reactions may also be selectively or ubiquitously interrupted, consolidated, and purified to collect their identifiers in one pool. Identifiers from multiple identifier libraries may be collected in the same pool. An individual identifier may include a barcode or a tag to identify to which identifier library it belongs. Alternatively, or in addition to, the barcode may include metadata for the encoded information. Supplemental nucleic acids or identifiers may also be included in an identifier pool together with an identifier library. The supplemental nucleic acids or identifiers may include metadata for the encoded information or serve to obfuscate or conceal the encoded information.

An identifier rank (e.g., nucleic acid index) can comprise a method or key for determining the ordering of identifiers. The method can comprise a look-up table with all identifiers and their corresponding rank. The method can also comprise a look up table with the rank of all components that constitute identifiers and a function for determining the ordering of any identifier comprising a combination of those components. Such a method may be referred to as lexicographical ordering and may be analogous to the manner in which words in a dictionary are alphabetically ordered. In the data at address encoding method, the identifier rank (encoded by the rank object of the identifier) may be used to determine the position of a byte (encoded by the byte-value object of the identifier) within a bit stream. In an alternative method, the identifier rank (encoded by the entire identifier itself) for a present identifier may be used to determine the position of bit-value of '1' within a bit stream.

A key may assign distinct bytes to unique subsets of identifiers (e.g., nucleic acid molecules) within a sample. For example, in a simple form, a key may assign each bit in a byte to a unique nucleic acid sequence that specifies the position of the bit, and then the presence or absence of that nucleic acid sequence within a sample may specify the bit-value of 1 or 0, respectively. Reading the encoded information from the nucleic acid sample can comprise any number of molecular biology techniques including sequencing, hybridization, or PCR. In some embodiments, reading the encoded dataset may comprise reconstructing a portion of the dataset or reconstructing the entire encoded dataset from each nucleic acid sample. When the sequence may be read the nucleic acid index can be used along with the presence or absence of a unique nucleic acid sequence and the nucleic acid sample can be decoded into a bit stream (e.g., each string of bits, byte, bytes, or string of bytes).

Identifiers may be constructed by combinatorially assembling component nucleic acid sequences. For example, information may be encoded by taking a set of nucleic acid molecules (e.g., identifiers) from a defined group of molecules (e.g., combinatorial space). Each possible identifier of the defined group of molecules may be an assembly of nucleic acid sequences (e.g., components) from a prefabricated set of components that may be divided into layers. Each individual identifier may be constructed by concatenating one component from every layer in a fixed order. For example, if there are M layers and each layer may haven components, then up to $C=n^M$ unique identifiers may be constructed and up to $2^C$ different items of information, or C bits, may be encoded and stored. For example, storage of a megabit of information may use $1\times10^6$ distinct identifiers or a combinatorial space of size $C=1\times10^6$. The identifiers in this example may be assembled from a variety of components organized in different ways. Assemblies may be made from M=2 prefabricated layers, each containing $n=1\times10^3$ components. Alternatively, assemblies may be made from M=3 layers, each containing $n=1\times10^2$ components. As this example illustrates, encoding the same amount of information using a larger number of layers may allow for the total number of components to be smaller. Using a smaller number of total components may be advantageous in terms of writing cost.

In an example, one can start with two sets of unique nucleic acid sequences or layers, X and Y, each with x and y components (e.g., nucleic acid sequences), respectively. Each nucleic acid sequence from X can be assembled to each nucleic acid sequence from Y. Though the total number of nucleic acid sequences maintained in the two sets may be the sum of x and y, the total number of nucleic acid molecules, and hence possible identifiers, that can be generated may be the product of x and y. Even more nucleic acid sequences (e.g., identifiers) can be generated if the sequences from X can be assembled to the sequences of Y in any order. For example, the number of nucleic acid sequences (e.g., identifiers) generated may be twice the product of x and y if the assembly order is programmable. This set of all possible nucleic acid sequences that can be generated may be referred to as XY. The order of the assembled units of unique nucleic acid sequences in XY can be controlled using nucleic acids with distinct 5' and 3' ends, and restriction digestion, ligation, polymerase chain reaction (PCR), and sequencing may occur with respect to the distinct 5' and 3' ends of the sequences. Such an approach can reduce the total number of nucleic acid sequences (e.g., components) used to encode N distinct bits, by encoding information in the combinations and orders of their assembly products. For example, to encode 100 bits of information, two layers of 10 distinct nucleic acid molecules (e.g., component) may be assembled in a fixed order to produce 10*10 or 100 distinct nucleic acid molecules (e.g., identifiers), or one layer of 5 distinct nucleic acid molecules (e.g., components) and another layer of 10 distinct nucleic acid molecules (e.g., components) may be assembled in any order to produce 100 distinct nucleic acid molecules (e.g., identifiers).

Nucleic acid sequences (e.g., components) within each layer may comprise a unique (or distinct) sequence, or barcode, in the middle, a common hybridization region on one end, and another common hybridization region on another other end. The barcode may contain a sufficient number of nucleotides to uniquely identify every sequence within the layer. For example, there are typically four possible nucleotides for each base position within a barcode. Therefore, a three base barcode may uniquely identify $4^3$=64 nucleic acid sequences. The barcodes may be designed to be randomly generated. Alternatively, the barcodes may be designed to avoid sequences that may create complications to the construction chemistry of identifiers or sequencing. Additionally, barcodes may be designed so that each may have a minimum hamming distance from the other barcodes, thereby decreasing the likelihood that base-resolution mutations or read errors may interfere with the proper identification of the barcode.

The hybridization region on one end of the nucleic acid sequence (e.g., component) may be different in each layer, but the hybridization region may be the same for each member within a layer. Adjacent layers are those that have complementary hybridization regions on their components that allow them to interact with one another. For example, any component from layer X may be able to attach to any component from layer Y because they may have complementary hybridization regions. The hybridization region on the opposite end may serve the same purpose as the hybridization region on the first end. For example, any component from layer Y may attach to any component of layer X on one end and any component of layer Z on the opposite end.

Figure 6A:
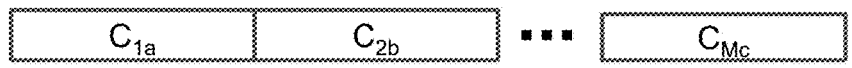
FIGS. 6A and 6B illustrate an example method, referred to as the "product scheme", for constructing identifiers (e.g., nucleic acid molecules) by combinatorially assembling distinct components (e.g., nucleic acid sequences)
Figure 6B:
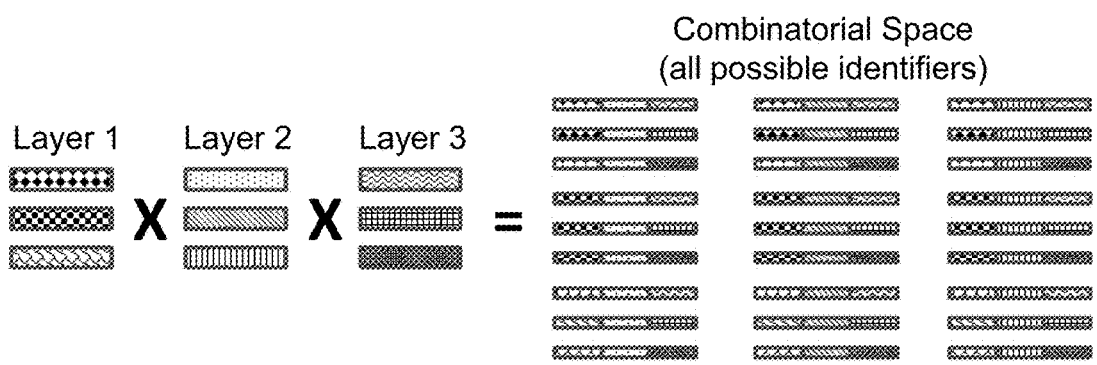

FIGS. 6A and 6B illustrate an example method, referred to as the "product scheme", for constructing identifiers (e.g., nucleic acid molecules) by combinatorially assembling a distinct component (e.g., nucleic acid sequence) from each layer in a fixed order. FIG. 6A illustrates the architecture of identifiers constructed using the product scheme. An identifier may be constructed by combining a single component from each layer in a fixed order. For M layers, each with N components, there are $N^M$ possible identifiers. FIG. 6B illustrates an example of the combinatorial space of identifiers that may be constructed using the product scheme. In an example, a combinatorial space may be generated from three layers each comprising three distinct components. The components may be combined such that one component from each layer may be combined in a fixed order. The entire combinatorial space for this assembly method may comprise twenty-seven possible identifiers.

FIGS. 7-10 illustrate chemical methods for implementing the product scheme (see FIG. 6). Methods depicted in FIGS. 7-10, along with any other methods for assembling two or more distinct components in a fixed order may be used, for example, to produce any one or more identifiers in an identifier library. Identifiers may be constructed using any of the implementation methods described in FIGS. 7-10, at any time during the methods or systems disclosed herein. In some instances, all or a portion of the combinatorial space of possible identifiers may be constructed before digital information is encoded or written, and then the writing process may involve mechanically selecting and pooling the identifiers (that encode the information) from the already existing set. In other instances, the identifiers may be constructed after one or more steps of the data encoding or writing process may have occurred (i.e., as information is being written).

Enzymatic reactions may be used to assemble components from the different layers or sets. Assembly can occur in a one pot reaction because components (e.g., nucleic acid sequences) of each layer have specific hybridization or attachment regions for components of adjacent layers. For example, a nucleic acid sequence (e.g., component) X1 from layer X, a nucleic acid sequence Y1 from layer Y, and a nucleic acid sequence Z1 from layer Z may form the assembled nucleic acid molecule (e.g., identifier) X1Y1Z1. Additionally, multiple nucleic acid molecules (e.g., identifiers) may be assembled in one reaction by including multiple nucleic acid sequences from each layer. For example, including both Y1 and Y2 in the one pot reaction of the previous example may yield two assembled products (e.g., identifiers), X1Y1Z1 and X1Y2Z1. This reaction multiplexing may be used to speed up writing time for the plurality of identifiers that are physically constructed. Assembly of the nucleic acid sequences may be performed in a time period that is less than or equal to about 1 day, 12 hours, 10 hours, 9 hours, 8 hours, 7 hours, 6 hours, 5 hours, 4 hours, 3 hours, 2 hours, or 1 hour. The accuracy of the encoded data may be at least about or equal to about 90%, 95%, 96%, 97%, 98%, 99%, or greater.

Figure 7:
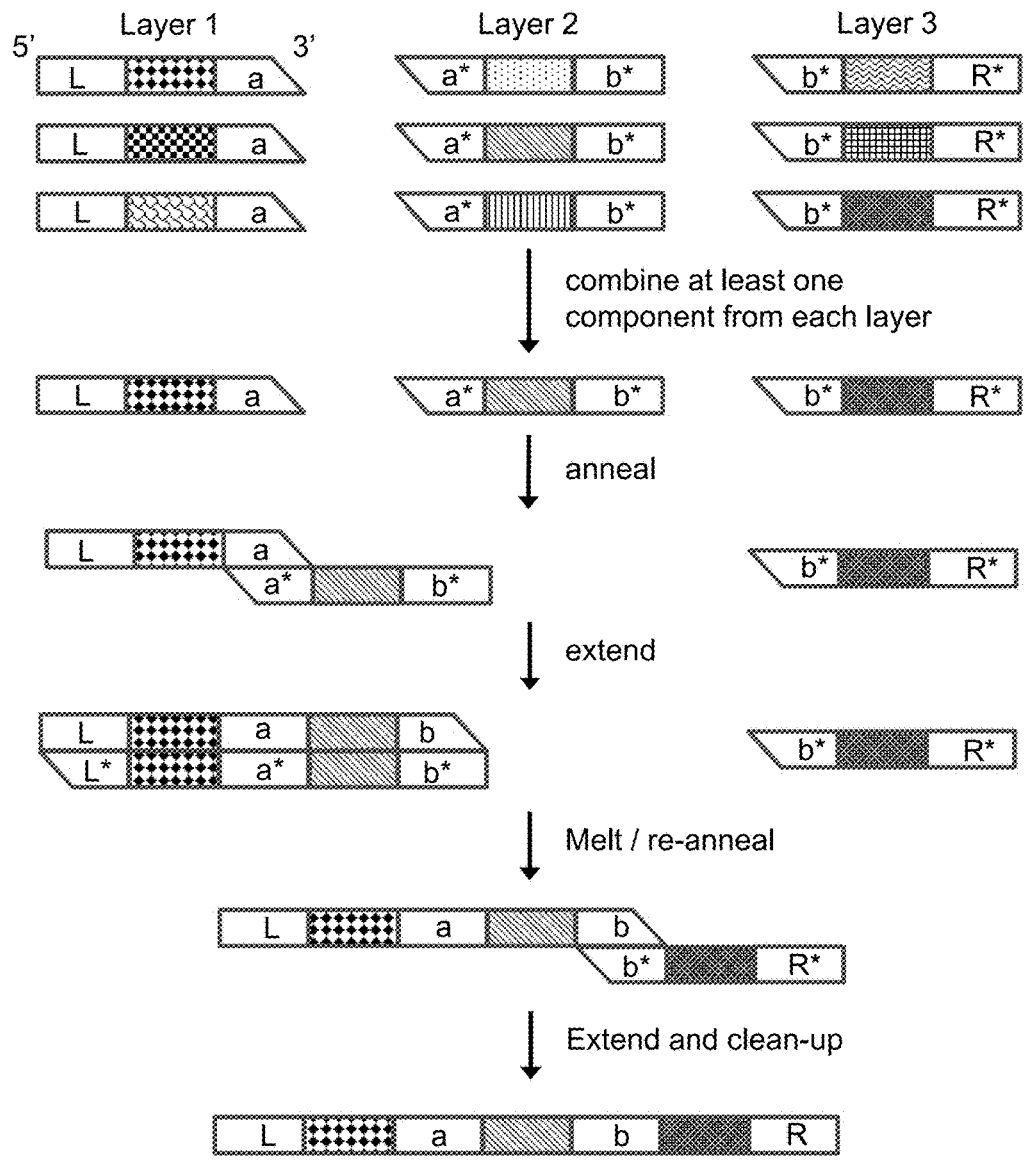
FIG. 7 schematically illustrates the use of overlap extension polymerase chain reaction to construct identifiers (e.g., nucleic acid molecules) from components (e.g., nucleic acid sequences)

Identifiers may be constructed in accordance with the product scheme using overlap extension polymerase chain reaction (OEPCR), as illustrated in FIG. 7. Each component in each layer may comprise a double-stranded or single stranded (as depicted in the figure) nucleic acid sequence with a common hybridization region on the sequence end that may be homologous and/or complementary to the common hybridization region on the sequence end of components from an adjacent layer. An individual identifier may be constructed by concatenating one component (e.g., unique sequence) from a layer X (or layer 1) comprising components $X_1$-$X_A$, a second component (e.g., unique sequence) from a layer Y (or layer 2) comprising $Y_1$-$Y_A$, and a third component (e.g., unique sequence) from layer Z (or layer 3) comprising $Z_1$-$Z_B$. The components from layer X may have a 3' end that shares complementarity with the 3' end on components from layer Y. Thus single-stranded components from layer X and Y may be annealed together at the 3' end and may be extended using PCR to generate a double-stranded nucleic acid molecule. The generated double-stranded nucleic-acid molecule may be melted to generate a 3' end that shares complementarity with a 3' end of a component from layer Z. A component from layer Z may be annealed with the generated nucleic acid molecule and may be extended to generate a unique identifier comprising a single component from layers X, Y, and Z in a fixed order. DNA size selection (e.g., with gel extraction) or polymerase chain reaction (PCR) with primers flanking the outer most layers may be implemented to isolate identifier products from other byproducts that may form in the reaction.

Figure 8:
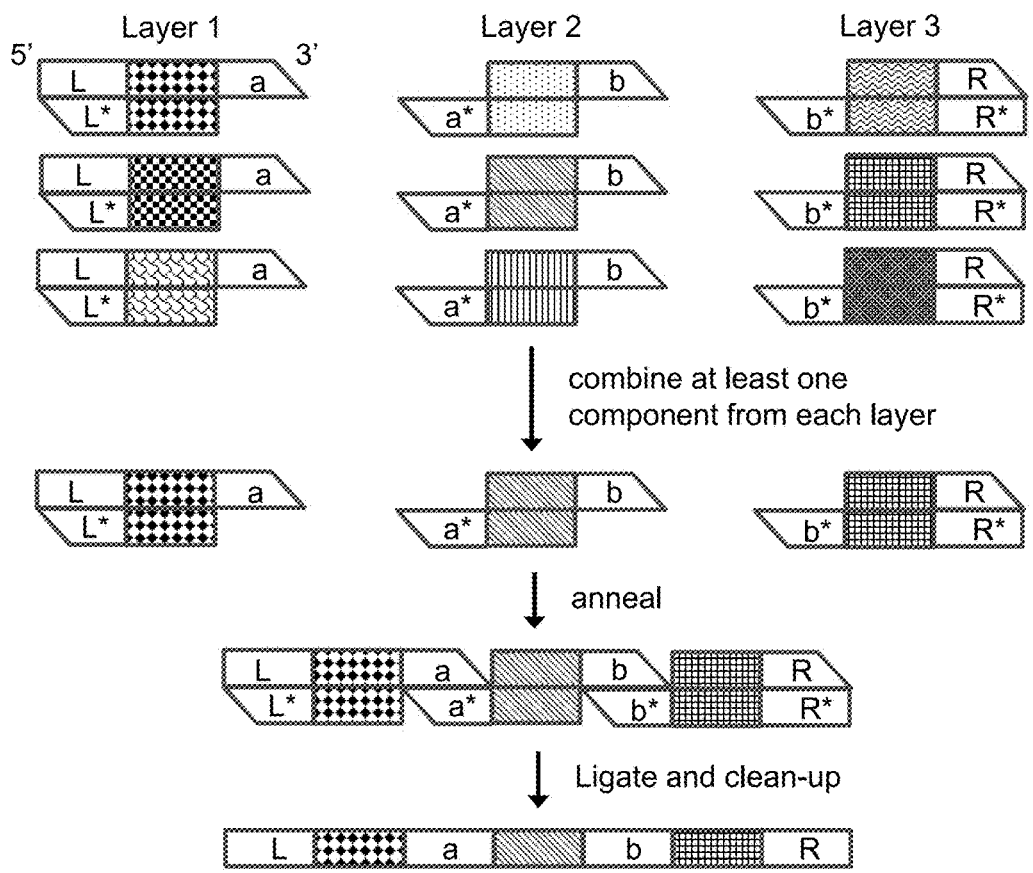
FIG. 8 schematically illustrates the use of sticky end ligation to construct identifiers (e.g., nucleic acid molecules) from components (e.g., nucleic acid sequences)

Identifiers may be assembled in accordance with the product scheme using sticky end ligation, as illustrated in FIG. 8. Three layers, each comprising double stranded components (e.g., double stranded DNA (dsDNA)) with single-stranded 3' overhangs, can be used to assemble distinct identifiers. For example, identifiers comprising one component from the layer X (or layer 1) comprising components $X_1$-$X_A$, a second component from the layer Y (or layer 2) comprising $Y_1$-$Y_B$, and a third component from the layer Z (or layer 3) comprising $Z_1$-$Z_C$. To combine components from layer X with components from layer Y, the components in layer X can comprise a common 3' overhang, FIG. 8 labeled a, and the components in layer Y can comprise a common, complementary 3' overhang, a*. To combine components from layer Y with components from layer Z, the elements in layer Y can comprise a common 3' overhang, FIG. 8 labeled b, and the elements in layer Z can comprise a common, complementary 3' overhang, b*. The 3' overhang in layer X components can be complementary to the 3' end in layer Y components and the other 3' overhang in layer Y components can be complementary to the 3' end in layer Z components allowing the components to hybridize and ligate. As such, components from layer X cannot hybridize with other components from layer X or layer Z, and similarly components from layer Y cannot hybridize with other elements from layer Y. Furthermore, a single component from layer Y can ligate to a single component of layer X and a single component of layer Z, ensuring the formation of a complete identifier. DNA size selection (for example with gel extraction) or PCR with primers flanking the outer most layers may be implemented to isolate identifier products from other byproducts that may form in the reaction.

The sticky ends for sticky end ligation may be generated by treating the components of each layer with restriction endonucleases. In some embodiments, the components of multiple layers may be generated from one "parent" set of components. For example, an embodiment wherein a single parent set of double-stranded components may have complementary restrictions sites on each end (e.g., restriction sites for BamHI and BglII). Any two components may be selected for assembly, and individually digested with one or the other complementary restriction enzymes (e.g., BglII or BamHI) resulting in complementary sticky ends that can be ligated together resulting in an inert scar. The product nucleic acid sequence may comprise the complementary restriction sites on each end (e.g., BamHI on the 5' end and BglII on the 3' end), and can be further ligated to another component from the parent set following the same process. This process may cycle indefinitely. If the parent comprises N components, then each cycle may be equivalent to adding an extra layer of N components to the product scheme.

A method for using ligation to construct a sequence of nucleic acids comprising elements from set X (e.g., set 1 of dsDNA) and elements from set Y (e.g., set 2 of dsDNA) can comprise the steps of obtaining or constructing two or more pools (e.g., set 1 of dsDNA and set 2 of dsDNA) of double stranded sequences wherein a first set (e.g., set 1 of dsDNA) comprises a sticky end (e.g., a) and a second set (e.g., set 2 of dsDNA) comprises a sticky end (e.g., a*) that is complementary to the sticky end of the first set. Any DNA from the first set (e.g., set 1 of dsDNA) and any subset of DNA from the second set (e.g., set 2 of dsDNA) can me combined and assembled and then ligated together to form a single double stranded DNA with an element from the first set and an element from the second set.

Figure 9:
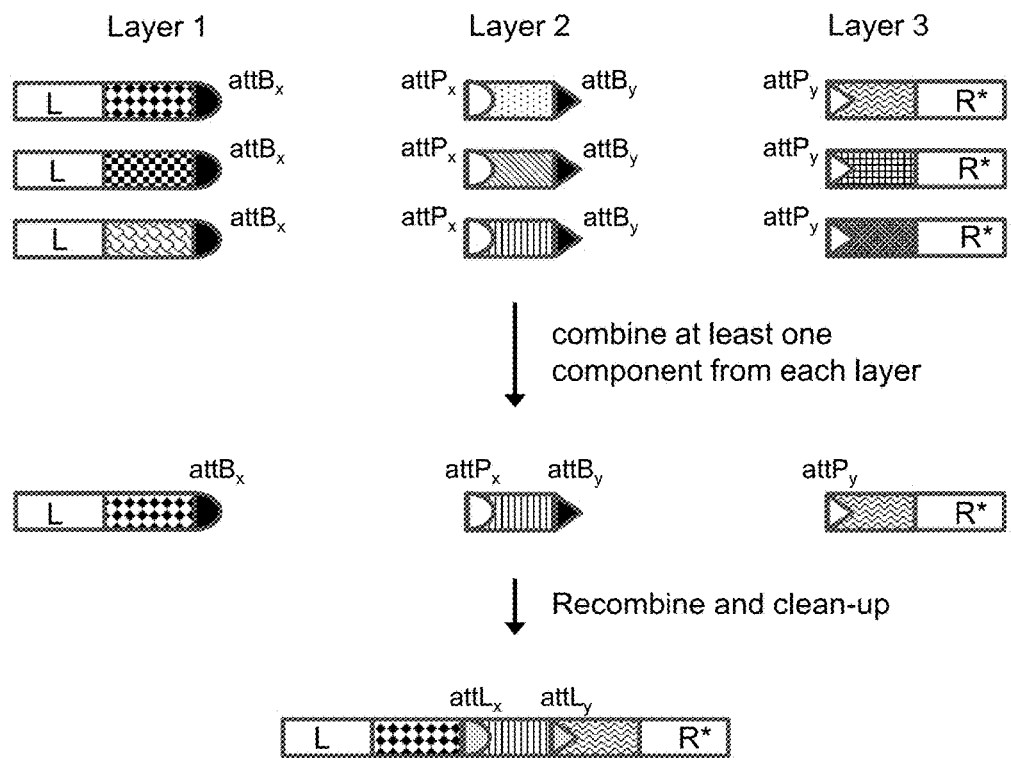
FIG. 9 schematically illustrates the use of recombinase assembly to construct identifiers (e.g., nucleic acid molecules) from components (e.g., nucleic acid sequences)

Identifiers may be assembled in accordance with the product scheme using site specific recombination, as illustrated in FIG. 9. Identifiers may be constructed by assembling components from three different layers. The components in layer X (or layer 1) may comprise double-stranded molecules with an attB recombinase site on one side of the molecule, components from layer Y (or layer 2) may comprise double-stranded molecules with an attP recombinase site on one side and an attB recombinase site on the other side, and components in layer Z (or layer 3) may comprise an attP recombinase site on one side of the molecule. attB and attP sites within a pair, as indicate by their subscripts, are capable of recombining in the presence of their corresponding recombinase enzyme. One component from each layer may be combined such that one component from layer X associates with one component from layer Y, and one component from layer Y associates with one component from layer Z. Application of one or more recombinase enzymes may recombine the components to generate a double-stranded identifier comprising the ordered components. DNA size selection (for example with gel extraction) or PCR with primers flanking the outer most layers may be implemented to isolate identifier products from other byproducts that may form in the reaction. In general, multiple orthogonal attB and attP pairs may be used, and each pair may be used to assemble a component from an extra layer. For the large-serine family of recombinases, up to six orthogonal attB and attP pairs may be generated per recombinases, and multiple orthogonal recombinases may be implemented as well. For example, thirteen layers may be assembled by using twelve orthogonal attB and attP pairs, six orthogonal pairs from each of two large serine recombinases, such as BxbI and PhiC31. Orthogonality of attB and attP pairs ensures that an attB site from one pair does not react with an attP site from another pair. This enables components from different layers to be assembled in a fixed order. Recombinase-mediated recombination reactions may be reversible or irreversible depending on the recombinase system implemented. For example, the large serine recombinase family catalyzes irreversible recombination reactions without requiring any high energy cofactors, whereas the tyrosine recombinase family catalyzes reversible reactions.

Figure 10A:
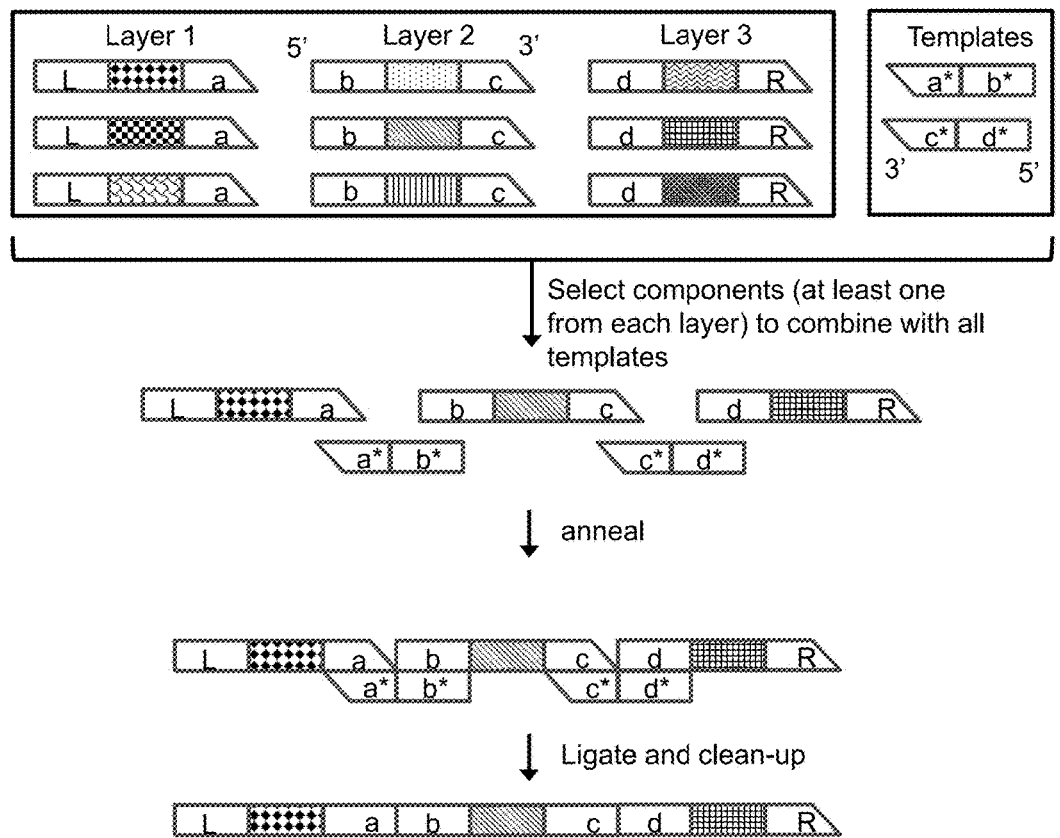
FIGS. 10A and 10B demonstrates template directed ligation.

Identifiers may be constructed in accordance with the product scheme using template directed ligation (TDL), as shown in FIG. 10A. Template directed ligation utilizes single stranded nucleic acid sequences, referred to as "templates" or "staples", to facilitate the ordered ligation of components to form identifiers. The templates simultaneously hybridize to components from adjacent layers and hold them adjacent to each other (3' end against 5' end) while a ligase ligates them. In the example from FIG. 10A, three layers or sets of single-stranded components are combined. A first layer of components (e.g., layer X or layer 1) that share common sequences a on their 3' end, which are complementary to sequences a*; a second layer of components (e.g., layer Y or layer 2) that share common sequences b and c on their 5' and 3' ends respectively, which are complementary to sequences b* and c*; a third layer of components (e.g., layer Z or layer 3) that share common sequence d on their 5' end, which may be complementary to sequences d*; and a set of two templates or "staples" with the first staple comprising the sequence a*b* (5' to 3') and the second staple comprising a sequence c*d* ('5 to 3'). In this example, one or more components from each layer may be selected and mixed into a reaction with the staples, which, by complementary annealing may facilitate the ligation of one component from each layer in a defined order to form an identifier. DNA size selection (for example with gel extraction) or PCR with primers flanking the outer most layers may be implemented to isolate identifier products from other byproducts that may form in the reaction.

Figure 10B:
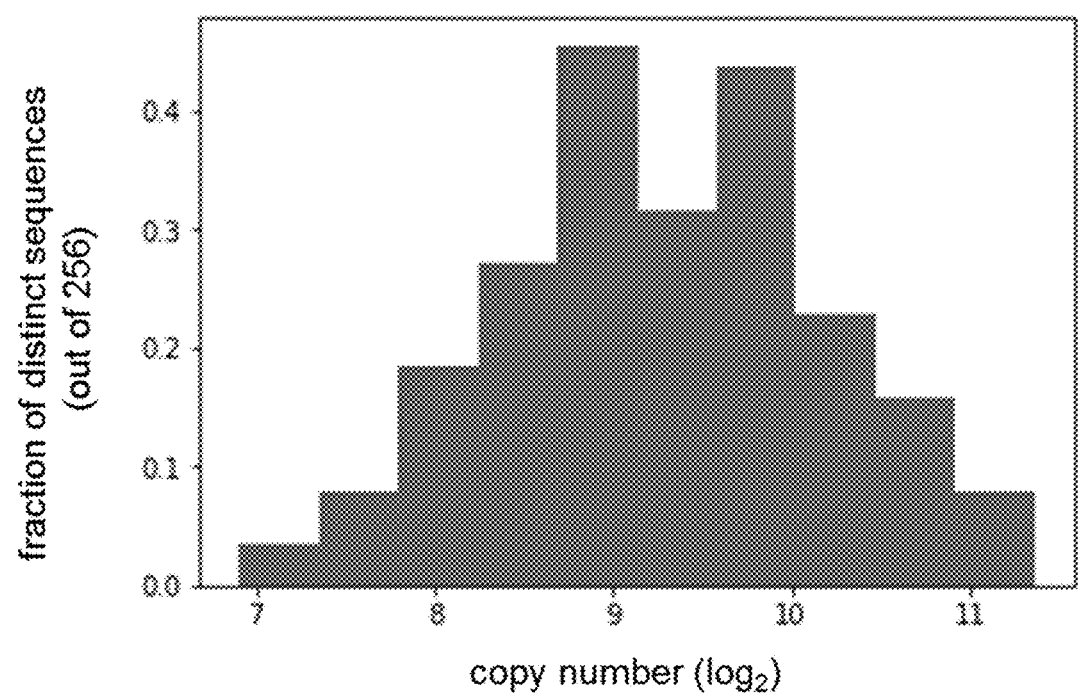

FIG. 10B shows a histogram of the copy numbers (abundances) of 256 distinct nucleic acid sequences that were each assembled with 6-layer TDL. The edge layers (first and final layers) each had one component, and each of the internal layers (remaining 4 four layers) had four components. Each edge layer component was 28 bases including a 10 base hybridization region. Each internal layer component was 30 bases including a 10 base common hybridization region on the 5' end, a 10 base variable (barcode) region, and a 10 base common hybridization region on the 3' end. Each of the three template strands was 20 bases in length. All 256 distinct sequences were assembled in a multiplex fashion with one reaction containing all of the components and templates, T4 Polynucleotide Kinase (for phosphorylating the components), and T4 Ligase, ATP, and other proper reaction reagents. The reaction was incubated at 37 degrees for 30 minutes and then room temperature for 1 hour. Sequencing adapters were added to the reaction product with PCR, and the product was sequenced with an Illumina MiSeq instrument. The relative copy number of each distinct assembled sequence out of 192910 total assembled sequence reads is shown. Other embodiments of this method may use double stranded components, where the components are initially melted to form single stranded versions that can anneal to the staples. Other embodiments or derivatives of this method (i.e., TDL) may be used to construct a combinatorial space of identifiers more complex than what may be accomplished in the product scheme.

Identifiers may be constructed in accordance with the product scheme using various other chemical implementations including golden gate assembly, gibson assembly, and ligase cycling reaction assembly.

Figure 11A:
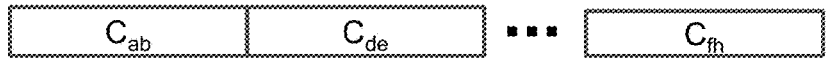
FIGS. 11A-11G schematically illustrate an example method, referred to as the "permutation scheme", for constructing identifiers (e.g., nucleic acid molecules) with permuted components (e.g., nucleic acid sequences)
Figure 11B:
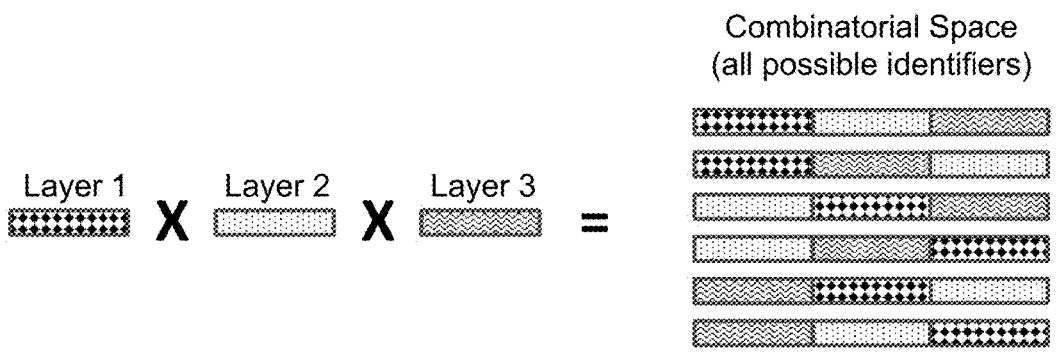

FIGS. 11A and 11B schematically illustrate an example method, referred to as the "permutation scheme", for constructing identifiers (e.g., nucleic acid molecules) with permuted components (e.g., nucleic acid sequences). FIG. 11A illustrates the architecture of identifiers constructed using the permutation scheme. An identifier may be constructed by combining a single component from each layer in a programmable order. FIG. 11B illustrates an example of the combinatorial space of identifiers that may be constructed using the permutation scheme. In an example, a combinatorial space of size six may be generated from three layers each comprising one distinct component. The components may be concatenated in any order. In general, with M layers, each with N components, the permutation scheme enables a combinatorial space of $N^M M!$ total identifiers.

Figure 11C:
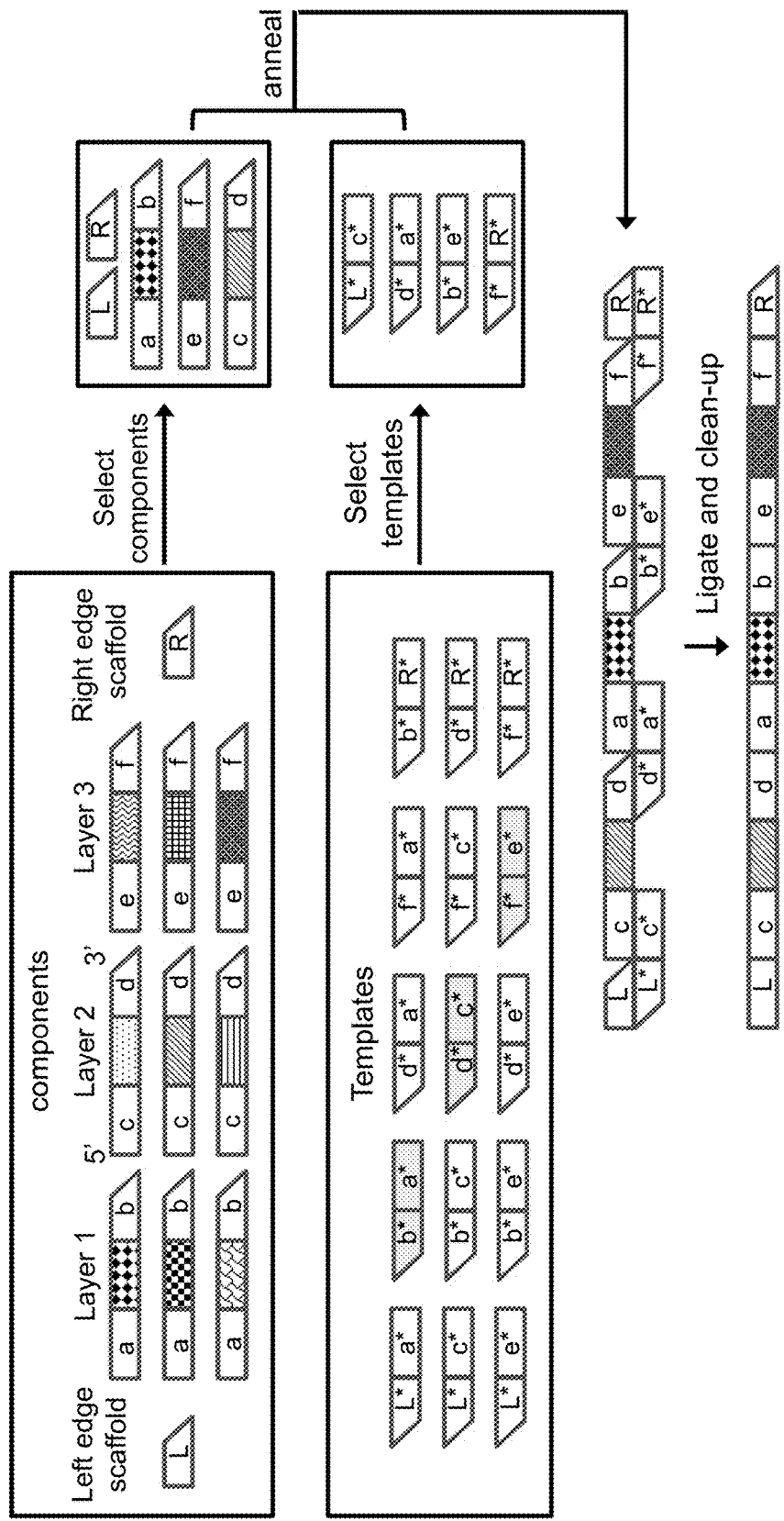

FIG. 11C illustrates an example implementation of the permutation scheme with template directed ligation (TDL). Components from multiple layers are assembled in between fixed left end and right end components, referred to as edge scaffolds. These edge scaffolds are the same for all identifiers in the combinatorial space and thus may be added as part of the reaction master mix for the implementation. Templates or staples exist for any possible junction between any two layers or scaffolds such that the order in which components from different layers are incorporated into an identifier in the reaction depends on the templates selected for the reaction. In order to enable any possible permutation of layers for M layers, there may be $M^2+2M$ distinct selectable staples for every possible junction (including junctions with the scaffolds). M of those templates (shaded in grey) form junctions between layers and themselves and may be excluded for the purposes of permutation assembly as described herein. However, their inclusion can enable a larger combinatorial space with identifiers comprising repeat components as illustrated in FIGS. 11D-G. DNA size selection (for example with gel extraction) or PCR with primers targeting the edge scaffolds may be implemented to isolate identifier products from other byproducts that may form in the reaction.

Figure 11D:
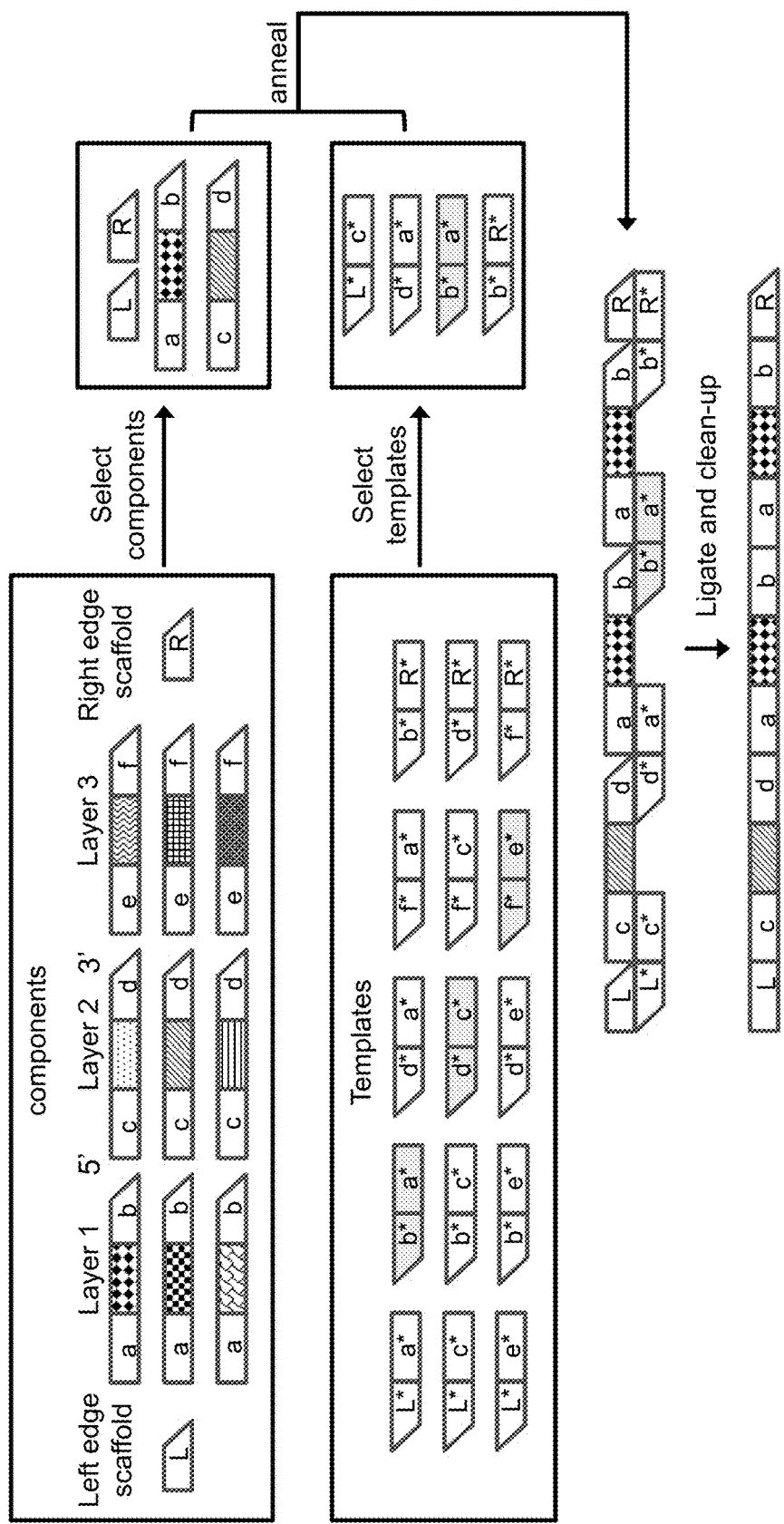
Figure 11E:
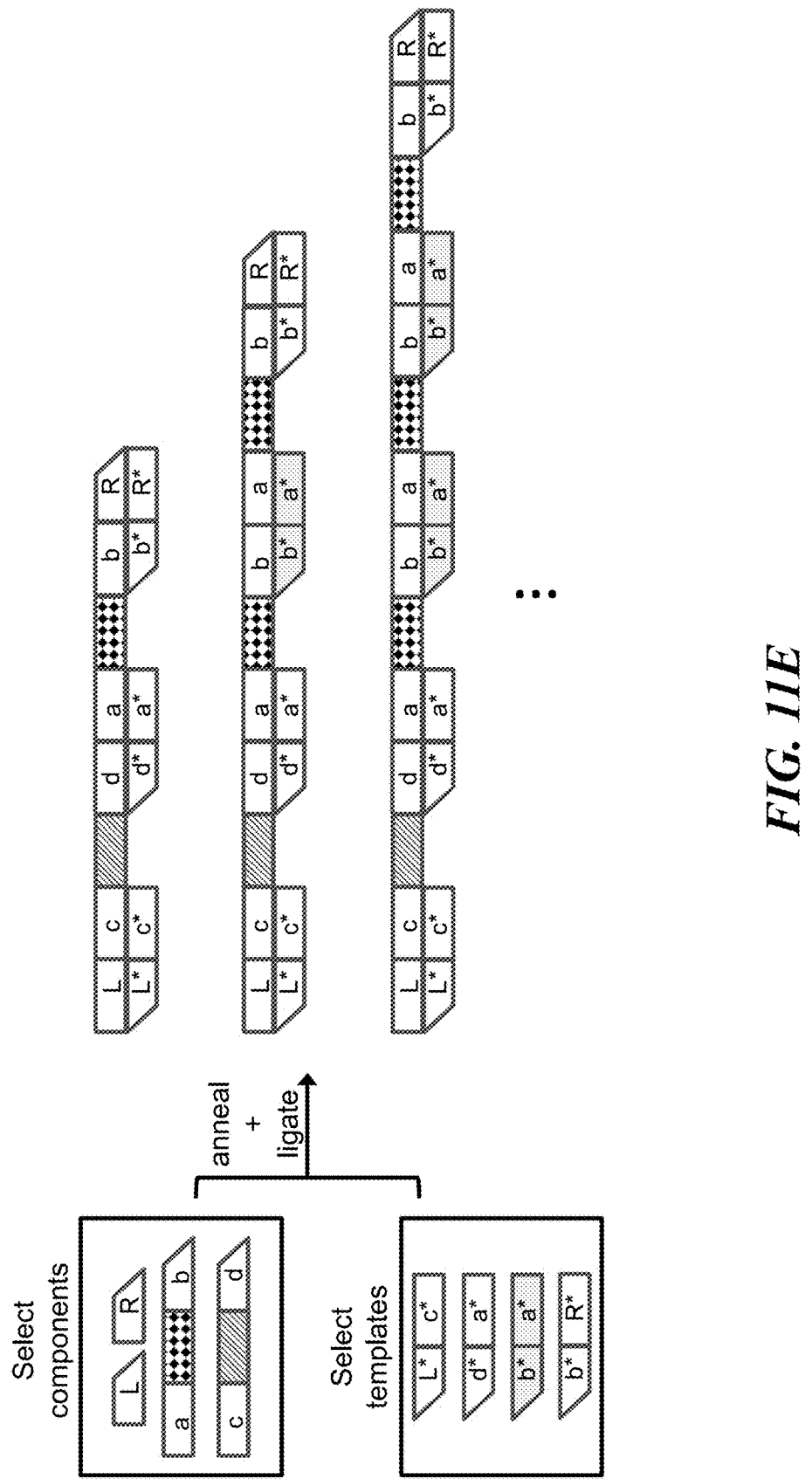
Figure 11F:
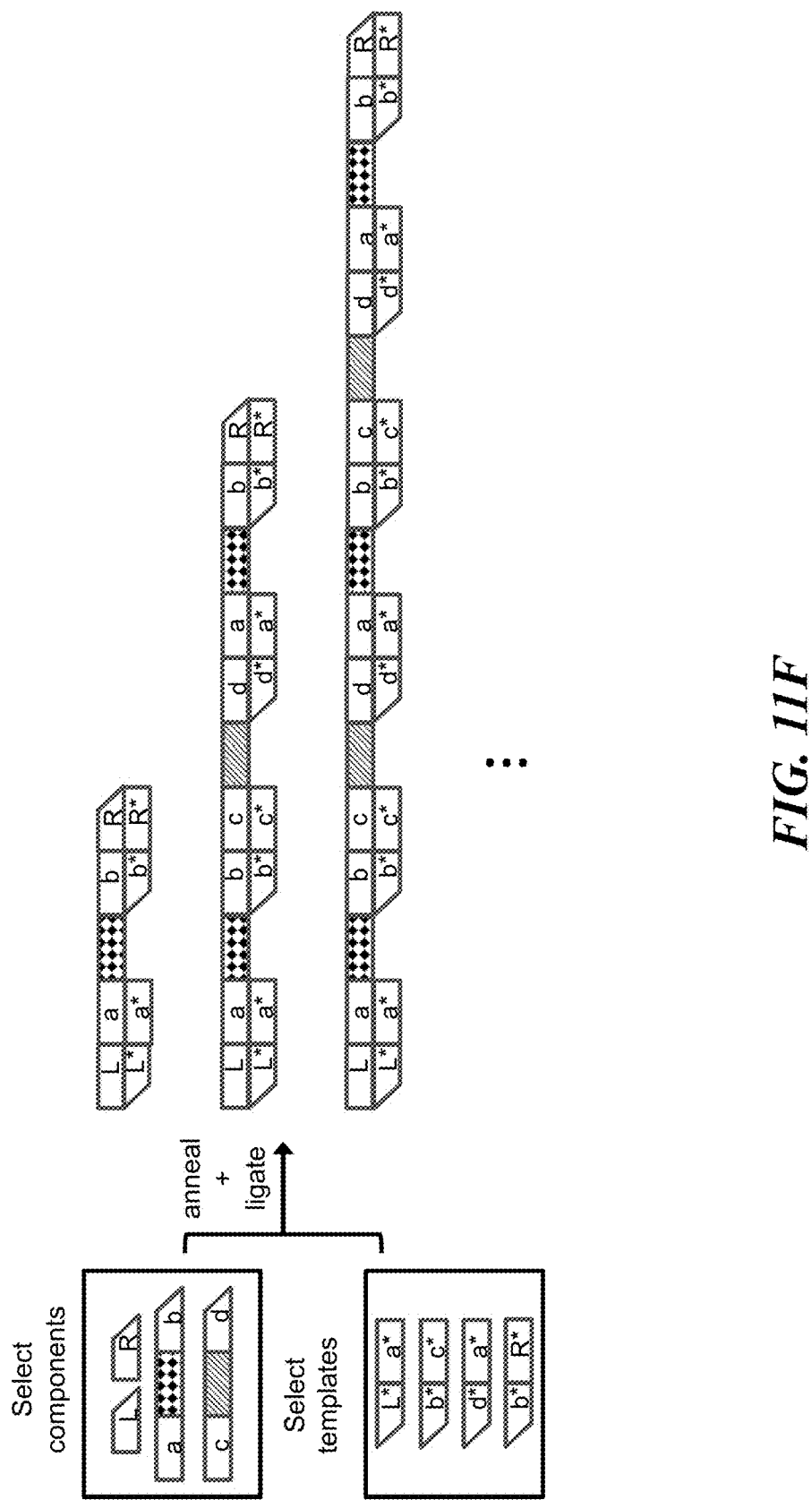
Figure 11G:
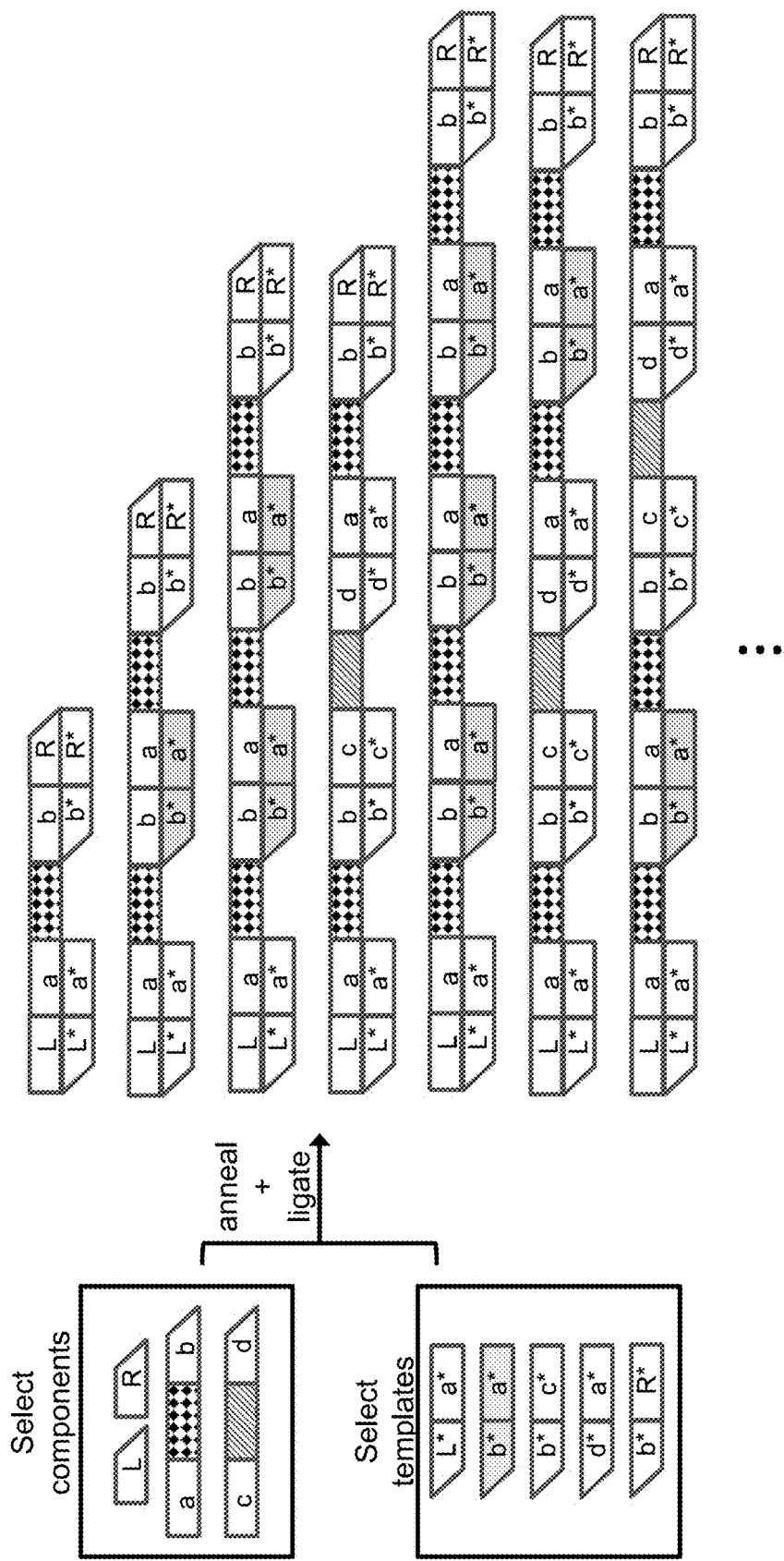

FIGS. 11D-G illustrate example methods of how the permutation scheme may be expanded to include certain instances of identifiers with repeated components. FIG. 11D shows an example of how the implementation form FIG. 11C may be used to construct identifiers with permuted and repeated components. For example, an identifier may comprise three total components assembled from two distinct components. In this example, a component from a layer may be present multiple times in an identifier. Adjacent concatenations of the same component may be achieved by using a staple with adjacent complementary hybridization regions for both the 3' end and 5' end of the same component, such as the a*b* (5' to 3') staple in the figure. In general, for M layers, there are M such staples. Incorporation of repeated components with this implementation may generate nucleic acid sequences of more than one length (i.e., comprising one, two, three, four, or more components) that are assembled between the edge scaffolds, as demonstrated in FIG. 11E. FIG. 11E shows how the example implementation from FIG. 11D may lead to non-targeted nucleic acid sequences, besides the identifier, that are assembled between the edge scaffolds. The appropriate identifier cannot be isolated from non-targeted nucleic acid sequence with PCR because they share the same primer binding sites on the edge. However, in this example, DNA size selection (e.g., with gel extraction) may be implemented to isolate the targeted identifier (e.g., the second sequence from the top) from the non-targeted sequences since each assembled nucleic acid sequence can be designed to have a unique length (e.g., if all components have the same length). FIG. 11F shows another example where constructing an identifier with repeated components may generate multiple nucleic acid sequences with equal edge sequences but distinct lengths in the same reaction. In this method, templates that assemble a components in one layer with components in other layers in an alternating pattern may be used. As with the method shown in FIG. 11E, size selection may be used to select identifiers of the designed length. FIG. 11G shows an example where constructing an identifier with repeated components may generate multiple nucleic acid sequences with equal edge sequences and for some nucleic acid sequences (e.g., the third and fourth from the top and the sixth and seventh from the top), equal lengths. In this example, those nucleic acid sequences that share equal lengths may be excluded from both being individual identifiers as it may not be possible to construct one without also constructing the other, even if PCR and DNA size selection are implemented.

Figure 12A:
FIGS. 12A-12D schematically illustrate an example method, referred to as the "MchooseK" scheme, for constructing identifiers (e.g., nucleic acid molecules) with any number, K, of assembled components (e.g., nucleic acid sequences) out of a larger number, M, of possible components.
Figure 12B:
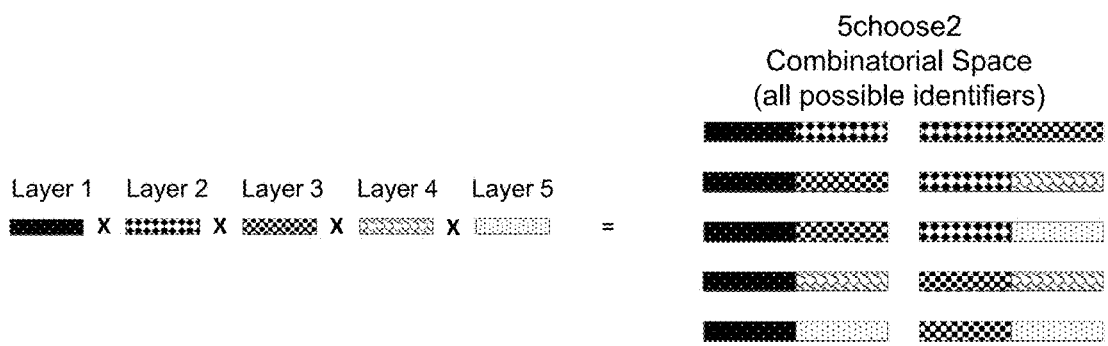

FIGS. 12A-12D schematically illustrate an example method, referred to as the "MchooseK scheme", for constructing identifiers (e.g., nucleic acid molecules) with any number, K, of assembled components (e.g., nucleic acid sequences) out of a larger number, M, of possible components. FIG. 12A illustrates the architecture of identifiers constructed using the MchooseK scheme. Using this method identifiers are constructed by assembling one component form each layer in any subset of all layers (e.g., choose components from k layers out of M possible layers). FIG. 12B illustrates an example of the combinatorial space of identifiers that may be constructed using the MchooseK scheme. In this assembly scheme the combinatorial space may comprise $N^K$MchooseK possible identifiers for M layers, N components per layer, and an identifier length of K components. In an example, if there are five layers each comprising one component, then up to ten distinct identifiers may be assemble comprising two components each.

Figure 12C:
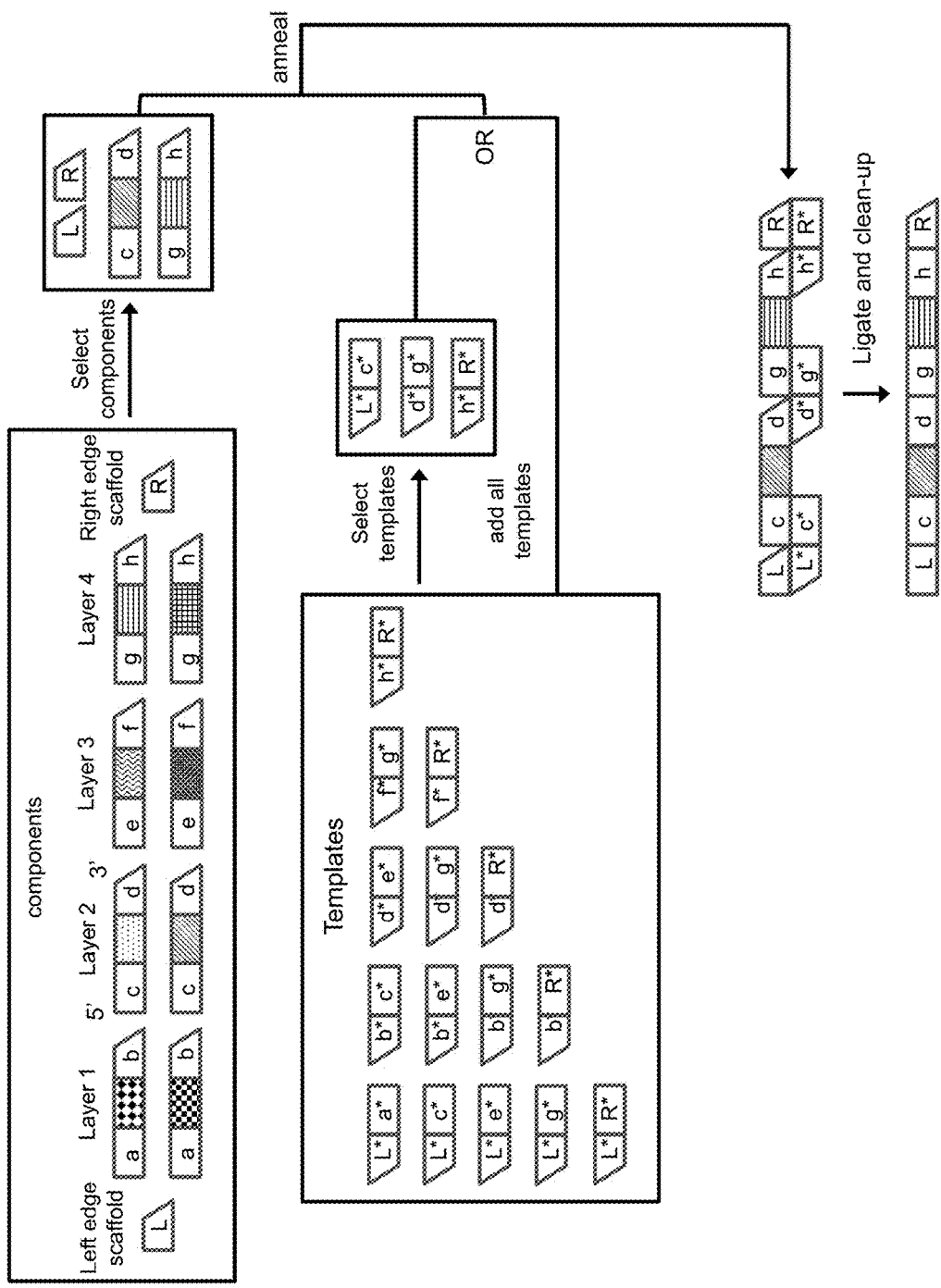
Figure 12D:
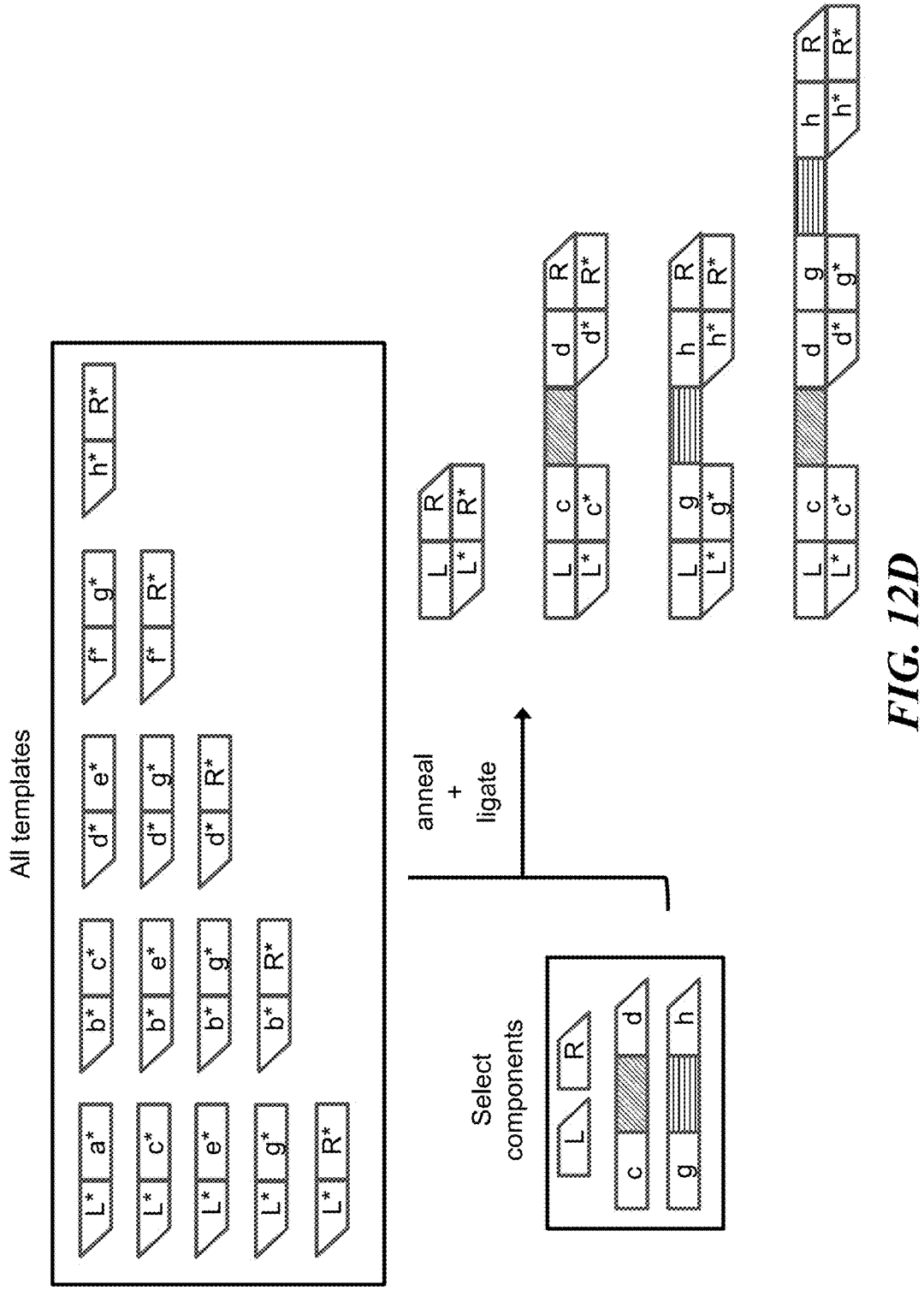

The MchooseK scheme may be implemented using template directed ligation, as shown in FIG. 12C. As with the TDL implementation for the permutation scheme (FIG. 11C), components in this example are assembled between edge scaffolds that may or may not be included in the reaction master mix. Components may be divided into M layers, for example M 4 layers with predefined rank from 2 to M, where the left edge scaffold may be rank 1 and the right edge scaffold may be rank M+1. Templates comprise nucleic acid sequences for the 3' to 5' ligation of any two components with lower rank to higher rank, respectively. There are $((M+1)^2+M+1)/2$ such templates. An individual identifier of any K components from distinct layers may be constructed by combining those selected components in a ligation reaction with the corresponding K+1 staples used to bring the K components together with the edge scaffolds in their rank order. Such a reaction set up may yield the nucleic acid sequence corresponding to the target identifier between the edge scaffolds. Alternatively, a reaction mix comprising all templates may be combined with the select components to assemble the target identifier. This alternative method may generate various nucleic acid sequences with the same edge sequences but distinct lengths (if all component lengths are equal), as illustrated in FIG. 12D. The target identifier (bottom) may be isolated from byproduct nucleic acid sequences by size.

Figure 13A:
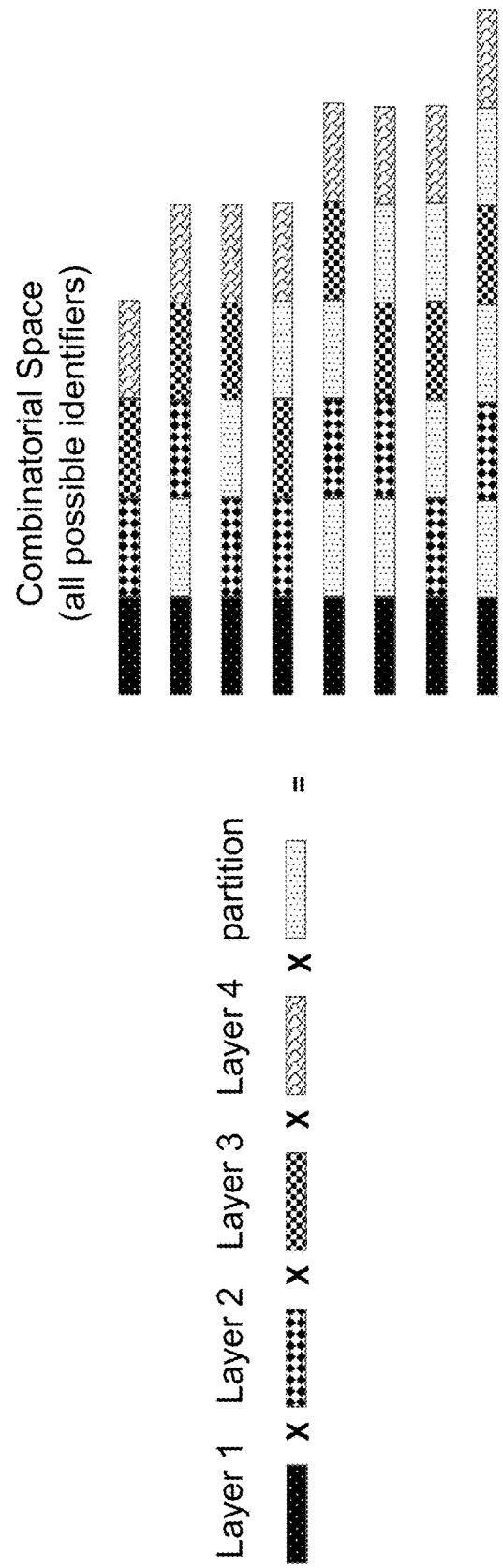
FIGS. 13A and 13B schematically illustrates an example method, referred to as the "partition scheme" for constructing identifiers with partitioned components.
Figure 13B:
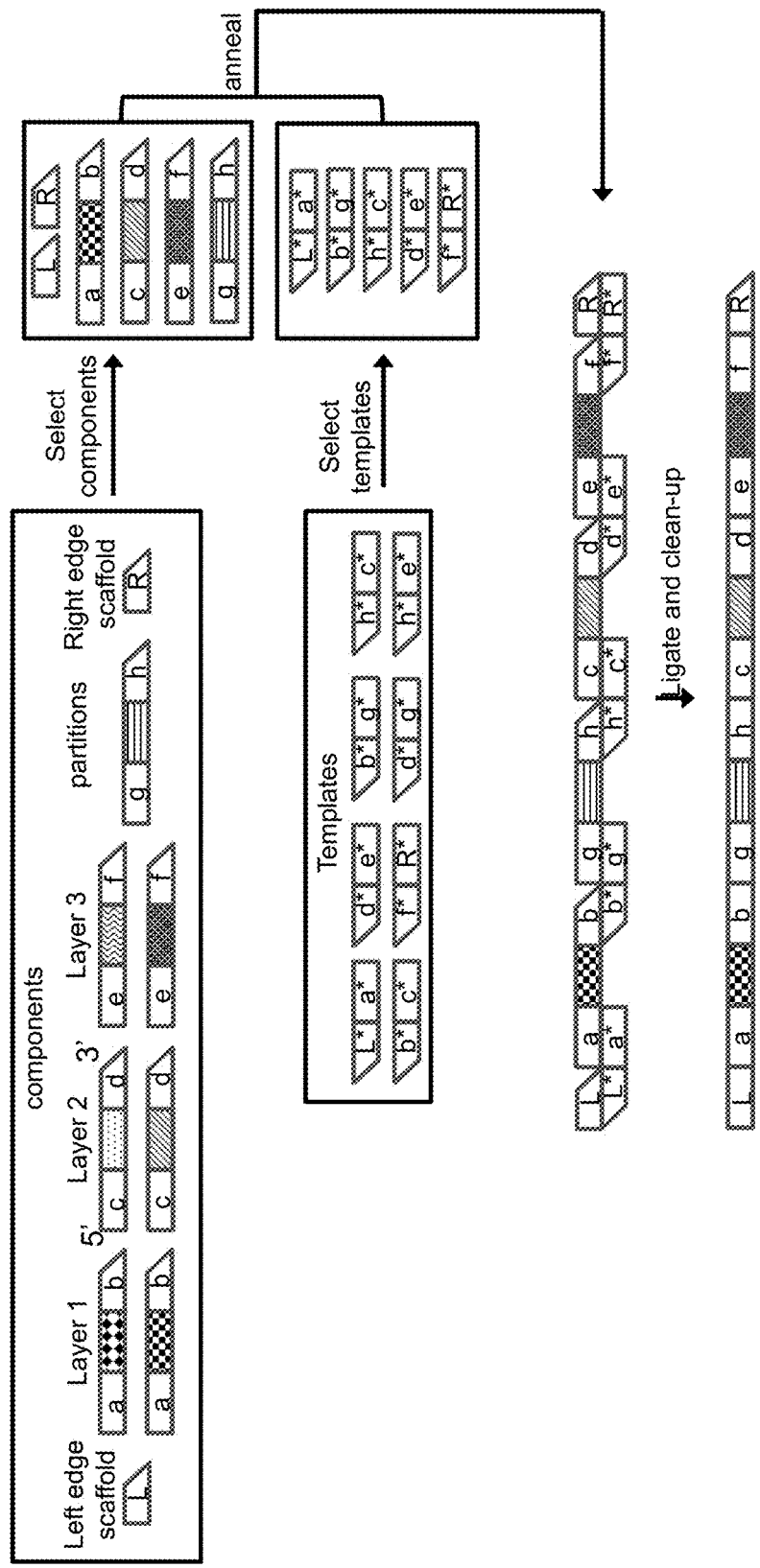

FIGS. 13A and 13B schematically illustrate an example method, referred to as the "partition scheme" for constructing identifiers with partitioned components. FIG. 13A shows an example of the combinatorial space of identifiers that may be constructed using the partition scheme. An individual identifier may be constructed by assembling one component from each layer in a fixed order with the optional placement of any partition (specially classified component) between any two components of different layers. For example, a set of components may be organized into one partition component and four layers containing one component each. A component from each layer may be combined in a fixed order and a single partition component may be assembled in various locations between layers. An identifier in this combinatorial space may comprise no partition components, a partition component between the components from the first and second layer, a partition between the components from the second and third layer, and so on to make a combinatorial space of eight possible identifiers. In general, with M layers, each with N components, and p partition components, there are $N^K (p+1)^{M-1}$ possible identifiers that may be constructed. This method may generate identifiers of various lengths.

FIG. 13B shows an example implementation of the partition scheme using template directed ligation. Templates comprise nucleic acid sequences for ligating together one component from each of M layers in a fixed order. For each partition component, additional pairs of templates exist that enable the partition component to ligate in between the components from any two adjacent layers. For example a pair of templates such that one template (with sequence g*b* (5' to 3') for example) in a pair enables the 3' end of layer 1 (with sequence b) to ligate to the 5' end of the partition component (with sequence g) and such that the second template in the pair (with sequence c*h* (5' to 3') for example) enables the 3' end of the partition component (with sequence h) to ligate to the 5' end of layer 2 (with sequence c). To insert a partition between any two components of adjacent layers, the standard template for ligating together those layers may be excluded in the reaction and the pair of templates for ligating the partition in that position may be selected in the reaction. In the current example, targeting the partition component between layer 1 and layer 2 may use the pair of templates c*h* (5' to 3') and g*b* (5' to 3') to select for the reaction rather than the template c*b* (5' to 3'). Components may be assembled between edge scaffolds that may be included in the reaction mix (along with their corresponding templates for ligating to the first and Mth layers, respectively). In general, a total of around M−1+ 2*p*(M−1) selectable templates may be used for this method for M layers and p partition components. This implementation of the partition scheme may generate various nucleic acid sequences in a reaction with the same edge sequences but distinct lengths. The target identifier may be isolated from byproduct nucleic acid sequences by DNA size selection. Specifically, there may be exactly one nucleic acid sequence product with exactly M layer components. If the layer components are designed large enough compared to the partition components, it may be possible to define a universal size selection region whereby the identifier (and none of the non-targeted byproducts) may be selected regardless of the particular partitioning of the components within the identifier, thereby allowing for multiple partitioned identifiers from multiple reactions to be isolated in the same size selection step.

Figure 14A:
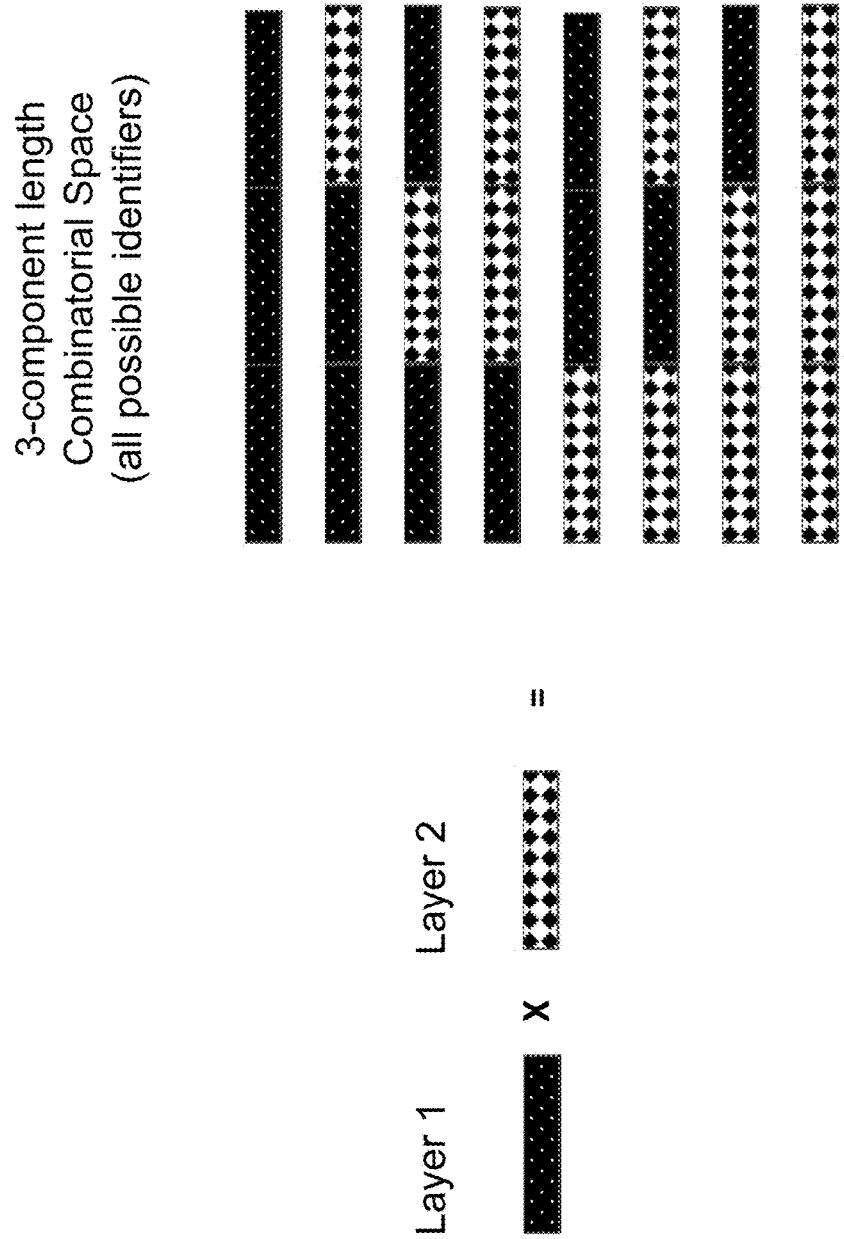
FIGS. 14A and 14B schematically illustrates an example method, referred to as the "unconstrained string" (or USS) scheme, for constructing identifiers made up of any string of components from a number of possible components.
Figure 14B:
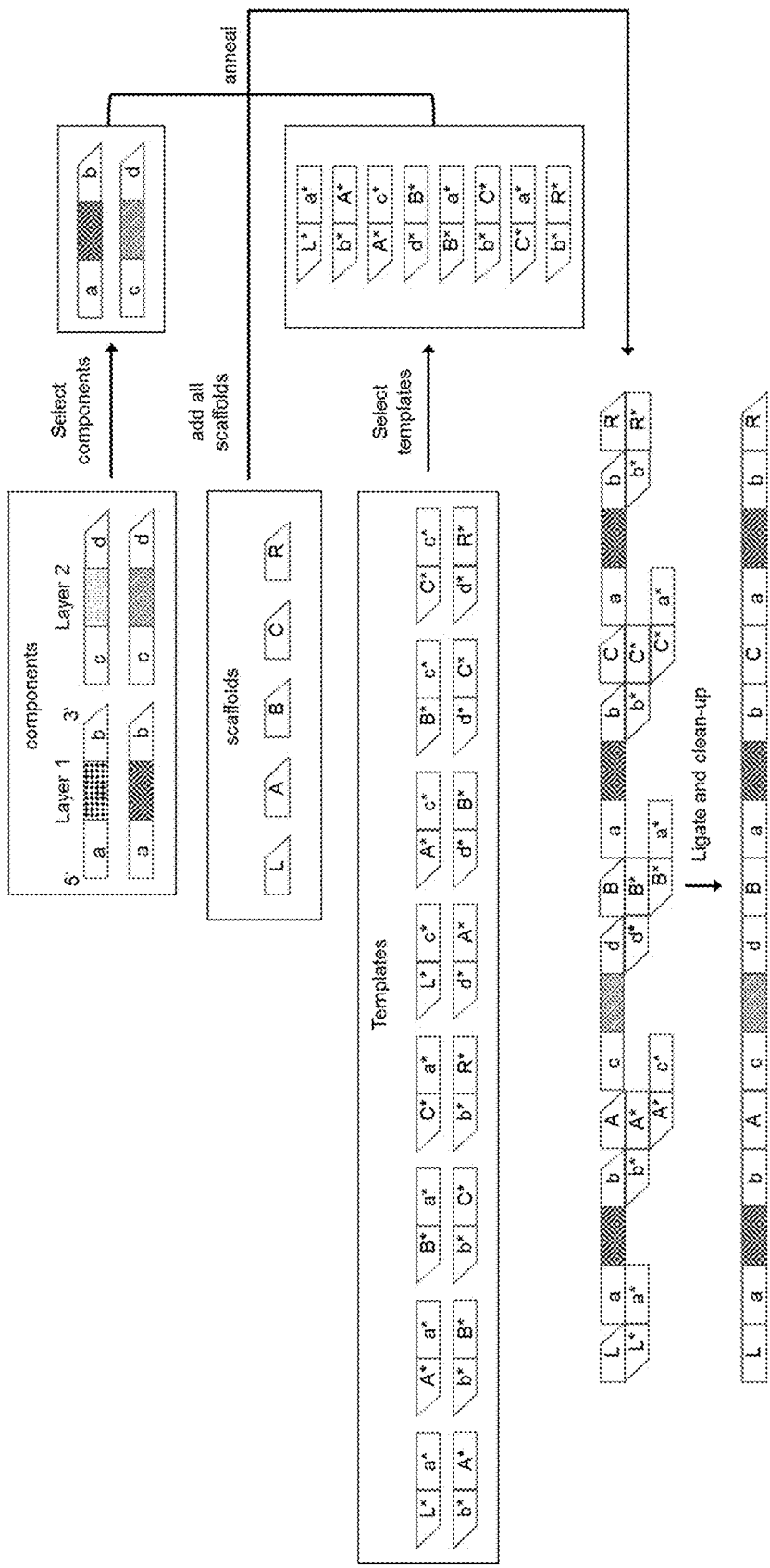

FIGS. 14A and 14B schematically illustrates an example method, referred to as the "unconstrained string scheme" or "USS", for constructing identifiers made up of any string of components from a number of possible components. FIG. 14A shows an example of the combinatorial space of 3-component (or 4-scaffold) length identifiers that may be constructed using the unconstrained string scheme. The unconstrained string scheme constructs an individual identifier of length K components with one or more distinct components each taken from one or more layers, where each distinct component can appear at any of the K component positions in the identifier (allowing for repeats). For example, for two layers, each comprising one component, there are eight possible 3-component length identifiers. In general, with M layers, each with one component, there are $M^K$ possible identifiers of length K components. FIG. 14B shows an example implementation of the unconstrained string scheme using template directed ligation. In this method, K+1 single-stranded and ordered scaffold DNA components (including two edge scaffolds and K−1 internal scaffolds) are present in the reaction mix. An individual identifier comprises a single component ligated between every pair of adjacent scaffolds. For example, a component ligated between scaffolds A and B, a component ligated between scaffolds C and D, and so on until all K adjacent scaffold junctions are occupied by a component. In a reaction, selected components from different layers are introduced to scaffolds along with selected pairs of staples that direct them to assemble onto the appropriate scaffolds. For example, the pair of staples a*L* (5' to 3') and A*b* (5' to 3') direct the layer 1 component with a 5' end region 'a' and 3' end region 'b' to ligate in between the L and A scaffolds. In general, with M layers and K+1 scaffolds, 2*M*K selectable staples may be used to construct any USS identifier of length K Because the staples that connect a component to a scaffold on the 5' end are disjoint from the staples that connect the same component to a scaffold on the 3' end, nucleic acid byproducts may form in the reaction with equal edge scaffolds as the target identifier, but with less than K components (less than K+1 scaffolds) or with more than K components (more than K+1 scaffolds). The targeted identifier may form with exactly K components (K+1 scaffolds) and may therefore be selectable through techniques like DNA size selection if all components are designed to be equal in length and all scaffolds are designed to be equal in length. In certain embodiments of the unconstrained string scheme where there may be one component per layer, that component may solely comprise a single distinct nucleic acid sequence that fulfills all three roles of (1) an identification barcode, (2) a hybridization region for staple-mediated ligation of the 5' end to a scaffold, and (3) a hybridization region for staple mediated ligation of the 3' end to a scaffold.

The internal scaffolds illustrated in FIG. 14B may be designed such that they use the same hybridization sequence for both the staple-mediated 5' ligation of the scaffold to a component and the staple-mediated 3' ligation of the scaffold to another (not necessarily distinct) component. Thus the depicted one-scaffold, two-staple stacked hybridization events in FIG. 14B represent the statistical back-and-forth hybridization events that occur between the scaffold and each of the staples, thus enabling both 5' component ligation and 3' component ligation. In other embodiments of the unconstrained string scheme, the scaffold may be designed with two concatenated hybridization regions—a distinct 3' hybridization region for staple-mediated 3' ligation and a distinct 5' hybridization region for staple-mediated 5' ligation.

Figure 15A:
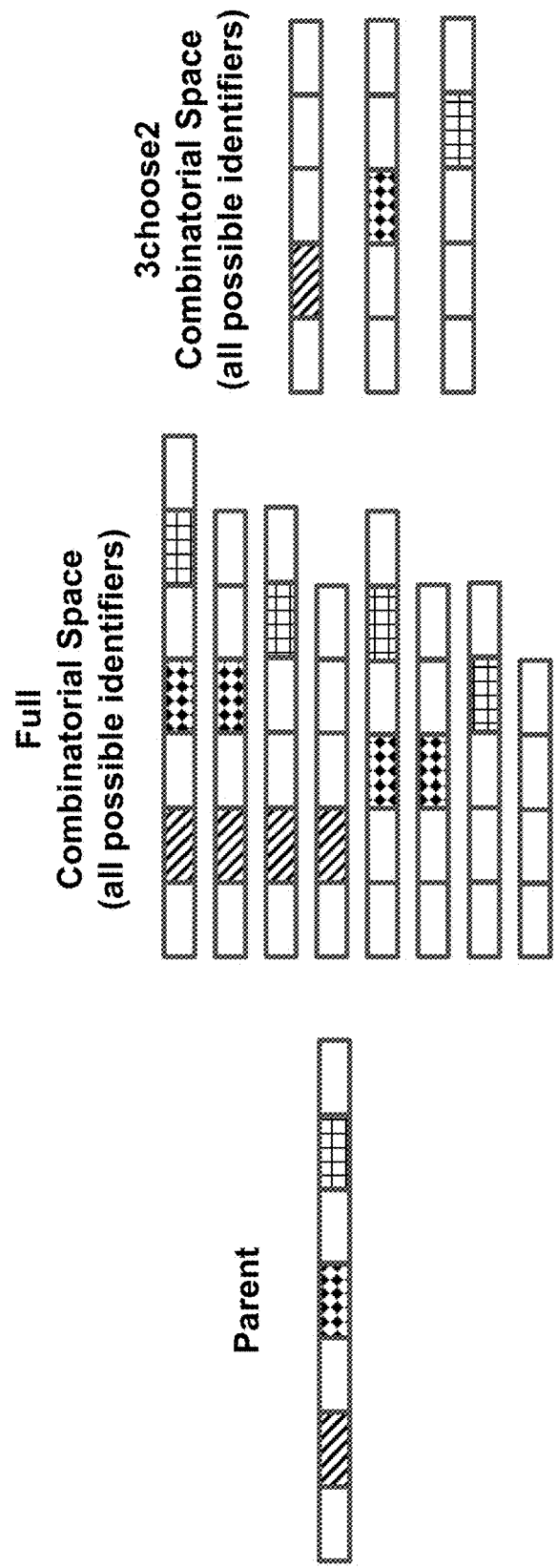
FIGS. 15A and 15B schematically illustrates an example method, referred to as "component deletion" for constructing identifiers by removing components from a parent identifier.
Figure 15B:
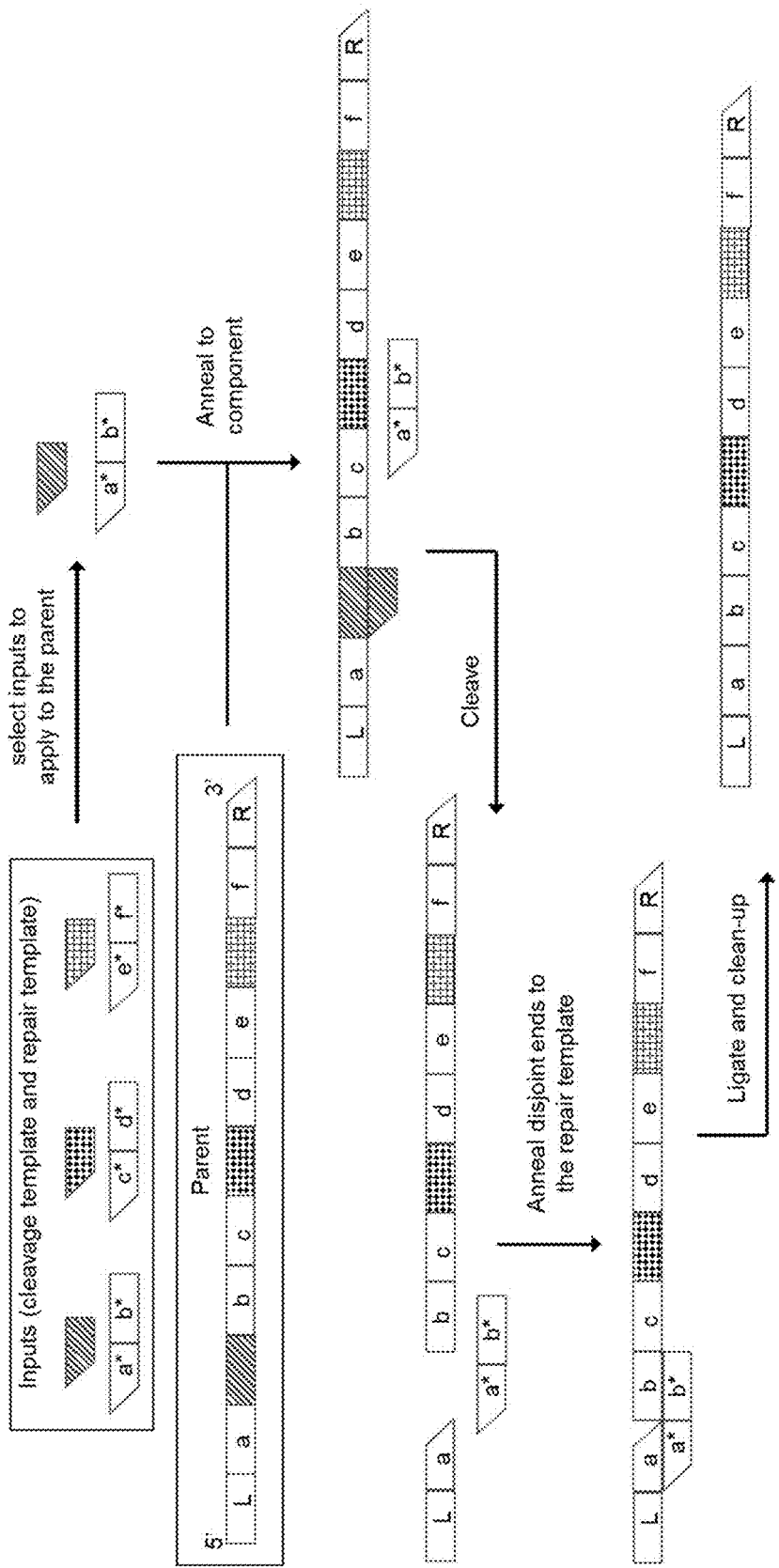

FIGS. 15A and 15B schematically illustrate an example method, referred to as the "component deletion scheme", for constructing identifiers by deleting nucleic acid sequences (or components) from a parent identifier. FIG. 15A shows an example of the combinatorial spaces of possible identifiers that may be constructed using the component deletion scheme. In this example, a parent identifier may comprise multiple components. A parent identifier may comprise more than or equal to about 2, 3, 4, 5, 6, 7, 8, 9, 10, 20, 30, 40, 50 or more components. An individual identifier may be constructed by selectively deleting any number of components from N possible components, leading to a "full" combinatorial space of size $2^N$, or by deleting a fixed number of K components from N possible components, thus leading to an "NchooseK" combinatorial space of size NchooseK. In an example with a parent identifier with 3 components, the full combinatorial space may be 8 and the 3choose2 combinatorial space may be 3.

FIG. 15B shows an example implementation of the component deletion scheme using double stranded targeted cleavage and repair (DSTCR). The parent sequence may be a single stranded DNA substrate comprising components flanked by nuclease-specific target sites (which can be 4 or less bases in length), and where the parent may be incubated with one or more double-strand-specific nucleases corresponding to the target sites. An individual component may be targeted for deletion with a complementary single stranded DNA (or cleavage template) that binds the component DNA (and flanking nuclease sites) on the parent, thus forming a stable double stranded sequence on the parent that may be cleaved on both ends by the nucleases. Another single stranded DNA (or repair template) hybridizes to the resulting disjoint ends of the parent (between which the component sequence had been) and brings them together for ligation, either directly or bridged by a replacement sequence, such that the ligated sequences on the parent no longer contain active nuclease-targeted sites. We refer to this method as "Double Stranded Targeted Cleavage" (DSTC). Size selection may be used to select for identifiers with a certain number of deleted components.

Alternatively, or in addition to, the parent identifier may be a double or single stranded nucleic acid substrate comprising components separated by spacer sequences such that no two components are flanked by the same sequence. The parent identifier may be incubated with Cas9 nuclease. An individual component may be targeted for deletion with guide ribonucleic acids (the cleavage templates) that bind to the edges of the component and enable Cas9-mediated cleavage at its flanking sites. A single stranded nucleic acid (the repair template) may hybridize to the resulting disjoint ends of the parent identifier (e.g., between the ends where the component sequence had been), thus bringing them together for ligation. Ligation may be done directly or by bridging the ends with a replacement sequence, such that the ligated sequences on the parent no longer contain spacer sequences that can be targeted by Cas9. We refer to this method as "sequence specific targeted cleavage and repair" or "SSTCR".

Identifiers may be constructed by inserting components into a parent identifier using a derivative of DSTCR. A parent identifier may be single stranded nucleic acid substrate comprising nuclease-specific target sites (which can be 4 or less bases in length), each embedded within a distinct nucleic acid sequence. The parent identifier may be incubated with one or more double-strand-specific nucleases corresponding to the target sites. An individual target site on the parent identifier may be targeted for component insertion with a complementary single stranded nucleic acid (the cleavage template) that binds the target site and the distinct surrounding nucleic acid sequence on the parent identifier, thus forming a double stranded site. The double-stranded site may be cleaved by a nuclease. Another single stranded nucleic acid (the repair template) may hybridize to the resulting disjoint ends of the parent identifier and bring them together for ligation, bridged by a component sequence, such that the ligated sequences on the parent no longer contain active nuclease-targeted sites. Alternatively a derivative of SSTCR may be used to insert components into a parent identifier. The parent identifier may be a double or single-stranded nucleic acid and the parent may be incubated with a Cas9 nuclease. A distinct site on the parent identifier may be targeted for cleavage with a guide RNA (the cleavage template). A single stranded nucleic acid (the repair template) may hybridize to the disjoint ends of the parent identifier and bring them together for ligation, bridged by a component sequence, such that the ligated sequences on the parent identifier no longer contain active nuclease-targeted sites. Size selection may be used to select for identifiers with a certain number of component insertions.

Figure 16:
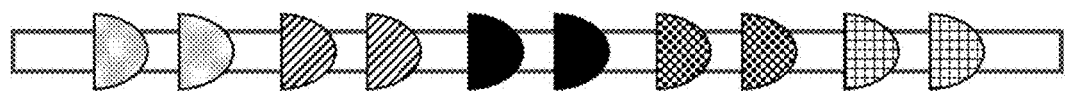
FIG. 16 schematically illustrates a parent identifier with recombinase recognition sites where further identifiers may be constructed by applying recombinases to the parent identifier.

FIG. 16 schematically illustrates a parent identifier with recombinase recognition sites. Recognition sites of different patterns can be recognized by different recombinases. All recognition sites for a given set of recombinases are arranged such that the nucleic acids in between them may be excised if the recombinase is applied. The nucleic acid strand shown in FIG. 16 can adopt $2^5=32$ different sequences depending on the subset of recombinases that are applied to it. In some embodiments, as depicted in FIG. 16, unique molecules can be generated using recombinases to excise, shift, invert, and transpose segments of DNA to create different nucleic acid molecules. In general, with N recombinases there can be $2^N$ possible identifiers built from a parent. In some embodiments, multiple orthogonal pairs of recognition sites from different recombinases may be arranged on a parent identifier in an overlapping fashion such that the application of one recombinase affects the type of recombination event that occurs when a downstream recombinase is applied (see Roquet et al., Synthetic recombinase-based state machines in living cells, Science 353 (6297): aad8559 (2016), which is entirely incorporated herein by reference). Such a system may be capable of constructing a different identifier for every ordering of N recombinases, N!. Recombinases may be of the tyrosine family such as Flp and Cre, or of the large serine recombinase family such as PhiC31, BxbI, TP901, or A118. The use of recombinases from the large serine recombinase family may be advantageous because they facilitate irreversible recombination and therefore may produce identifiers more efficiently than other recombinases.

In some instances, a single nucleic acid sequence can be programmed to become many distinct nucleic acid sequences by applying numerous recombinases in a distinct order. Approximately ~$e^1$M! distinct nucleic acid sequences may be generated by applying M recombinases in different subsets and orders thereof, when the number of recombinases, M, may be less than or equal to 7 for the large serine recombinase family. When the number of recombinases, M, may be greater than 7, the number of sequences that can be produced approximates $3.9^M$, see e.g., Roquet et al., Synthetic recombinase-based state machines in living cells, Science 353 (6297): aad8559 (2016), which is entirely incorporated herein by reference. Additional methods for producing different DNA sequences from one common sequence can include targeted nucleic acid editing enzymes such as CRISPR-Cas, TALENS, and Zinc Finger Nucleases. Sequences produced by recombinases, targeted editing enzymes or the like can be used in conjunction with any of the previous methods, for example methods disclosed in any of the figures and disclosure in the present application.

If the bit-stream of information to be encoded is larger than that which can be encoded by any single nucleic acid molecule, then the information can be split and indexed with nucleic acid sequence barcodes. Moreover, any subset of size k nucleic acid molecules from the set of N nucleic acid molecules can be chosen to produce $\log_2$(Nchoosek) bits of information. Barcodes may be assembled onto the nucleic acid molecules within the subsets of size k to encode even longer bit streams. For example, M barcodes may be used to produce M*$\log_2$(Nchoosek) bits of information. Given a number, N, of available nucleic acid molecules in a set and a number, M, of available barcodes, subsets of size k=$k_0$ may be chosen to minimize the total number of molecules in a pool to encode a piece of information. A method for encoding digital information can comprise steps for breaking up the bit stream and encoding the individual elements. For example, a bit stream comprising 6 bits can be split into 3 components each component comprising two bits. Each two bit component can be barcoded to form an information cassette, and grouped or pooled together to form a hyper-pool of information cassettes.

Barcodes can facilitate information indexing when the amount of digital information to be encoded exceeds the amount that can fit in one pool alone. Information comprising longer strings of bits and/or multiple bytes can be encoded by layering the approach disclosed in FIG. 3, for example, by including a tag with unique nucleic acid sequences encoded using the nucleic acid index. Information cassettes or identifier libraries can comprise nitrogenous bases or nucleic acid sequences that include unique nucleic acid sequences that provide location and bit-value information in addition to a barcode or tag which indicates the component or components of the bit stream that a given sequence corresponds to. Information cassettes can comprise one or more unique nucleic acid sequences as well as a barcode or tag. The barcode or tag on the information cassette can provide a reference for the information cassette and any sequences included in the information cassette. For example, the tag or barcode on an information cassette can indicate which portion of the bit stream or bit component of the bit steam the unique sequence encodes information for (e.g., the bit value and bit position information for).

Using barcodes, more information in bits can be encoded in a pool than the size of the combinatorial space of possible identifiers. A sequence of 10 bits, for example, can be separated into two sets of bytes, each byte comprising 5 bits. Each byte can be mapped to a set of 5 possible distinct identifiers. Initially, the identifiers generated for each byte can be the same, but they may be kept in separate pools or else someone reading the information may not be able to tell which byte a particular nucleic acid sequence belongs to. However each identifier can be barcoded or tagged with a label that corresponds to the byte for which the encoded information applies (e.g., barcode one may be attached to sequences in the nucleic acid pool to provide the first five bits and barcode two may be attached to sequences in the nucleic acid pool to provide the second five bits), and then the identifiers corresponding to the two bytes can be combined into one pool (e.g., "hyper-pool" or one or more identifier libraries). Each identifier library of the one or more combined identifier libraries may comprise a distinct barcode that identifies a given identifier as belonging to a given identifier library. Methods for adding a barcode to each identifier in an identifier library can comprise using PCR, Gibson, ligation, or any other approach that enables a given barcode (e.g., barcode 1) to attach to a given nucleic acid sample pool (e.g., barcode 1 to nucleic acid sample pool 1 and barcode 2 to nucleic acid sample pool 2). The sample from the hyper-pool can be read with sequencing methods, and sequencing information can be parsed using the barcode or tag. A method using identifier libraries and barcodes with a set of M barcodes and N possible identifiers (the combinatorial space) can encode a stream of bits with a length equivalent to the product of M and N.

In some embodiments, identifier libraries may be stored in an array of wells. The array of wells may be defined as having n columns and q rows and each well may comprise two or more identifier libraries in a hyper-pool. The information encoded in each well may constitute one large contiguous item of information of size n×q larger than the information contained in each of the wells. An aliquot may be taken from one or more of the wells in the array of wells and the encoding may be read using sequencing, hybridization, or PCR.

A nucleic acid sample pool, hyper-pool, identifier library, group of identifier libraries, or a well, containing a nucleic acid sample pool or hyper-pool may comprise unique nucleic acid molecules (e.g., identifiers) corresponding to bits of information and a plurality of supplemental nucleic acid sequences. The supplemental nucleic acid sequences may not correspond to encoded data (e.g., do not correspond to a bit value). The supplemental nucleic acid samples may mask or encrypt the information stored in the sample pool. The supplemental nucleic acid sequences may be derived from a biological source or synthetically produced. Supplemental nucleic acid sequences derived from a biological source may include randomly fragmented nucleic acid sequences or rationally fragmented sequences. The biologically derived supplemental nucleic acids may hide or obscure the data-containing nucleic acids within the sample pool by providing natural genetic information along with the synthetically encoded information, especially if the synthetically encoded information (e.g., the combinatorial space of identifiers) is made to resemble natural genetic information (e.g., a fragmented genome). In an example, the identifiers are derived from a biological source and the supplemental nucleic acids are derived from a biological source. A sample pool may contain multiple sets of identifiers and supplemental nucleic acid sequences. Each set of identifiers and supplemental nucleic acid sequences may be derived from different organisms. In an example, the identifiers are derived from one or more organisms and the supplemental nucleic acid sequences are derived from a single, different organism. The supplemental nucleic acid sequences may also be derived from one or more organism and the identifiers may be derived from a single organism that is different from the organism that the supplemental nucleic acids are derived from. Both the identifiers and the supplemental nucleic acid sequences may be derived from multiple different organisms. A key may be used to distinguish the identifiers from the supplemental nucleic acid sequences.

The supplemental nucleic acid sequences may store metadata about the written information. The metadata may comprise extra information for determining and/or authorizing the source of the original information and or the intended recipient of the original information. The metadata may comprise extra information about the format of the original information, the instruments and methods used to encode and write the original information, and the date and time of writing the original information into the identifiers. The metadata may comprise additional information about the format of the original information, the instruments and methods used to encode and write the original information, and the date and time of writing the original information into nucleic acid sequences. The metadata may comprise additional information about modifications made to the original information after writing the information into nucleic acid sequences. The metadata may comprise annotations to the original information or one or more references to external information. Alternatively, or in addition to, the metadata may be stored in one or more barcodes or tags attached to the identifiers.

The identifiers in an identifier pool may have the same, similar, or different lengths than one another. The supplemental nucleic acid sequences may have a length that is less than, substantially equal to, or greater than the length of the identifiers. The supplemental nucleic acid sequences may have an average length that is within one base, within two bases, within three bases, within four bases, within five bases, within six bases, within seven bases, within eight bases, within nine bases, within ten bases, or within more bases of the average length of the identifiers. In an example, the supplemental nucleic acid sequences are the same or substantially the same length as the identifiers. The concentration of supplemental nucleic acid sequences may be less than, substantially equal to, or greater than the concentration of the identifiers in the identifiers library. The concentration of the supplemental nucleic acids may be less than or equal to about 1%, 10%, 20%, 40%, 60%, 80%, 100, %, 125%, 150%, 175%, 200%, 1000%, $1\times10^4$%, $1\times10^5$%, $1\times10^6$%, $1\times10^7$%, $1\times10^8$% or less than the concentration of the identifiers. The concentration of the supplemental nucleic acids may be greater than or equal to about 1%, 10%, 20%, 40%, 60%, 80%, 100, %, 125%, 150%, 175%, 200%, 1000%, $1\times10^4$%, $1\times10^5$%, $1\times10^6$%, $1\times10^7$%, $1\times10^8$% or more than the concentration of the identifiers. Larger concentrations may be beneficial for obfuscation or concealing data. In an example, the concentration of the supplemental nucleic acid sequences are substantially greater (e.g., $1\times10^8$% greater) than the concentration of identifiers in an identifier pool.

Methods for Copying and Accessing Data Stored in Nucleic Acid Sequences

In another aspect, the present disclosure provides methods for copying information encoded in nucleic acid sequence(s). A method for copying information encoded in nucleic acid sequence(s) may comprise (a) providing an identifier library and (b) constructing one or more copies of the identifier library. An identifier library may comprise a subset of a plurality of identifiers from a larger combinatorial space. Each individual identifier of the plurality of identifiers may correspond to an individual symbol in a string of symbols. An identifier may comprise one or more components. A component may comprise a nucleic acid sequence.

In another aspect, the present disclosure provides methods for accessing information encoded in nucleic acid sequences. A method for accessing information encoded in nucleic acid sequences may comprise (a) providing an identifier library, and (b) extracting a portion or a subset of the identifiers present in the identifier library from the identifier library. An identifier library may comprise a subset of a plurality of identifiers from a larger combinatorial space. Each individual identifier of the plurality of identifiers may correspond to an individual symbol in a string of symbols. An identifier may comprise one or more components. A component may comprise a nucleic acid sequence.

Information may be written into one or more identifier libraries as described elsewhere herein. Identifiers may be constructed using any method described elsewhere herein. Stored data may be copied by generating copies of the individual identifiers in an identifier library or in one or more identifier libraries. A portion of the identifiers may be copied or an entire library may be copied. Copying may be performed by amplifying the identifiers in an identifier library. When one or more identifier libraries are combined, a single identifier library or multiple identifier libraries may be copied. If an identifier library comprises supplemental nucleic acid sequences, the supplemental nucleic acid sequences may or may not be copied.

Identifiers in an identifier library may be constructed to comprise one or more common primer binding sites. The one or more binding sites may be located at the edges of each identifier or interweaved throughout each identifier. The primer binding site may allow for an identifier library specific primer pair or a universal primer pair to bind to and amplify the identifiers. All the identifiers within an identifier library or all the identifiers in one or more identifier libraries may be replicated multiple times by multiple PCR cycles. Conventional PCR may be used to copy the identifiers and the identifiers may be exponentially replicated with each PCR cycle. The number of copies of an identifier may increase exponentially with each PCR cycle. Linear PCR may be used to copy the identifiers and the identifiers may be linearly replicated with each PCR cycle. The number of identifier copies may increase linearly with each PCR cycle. The identifiers may be ligated into a circular vector prior to PCR amplification. The circle vector may comprise a barcode at each end of the identifier insertion site. The PCR primers for amplifying identifiers may be designed to prime to the vector such that the barcoded edges are included with the identifier in the amplification product. During amplification, recombination between identifiers may result in copied identifiers that comprise non-correlated barcodes on each edge. The non-correlated barcodes may be detectable upon reading the identifiers. Identifiers containing non-correlated barcodes may be considered false positives and may be disregarded during the information decoding process.

Information may be encoded by assigning each bit of information to a unique nucleic acid molecule. For example, three sample sets (X, Y, and Z) each containing two nucleic acid sequences may assemble into eight unique nucleic acid molecules and encode eight bits of data:

N1=X1Y1Z1
N2=X1Y1Z2
N3=X1Y2Z1
N4=X1Y2Z2
N5=X2Y1Z1
N6=X2Y1Z2
N7=X2Y2Z1
N8=X2Y2Z2

Each bit in a string may then be assigned to the corresponding nucleic acid molecule (e.g., N1 may specify the first bit, N2 may specify the second bit, N3 may specify the third bit, and so forth). The entire bit string may be assigned to a combination of nucleic acid molecules where the nucleic acid molecules corresponding to bit-values of '1' are included in the combination or pool. For example, in UTF-8 codings, the letter 'K' may be represented by the 8-bit string code 01001011 which may be encoded by the presence of four nucleic acid molecules (e.g., X1Y1Z2, X2Y1Z1, X2Y2Z1, and X2Y2Z2 in the above example).

The information may be accessed through sequencing or hybridization assays. For example, primers or probes may be designed to bind to common regions or the barcoded region of the nucleic acid sequence. This may enable amplification of any region of the nucleic acid molecule. The amplification product may then be read by sequencing the amplification product or by a hybridization assay. In the above example encoding the letter 'K', if the first half of the data is of interest a primer specific to the barcode region of the X1 nucleic acid sequence and a primer that binds to the common region of the Z set may be used to amplify the nucleic acid molecules. This may return the sequence Y1Z2, which may encode for 0100. The substring of that data may also be accessed by further amplifying the nucleic acid molecules with a primer that binds to the barcode region of the Y1 nucleic acid sequence and a primer that binds to the common sequence of the Z set. This may return the Z2 nucleic acid sequence, encoding the substring 01. Alternatively, the data may be accessed by checking for the presence or absence of a particular nucleic acid sequence without sequencing. For example, amplification with a primer specific to the Y2 barcode may generate amplification products for the Y2 barcode, but not for the Y1 barcode. The presence of Y2 amplification product may signal a bit value of '1'. Alternatively, the absence of Y2 amplification products may signal a bit value of '0'.

PCR based methods can be used to access and copy data from identifier or nucleic acid sample pools. Using common primer binding sites that flank the identifiers in the pools or hyper-pools, nucleic acids containing information can be readily copied. Alternatively, other nucleic acid amplification approaches such as isothermal amplification may also be used to readily copy data from sample pools or hyper-pools (e.g., identifier libraries). In instances where the sample comprises hyper-pools, a particular subset of information (e.g., all nucleic acids relating to a particular barcode) can be accessed and retrieved by using a primer that binds the specific barcode at one edge of the identifier in the forward orientation, along with another primer that binds a common sequence on the opposite edge of the identifier in a reverse orientation. Various read-out methods can be used to pull information from the encoded nucleic acid; for example microarray (or any sort of fluorescent hybridization), digital PCR, quantitative PCR (qPCR), and various sequencing platforms can be further used to read out the encoded sequences and by extension digitally encoded data.

Figure 17A:
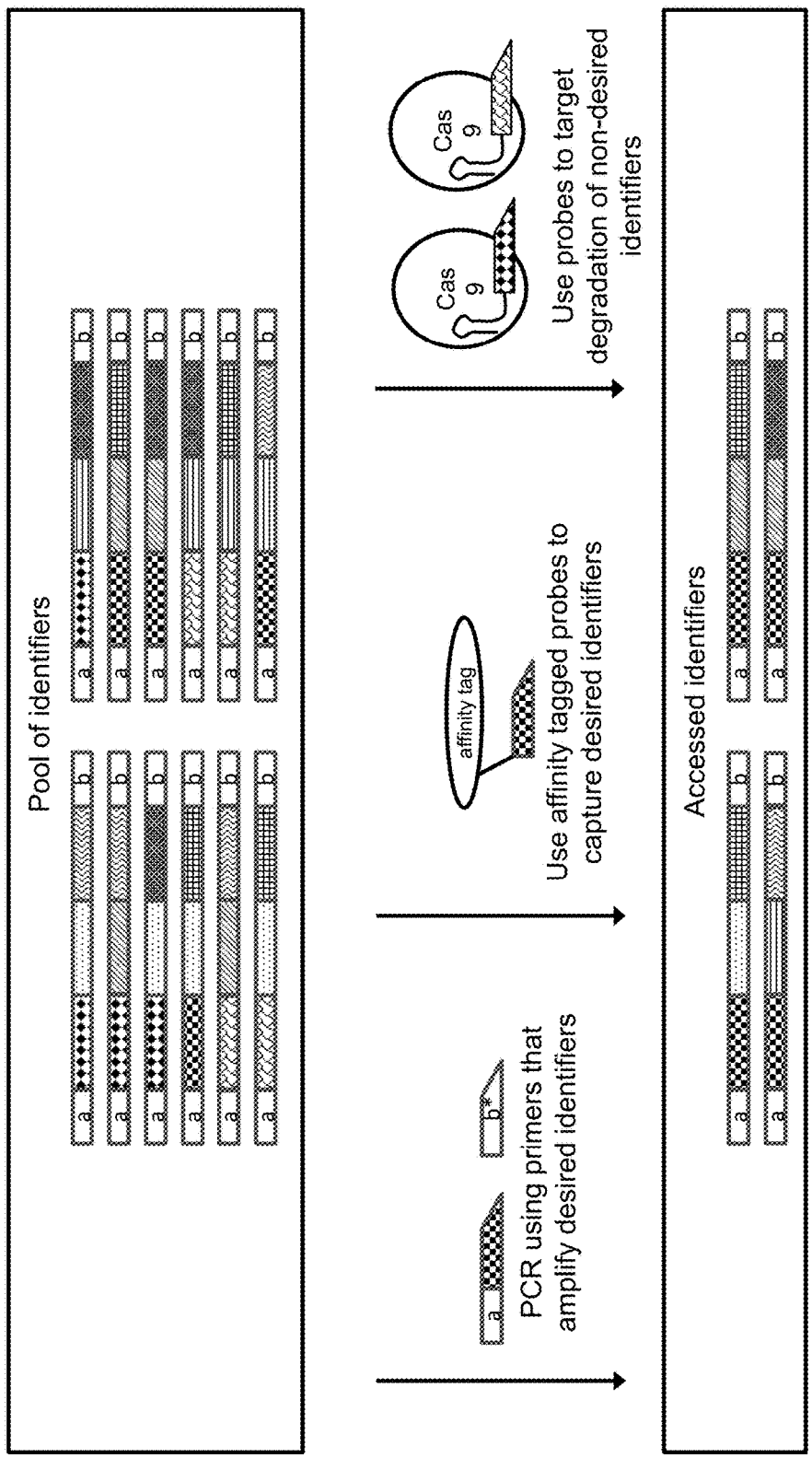
FIGS. 17A-17C schematically illustrate an overview of example methods for accessing portions of information stored in nucleic acid sequences by accessing a number of particular identifiers from a larger number of identifiers.
Figure 17B:
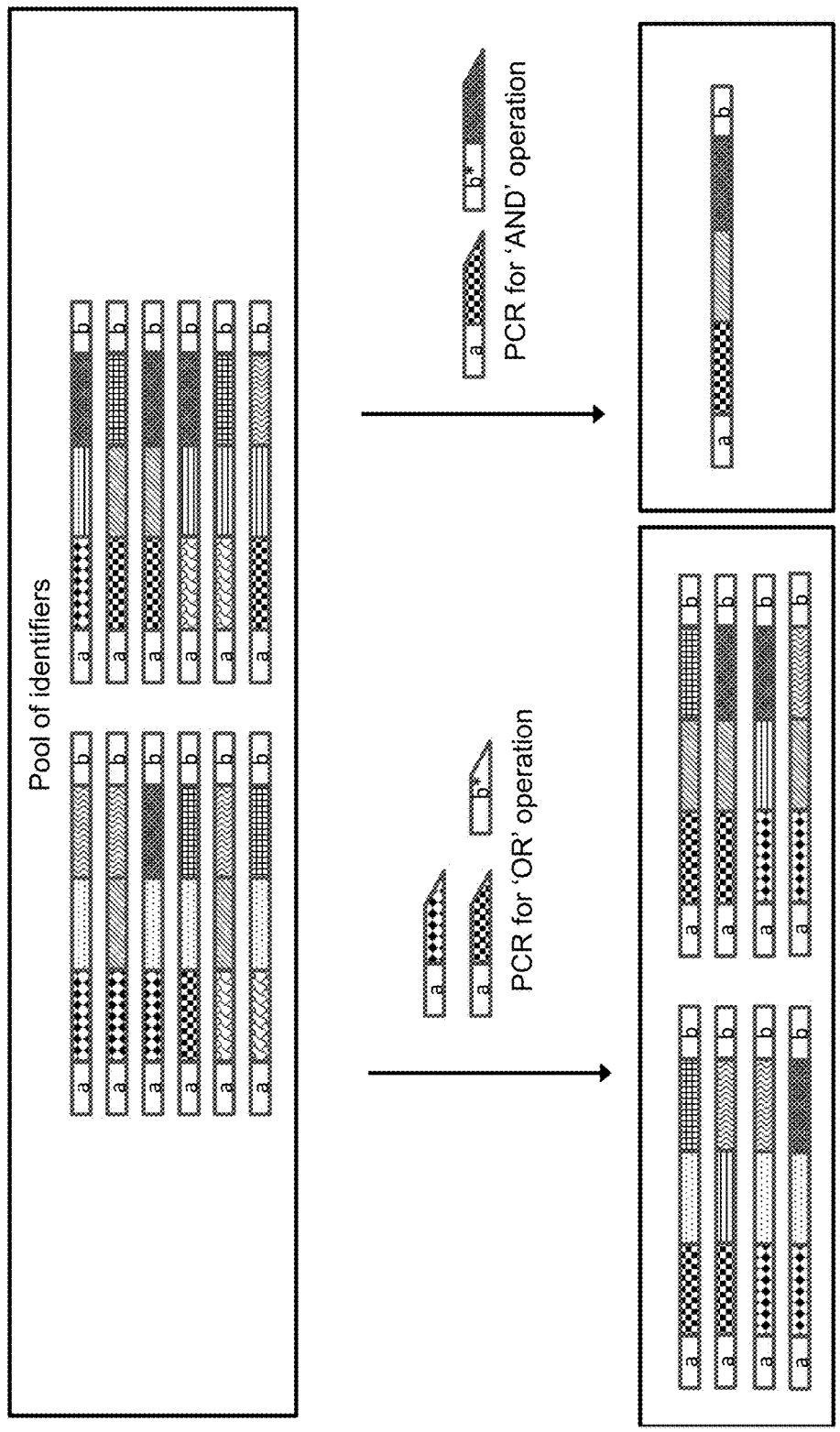
Figure 17C:
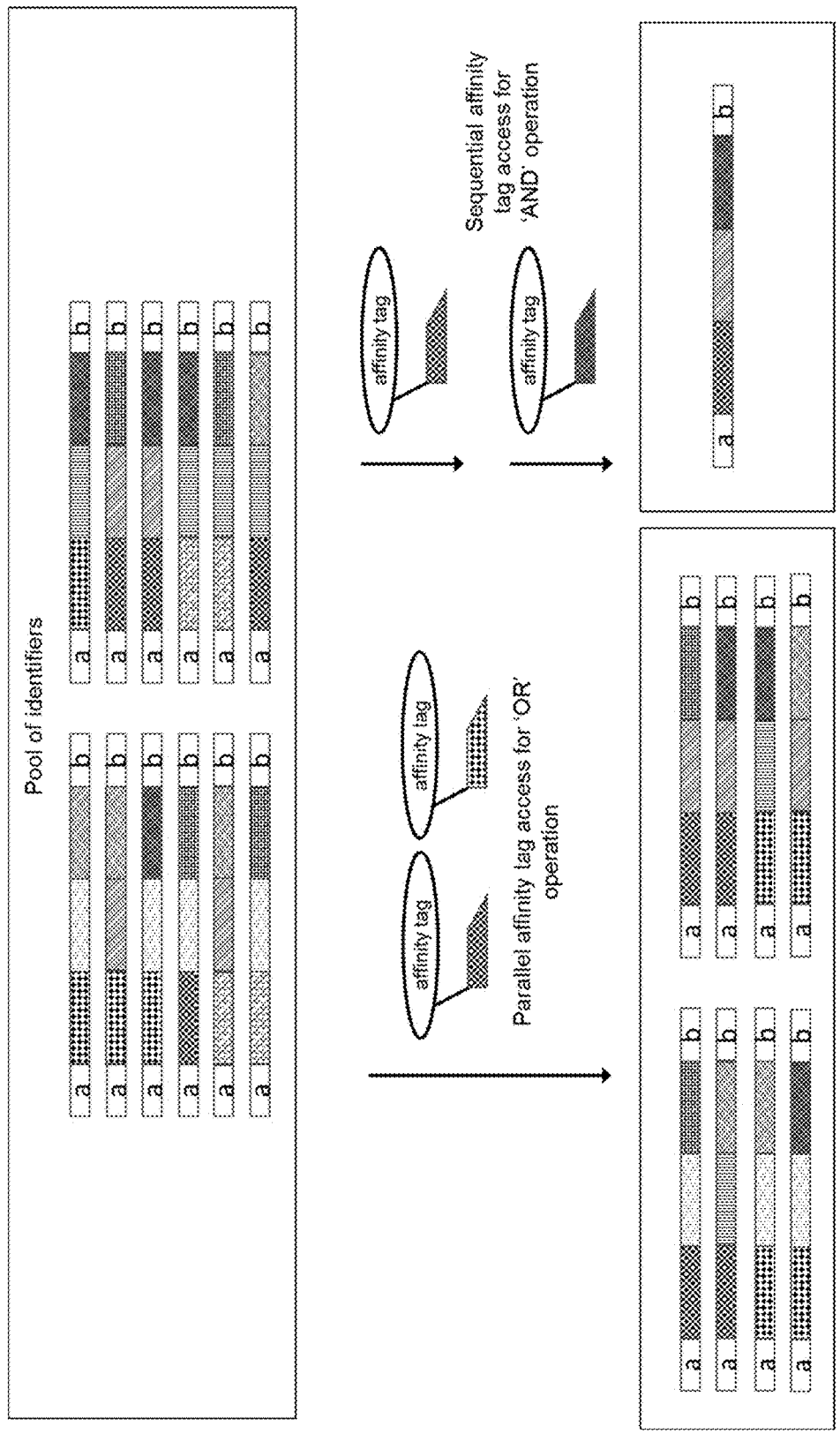

Accessing information stored in nucleic acid molecules (e.g., identifiers) may be performed by selectively removing the portion of non-targeted identifiers from an identifier library or a pool of identifiers or, for example, selectively removing all identifiers of an identifier library from a pool of multiple identifier libraries. Accessing data may also be performed by selectively capturing targeted identifiers from an identifier library or pool of identifiers. The targeted identifiers may correspond to data of interest within the larger item of information. A pool of identifiers may comprise supplemental nucleic acid molecules. The supplemental nucleic acid molecules may contain metadata about the encoded information or may be used to encrypt or mask the identifiers corresponding to the information. The supplemental nucleic acid molecules may or may not be extracted while accessing the targeted identifiers. FIGS. 17A-17C schematically illustrate an overview of example methods for accessing portions of information stored in nucleic acid sequences by accessing a number of particular identifiers from a larger number of identifiers. FIG. 17A shows example methods for using polymerase chain reaction, affinity tagged probes, and degradation targeting probes to access identifiers containing a specified component. For PCR-based access, a pool of identifiers (e.g., identifier library) may comprise identifiers with a common sequence at each end, a variable sequence at each end, or one of a common sequence or a variable sequence at each end. The common sequences or variable sequences may be primer binding sites. One or more primers may bind to the common or variable regions on the identifier edges. The identifiers with primers bound may be amplified by PCR. The amplified identifiers may significantly outnumber the non-amplified identifiers. During reading, the amplified identifiers may be identified. An identifier from an identifier library may comprise sequences on one or both of its ends that are distinct to that library, thus enabling a single library to be selectively accessed from a pool or group of more than one identifier libraries.

For affinity-tag based access, the components that constitute the identifiers in a pool may share complementarity with one or more probes. The one or more probes may bind or hybridize to the identifiers to be accessed. The probe may comprise an affinity tag. The affinity tags may bind to a bead, generating a complex comprising a bead, at least one probe, and at least one identifier. The beads may be magnetic, and together with a magnet, the beads may collect and isolate the identifiers to be accessed. The identifiers may be removed from the beads under denaturing conditions prior to reading. Alternatively, or in addition to, the beads may collect the non-targeted identifiers and sequester them away from the rest of the pool that can get washed into a separate vessel and read. The affinity tag may bind to a column. The identifiers to be accessed may bind to the column for capture. Column-bound identifiers may subsequently be eluted or denatured from the column prior to reading. Alternatively, the non-targeted identifiers may be selectively targeted to the column while the targeted identifiers may flow through the column. Accessing the targeted identifiers may comprise applying one or more probes to a pool of identifiers simultaneously or applying one or more probes to a pool of identifiers sequentially.

For degradation based access, the components that constitute the identifiers in a pool may share complementarity with one or more degradation-targeting probes. The probes may bind to or hybridize with distinct components on the identifiers. The probe may be a target for a degradation enzyme, such as an endonuclease. In an example, one or more identifier libraries may be combined. A set of probes may hybridize with one of the identifier libraries. The set of probes may comprise RNA and the RNA may guide a Cas9 enzyme. A Cas9 enzyme may be introduced to the one or more identifier libraries. The identifiers hybridized with the probes may be degraded by the Cas9 enzyme. The identifiers to be accessed may not be degraded by the degradation enzyme. In another example, the identifiers may be single-stranded and the identifier library may be combined with a single-strand specific endonuclease(s), such as the S1 nuclease, that selectively degrades identifiers that are not to be accessed. Identifiers to be accessed may be hybridized with a complementary set of identifiers to protect them from degradation by the single-strand specific endonuclease(s). The identifiers to be accessed may be separated from the degradation products by size selection, such as size selection chromatography (e.g., agarose gel electrophoresis). Alternatively, or in addition, identifiers that are not degraded may be selectively amplified (e.g., using PCR) such that the degradation products are not amplified. The non-degraded identifiers may be amplified using primers that hybridize to each end of the non-degraded identifiers and therefore not to each end of the degraded or cleaved identifiers.

FIG. 17B shows example methods for using polymerase chain reaction to perform 'OR' or 'AND' operations to access identifiers containing multiple components. In an example, if two forward primers bind distinct sets of identifiers on the left end, then an 'OR' amplification of the union of those sets of identifiers may be accomplished by using the two forward primers together in a multiplex PCR reaction with a reverse primer that binds all of the identifiers on the right end. In another example, if one forward primer binds a set of identifiers on the left end and one reverse primer binds a set of identifiers on the right end, then an 'AND' amplification of the intersection of those two sets of identifiers may be accomplished by using the forward primer and the reverse primer together as a primer pair in a PCR reaction.

FIG. 17C shows example methods for using affinity tags to perform 'OR' or 'AND' operations to access identifiers containing multiple components. In an example, if affinity probe 'P1' captures all identifiers with component 'C1' and another affinity probe 'P2' captures all identifiers with component 'C2', then the set of all identifiers with C1 or C2 can be captured by using P1 and P2 simultaneously (corresponding to an 'OR' operation). In another example with the same components and probes, the set of all identifiers with C1 and C2 can be captures by using P1 and P2 sequentially (corresponding to an 'AND' operation).

Methods for Reading Information Stored in Nucleic Acid Sequences

In another aspect, the present disclosure provides methods for reading information encoded in nucleic acid sequences. A method for reading information encoded in nucleic acid sequences may comprise (a) providing an identifier library, (b) identifying the identifiers present in the identifier library, (c) generating a string of symbols from the identifiers present in the identifier library, and (d) compiling information from the string of symbols. An identifier library may comprise a subset of a plurality of identifiers from a combinatorial space. Each individual identifier of the subset of identifiers may correspond to an individual symbol in a string of symbols. An identifier may comprise one or more components. A component may comprise a nucleic acid sequence.

Information may be written into one or more identifier libraries as described elsewhere herein. Identifiers may be constructed using any method described elsewhere herein. Stored data may be copied and accessed using any method described elsewhere herein.

The identifier may comprise information relating to a location of the encoded symbol, a value of the encoded symbol, or both the location and the value of the encoded symbol. An identifier may include information relating to a location of the encoded symbol and the presence or absence of the identifier in an identifier library may indicate the value of the symbol. The presence of an identifier in an identifier library may indicate a first symbol value (e.g., first bit value) in a binary string and the absence of an identifier in an identifier library may indicate a second symbol value (e.g., second bit value) in a binary string. In a binary system, basing a bit value on the presence or absence of an identifier in an identifier library may reduce the number of identifiers assembled and, therefore, reduce the write time. In an example, the presence of an identifier may indicate a bit value of '1' at the mapped location and the absence of an identifier may indicate a bit value of '0' at the mapped location.

Generating symbols (e.g., bit values) for a piece of information may include identifying the presence or absence of the identifier that the symbol (e.g., bit) may be mapped or encoded to. Determining the presence or absence of an identifier may include sequencing the present identifiers or using a hybridization array to detect the presence of an identifier. In an example, decoding and reading the encoded sequences may be performed using sequencing platforms. Examples of sequencing platforms are described in U.S. patent application Ser. No. 14/465,685 filed Aug. 21, 2014, U.S. patent application Ser. No. 13/886,234 filed May 2, 2013, and U.S. patent application Ser. No. 12/400,593 filed Mar. 9, 2009, each of which is entirely incorporated herein by reference.

In an example, decoding nucleic acid encoded data may be achieved by base-by-base sequencing of the nucleic acid strands, such as Illumina® Sequencing, or by utilizing a sequencing technique that indicates the presence or absence of specific nucleic acid sequences, such as fragmentation analysis by capillary electrophoresis. The sequencing may employ the use of reversible terminators. The sequencing may employ the use of natural or non-natural (e.g., engineered) nucleotides or nucleotide analogs. Alternatively or in addition to, decoding nucleic acid sequences may be performed using a variety of analytical techniques, including but not limited to, any methods that generate optical, electrochemical, or chemical signals. A variety of sequencing approaches may be used including, but not limited to, polymerase chain reaction (PCR), digital PCR, Sanger sequencing, high-throughput sequencing, sequencing-by-synthesis, single-molecule sequencing, sequencing-by-ligation, RNA-Seq (Illumina), Next generation sequencing, Digital Gene Expression (Helicos), Clonal Single MicroArray (Solexa), shotgun sequencing, Maxim-Gilbert sequencing, or massively-parallel sequencing.

Various read-out methods can be used to pull information from the encoded nucleic acid. In an example, microarray (or any sort of fluorescent hybridization), digital PCR, quantitative PCR (qPCR), and various sequencing platforms can be further used to read out the encoded sequences and by extension digitally encoded data.

An identifier library may further comprise supplemental nucleic acid sequences that provide metadata about the information, encrypt or mask the information, or that both provide metadata and mask the information. The supplemental nucleic acids may be identified simultaneously with identification of the identifiers. Alternatively, the supplemental nucleic acids may be identified prior to or after identifying the identifiers. In an example, the supplemental nucleic acids are not identified during reading of the encoded information. The supplemental nucleic acid sequences may be indistinguishable from the identifiers. An identifier index or a key may be used to differentiate the supplemental nucleic acid molecules from the identifiers.

The efficiency of encoding and decoding data may be increased by recoding input bit strings to enable the use of fewer nucleic acid molecules. For example, if an input string is received with a high occurrence of '111' substrings, which may map to three nucleic acid molecules (e.g., identifiers) with an encoding method, it may be recoded to a '000' substring which may map to a null set of nucleic acid molecules. The alternate input substring of '000' may also be recoded to '111'. This method of recoding may reduce the total amount of nucleic acid molecules used to encode the data because there may be a reduction in the number of '1's in the dataset. In this example, the total size of the dataset may be increased to accommodate a codebook that specifies the new mapping instructions. An alternative method for increasing encoding and decoding efficiency may be to recode the input string to reduce the variable length. For example, '111' may be recoded to '00' which may shrink the size of the dataset and reduce the number of '1's in the dataset.

The speed and efficiency of decoding nucleic acid encoded data may be controlled (e.g., increased) by specifically designing identifiers for ease of detection. For example, nucleic acid sequences (e.g., identifiers) that are designed for ease of detection may include nucleic acid sequences comprising a majority of nucleotides that are easier to call and detect based on their optical, electrochemical, chemical, or physical properties. Engineered nucleic acid sequences may be either single or double stranded. Engineered nucleic acid sequences may include synthetic or unnatural nucleotides that improve the detectable properties of the nucleic acid sequence. Engineered nucleic acid sequences may comprise all natural nucleotides, all synthetic or unnatural nucleotides, or a combination of natural, synthetic, and unnatural nucleotides. Synthetic nucleotides may include nucleotide analogues such as peptide nucleic acids, locked nucleic acids, glycol nucleic acids, and threose nucleic acids. Unnatural nucleotides may include dNaM, an artificial nucleoside containing a 3-methoxy-2-naphthly group, and d5SICS, an artificial nucleoside containing a 6-methylisoquinoline-1-thione-2-yl group. Engineered nucleic acid sequences may be designed for a single enhanced property, such as enhanced optical properties, or the designed nucleic acid sequences may be designed with multiple enhanced properties, such as enhanced optical and electrochemical properties or enhanced optical and chemical properties.

Engineered nucleic acid sequences may comprise reactive natural, synthetic, and unnatural nucleotides that do not improve the optical, electrochemical, chemical, or physical properties of the nucleic acid sequences. The reactive components of the nucleic acid sequences may enable the addition of a chemical moiety that confers improved properties to the nucleic acid sequence. Each nucleic acid sequence may include a single chemical moiety or may include multiple chemical moieties. Example chemical moieties may include, but are not limited to, fluorescent moieties, chemiluminescent moieties, acidic or basic moieties, hydrophobic or hydrophilic moieties, and moieties that alter oxidation state or reactivity of the nucleic acid sequence.

A sequencing platform may be designed specifically for decoding and reading information encoded into nucleic acid sequences. The sequencing platform may be dedicated to sequencing single or double stranded nucleic acid molecules. The sequencing platform may decode nucleic acid encoded data by reading individual bases (e.g., base-by-base sequencing) or by detecting the presence or absence of an entire nucleic acid sequence (e.g., component) incorporated within the nucleic acid molecule (e.g., identifier). The sequencing platform may include the use of promiscuous reagents, increased read lengths, and the detection of specific nucleic acid sequences by the addition of detectable chemical moieties. The use of more promiscuous reagents during sequencing may increase reading efficiency by enabling faster base calling which in turn may decrease the sequencing time. The use of increased read lengths may enable longer sequences of encoded nucleic acids to be decoded per read. The addition of detectable chemical moiety tags may enable the detection of the presence or absence of a nucleic acid sequence by the presence or absence of a chemical moiety. For example, each nucleic acid sequence encoding a bit of information may be tagged with a chemical moiety that generates a unique optical, electrochemical, or chemical signal. The presence or absence of that unique optical, electrochemical, or chemical signal may indicate a '0' or a '1' bit value. The nucleic acid sequence may comprise a single chemical moiety or multiple chemical moieties. The chemical moiety may be added to the nucleic acid sequence prior to use of the nucleic acid sequence to encode data. Alternatively or in addition to, the chemical moiety may be added to the nucleic acid sequence after encoding the data, but prior to decoding the data. The chemical moiety tag may be added directly to the nucleic acid sequence or the nucleic acid sequence may comprise a synthetic or unnatural nucleotide anchor and the chemical moiety tag may be added to that anchor.

Unique codes may be applied to minimize or detect encoding and decoding errors. Encoding and decoding errors may occur from false negatives (e.g., a nucleic acid molecule or identifier not included in a random sampling). An example of an error detecting code may be a checksum sequence that counts the number of identifiers in a contiguous set of possible identifiers that is included in the identifier library. While reading the identifier library, the checksum may indicate how many identifiers from that contiguous set of identifiers to expect to retrieve, and identifiers can continue to be sampled for reading until the expected number is met. In some embodiments, a checksum sequence may be included for every contiguous set of R identifiers where R can be equal in size or greater than 1, 2, 5, 10, 50, 100, 200, 500, or 1000 or less than 1000, 500, 200, 100, 50, 10, 5, or 2. The smaller the value of R, the better the error detection. In some embodiments, the checksums may be supplemental nucleic acid sequences. For example, a set comprising seven nucleic acid sequences (e.g., components) may be divided into two groups, nucleic acid sequences for constructing identifiers with a product scheme (components X1-X3 in layer X and Y1-Y3 in layer Y), and nucleic acid sequences for the supplemental checksums (X4-X7 and Y4-Y7). The checksum sequences X4-X7 may indicate whether zero, one, two, or three sequences of layer X are assembled with each member of layer Y. Alternatively, the checksum sequences Y4-Y7 may indicate whether zero, one, two, or three sequences of layer Y are assembled with each member of layer X. In this example, an original identifier library with identifiers {X1Y1, X1Y3, X2Y1, X2Y2, X2Y3} may be supplemented to include checksums to become the following pool: {X1Y1, X1Y3, X2Y1, X2Y2, X2Y3, X1Y6, X2Y7, X3Y4, X6Y1, X5Y2, X6Y3}. The checksum sequences may also be used for error correction. For example, absence of X1Y1 from the above dataset and the presence of X1Y6 and X6Y1 may enable inference that the X1Y1 nucleic acid molecule is missing from the dataset. The checksum sequences may indicate whether identifiers are missing from a sampling of the identifier library or an accessed portion of the identifier library. In the case of a missing checksum sequence, access methods such as PCR or affinity tagged probe hybridization may amplify and/or isolate it. In some embodiments, the checksums may not be supplemental nucleic acid sequences. They checksums may be coded directly into the information such that they are represented by identifiers.

Noise in data encoding and decoding may be reduced by constructing identifiers palindromically, for example, by using palindromic pairs of components rather than single components in the product scheme. Then the pairs of components from different layers may be assembled to one another in a palindromic manner (e.g., YXY instead of XY for components X and Y). This palindromic method may be expanded to larger numbers of layers (e.g., ZYXYZ instead of XYZ) and may enable detection of erroneous cross reactions between identifiers.

Adding supplemental nucleic acid sequences in excess (e.g., vast excess) to the identifiers may prevent sequencing from recovering the encoded identifiers. Prior to decoding the information, the identifiers may be enriched from the supplemental nucleic acid sequences. For example, the identifiers may be enriched by a nucleic acid amplification reaction using primers specific to the identifier ends. Alternatively, or in addition to, the information may be decoded without enriching the sample pool by sequencing (e.g., sequencing by synthesis) using a specific primer. In both decoding methods, it may be difficult to enrich or decode the information without having a decoding key or knowing something about the composition of the identifiers. Alternative access methods may also be employed such as using affinity tag based probes.

Systems for Encoding Binary Sequence Data

A system for encoding digital information into nucleic acids (e.g., DNA) can comprise systems, methods and devices for converting files and data (e.g., raw data, compressed zip files, integer data, and other forms of data) into bytes and encoding the bytes into segments or sequences of nucleic acids, typically DNA, or combinations thereof.

In an aspect, the present disclosure provides systems for encoding binary sequence data using nucleic acids. A system for encoding binary sequence data using nucleic acids may comprise a device and one or more computer processors. The device may be configured to construct an identifier library. The one or more computer processors may be individually or collectively programmed to (i) translate the information into a sting of symbols, (ii) map the string of symbols to the plurality of identifiers, and (iii) construct an identifier library comprising at least a subset of a plurality of identifiers. An individual identifier of the plurality of identifiers may correspond to an individual symbol of the string of symbols. An individual identifier of the plurality of identifiers may comprise one or more components. An individual component of the one or more components may comprise a nucleic acid sequence.

In another aspect, the present disclosure provides systems for reading binary sequence data using nucleic acids. A system for reading binary sequence data using nucleic acids may comprise a database and one or more computer processors. The database may store an identifier library encoding the information. The one or more computer processors may be individually or collectively programmed to (i) identify the identifiers in the identifier library, (ii) generate a plurality of symbols from identifiers identified in (i), and (iii) compile the information from the plurality of symbols. The identifier library may comprise a subset of a plurality of identifiers. Each individual identifier of the plurality of identifiers may correspond to an individual symbol in a string of symbols. An identifier may comprise one or more components. A component may comprise a nucleic acid sequence.

Non-limiting embodiments of methods for using the system to encode digital data can comprise steps for receiving digital information in the form of byte streams. Parsing the byte streams into individual bytes, mapping the location of a bit within the byte using a nucleic acid index (or identifier rank), and encoding sequences corresponding to either bit values of 1 or bit values of 0 into identifiers. Steps for retrieving digital data can comprise sequencing a nucleic acid sample or nucleic acid pool comprising sequences of nucleic acid (e.g., identifiers) that map to one or more bits, referencing an identifier rank to confirm if the identifier is present in the nucleic acid pool and decoding the location and bit-value information for each sequence into a byte comprising a sequence of digital information.

Systems for encoding, writing, copying, accessing, reading, and decoding information encoded and written into nucleic acid molecules may be a single integrated unit or may be multiple units configured to execute one or more of the aforementioned operations. A system for encoding and writing information into nucleic acid molecules (e.g., identifiers) may include a device and one or more computer processors. The one or more computer processors may be programmed to parse the information into strings of symbols (e.g., strings of bits). The computer processor may generate an identifier rank. The computer processor may categorize the symbols into two or more categories. One category may include symbols to be represented by a presence of the corresponding identifier in the identifier library and the other category may include symbols to be represented by an absence of the corresponding identifiers in the identifier library. The computer processor may direct the device to assemble the identifiers corresponding to symbols to be represented to the presence of an identifier in the identifier library.

The device may comprise a plurality regions, sections, or partitions. The reagents and components to assemble the identifiers may be stored in one or more regions, sections, or partitions of the device. Layers may be stored in separate regions of section of the device. A layer may comprise one or more unique components. The component in one layer may be unique from the components in another layer. The regions or sections may comprise vessels and the partitions may comprise wells. Each layer may be stored in a separate vessel or partition. Each reagent or nucleic acid sequence may be stored in a separate vessel or partition. Alternatively, or in addition to, reagents may be combined to form a master mix for identifier construction. The device may transfer reagents, components, and templates from one section of the device to be combined in another section. The device may provide the conditions for completing the assembly reaction. For example, the device may provide heating, agitation, and detection of reaction progress. The constructed identifiers may be directed to undergo one or more subsequent reactions to add barcodes, common sequences, variable sequences, or tags to one or more ends of the identifiers. The identifiers may then be directed to a region or partition to generate an identifier library. One or more identifier libraries may be stored in each region, section, or individual partition of the device. The device may transfer fluid (e.g., reagents, components, templates) using pressure, vacuum, or suction.

The identifier libraries may be stored in the device or may be moved to a separate database. The database may comprise one or more identifier libraries. The database may provide conditions for long term storage of the identifier libraries (e.g., conditions to reduce degradation of identifiers). The identifier libraries may be stored in a powder, liquid, or solid form. The database may provide Ultra-Violet light protection, reduced temperature (e.g., refrigeration or freezing), and protection from degrading chemicals and enzymes. Prior to being transferred to a database, the identifier libraries may be lyophilized or frozen. The identifier libraries may include ethylenediaminetetraacetic acid (EDTA) to inactivate nucleases and/or a buffer to maintain the stability of the nucleic acid molecules.

The database may be coupled to, include, or be separate from a device that writes the information into identifiers, copies the information, accesses the information, or reads the information. A portion of an identifier library may be removed from the database prior to copying, accessing or reading. The device that copies the information from the database may be the same or a different device from that which writes the information. The device that copies the information may extract an aliquot of an identifier library from the device and combine that aliquot with the reagents and constituents to amplify a portion of or the entire identifier library. The device may control the temperature, pressure, and agitation of the amplification reaction. The device may comprise partitions and one or more amplification reaction may occur in the partition comprising the identifier library. The device may copy more than one pool of identifiers at a time.

The copied identifiers may be transferred from the copy device to an accessing device. The accessing device may be the same device as the copy device. The access device may comprise separate regions, sections, or partitions. The access device may have one or more columns, bead reservoirs, or magnetic regions for separating identifiers bound to affinity tags. Alternatively, or in addition to, the access device may have one or more size selection units. A size selection unit may include agarose gel electrophoresis or any other method for size selecting nucleic acid molecules. Copying and extraction may be performed in the same region of a device or in different regions of a device.

The accessed data may be read in the same device or the accessed data may be transferred to another device. The reading device may comprise a detection unit to detect and identify the identifiers. The detection unit may be part of a sequencer, hybridization array, or other unit for identifying the presence or absence of an identifier. A sequencing platform may be designed specifically for decoding and reading information encoded into nucleic acid sequences. The sequencing platform may be dedicated to sequencing single or double stranded nucleic acid molecules. The sequencing platform may decode nucleic acid encoded data by reading individual bases (e.g., base-by-base sequencing) or by detecting the presence or absence of an entire nucleic acid sequence (e.g., component) incorporated within the nucleic acid molecule (e.g., identifier). Alternatively, the sequencing platform may be a system such as Illumina® Sequencing or fragmentation analysis by capillary electrophoresis. Alternatively or in addition to, decoding nucleic acid sequences may be performed using a variety of analytical techniques implemented by the device, including but not limited to, any methods that generate optical, electrochemical, or chemical signals.

Information storage in nucleic acid molecules may have various applications including, but not limited to, long term information storage, sensitive information storage, and storage of medical information. In an example, a person's medical information (e.g., medical history and records) may be stored in nucleic acid molecules and carried on his or her person. The information may be stored external to the body (e.g., in a wearable device) or internal to the body (e.g., in a subcutaneous capsule). When a patient is brought into a medical office or hospital, a sample may be taken from the device or capsule and the information may be decoded with the use of a nucleic acid sequencer. Personal storage of medical records in nucleic acid molecules may provide an alternative to computer and cloud based storage systems. Personal storage of medical records in nucleic acid molecules may reduce the instance or prevalence of medical records being hacked. Nucleic acid molecules used for capsule-based storage of medical records may be derived from human genomic sequences. The use of human genomic sequences may decrease the immunogenicity of the nucleic acid sequences in the event of capsule failure and leakage.

Computer Systems

Figure 19:
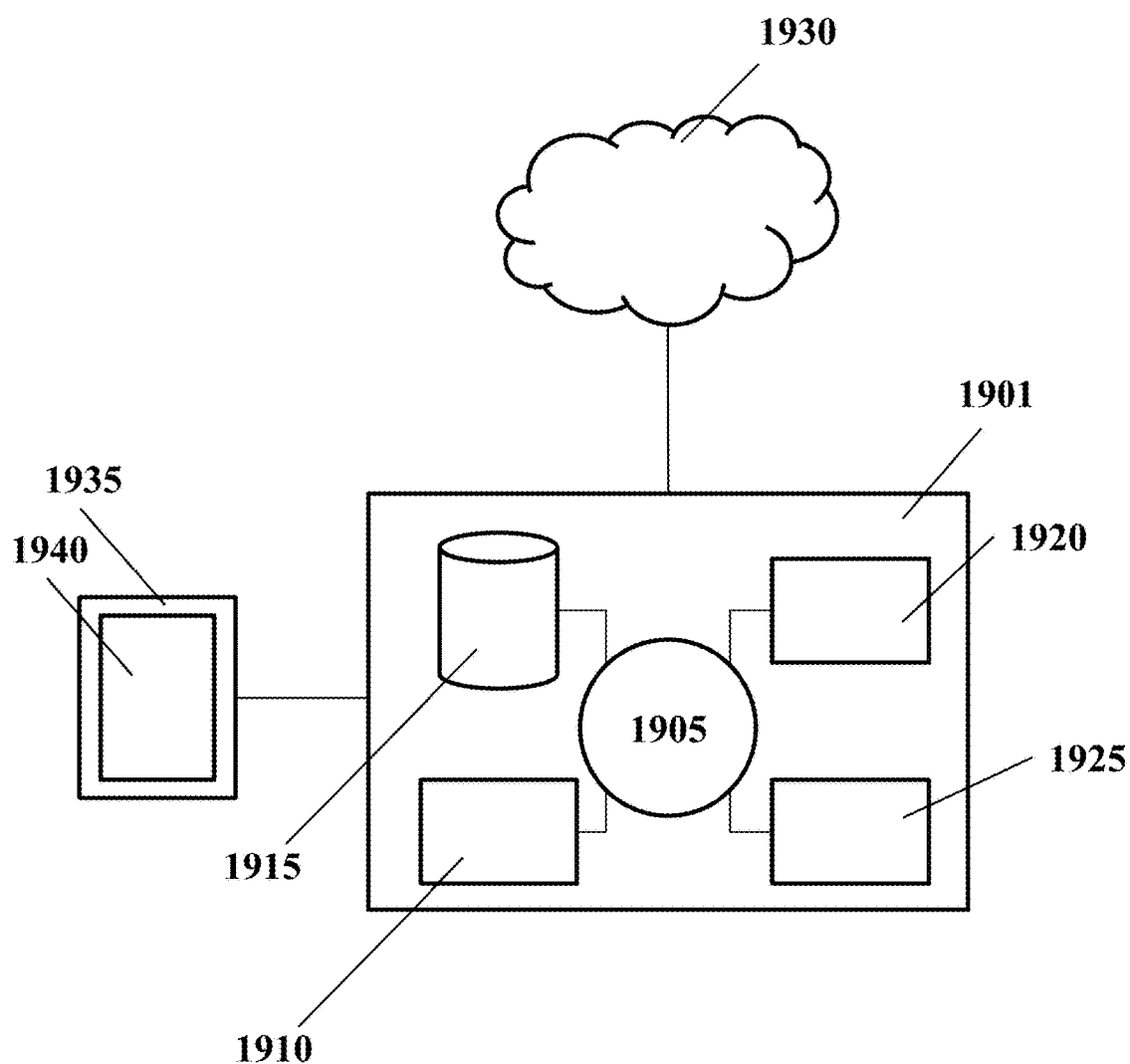
FIG. 19 shows a computer system that is programmed or otherwise configured to implement methods provided herein.

The present disclosure provides computer systems that are programmed to implement methods of the disclosure. FIG. 19 shows a computer system 1901 that is programmed or otherwise configured to encode digital information into nucleic acid sequences and/or read (e.g., decode) information derived from nucleic acid sequences. The computer system 1901 can regulate various aspects of the encoding and decoding procedures of the present disclosure, such as, for example, the bit-values and bit location information for a given bit or byte from an encoded bitstream or byte stream.

The computer system 1901 includes a central processing unit (CPU, also "processor" and "computer processor" herein) 1905, which can be a single core or multi core processor, or a plurality of processors for parallel processing. The computer system 1901 also includes memory or memory location 1910 (e.g., random-access memory, read-only memory, flash memory), electronic storage unit 1915 (e.g., hard disk), communication interface 1920 (e.g., network adapter) for communicating with one or more other systems, and peripheral devices 1925, such as cache, other memory, data storage and/or electronic display adapters. The memory 1910, storage unit 1915, interface 1920 and peripheral devices 1925 are in communication with the CPU 1905 through a communication bus (solid lines), such as a motherboard. The storage unit 1915 can be a data storage unit (or data repository) for storing data. The computer system 1901 can be operatively coupled to a computer network ("network") 1930 with the aid of the communication interface 1920. The network 1930 can be the Internet, an internet and/or extranet, or an intranet and/or extranet that is in communication with the Internet. The network 1930 in some cases is a telecommunication and/or data network. The network 1930 can include one or more computer servers, which can enable distributed computing, such as cloud computing. The network 1930, in some cases with the aid of the computer system 1901, can implement a peer-to-peer network, which may enable devices coupled to the computer system 1901 to behave as a client or a server.

The CPU 1905 can execute a sequence of machine-readable instructions, which can be embodied in a program or software. The instructions may be stored in a memory location, such as the memory 1910. The instructions can be directed to the CPU 1905, which can subsequently program or otherwise configure the CPU 1905 to implement methods of the present disclosure. Examples of operations performed by the CPU 1905 can include fetch, decode, execute, and writeback.

The CPU 1905 can be part of a circuit, such as an integrated circuit. One or more other components of the system 1901 can be included in the circuit. In some cases, the circuit is an application specific integrated circuit (ASIC).

The storage unit 1915 can store files, such as drivers, libraries and saved programs. The storage unit 1915 can store user data, e.g., user preferences and user programs. The computer system 1901 in some cases can include one or more additional data storage units that are external to the computer system 1901, such as located on a remote server that is in communication with the computer system 1901 through an intranet or the Internet.

The computer system 1901 can communicate with one or more remote computer systems through the network 1930. For instance, the computer system 1901 can communicate with a remote computer system of a user or other devices and or machinery that may be used by the user in the course of analyzing data encoded or decoded in a sequence of nucleic acids (e.g., a sequencer or other system for chemically determining the order of nitrogenous bases in a nucleic acid sequence). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1901 via the network 1930.

Methods as described herein can be implemented by way of machine (e.g., computer processor) executable code stored on an electronic storage location of the computer system 1901, such as, for example, on the memory 1910 or electronic storage unit 1915. The machine executable or machine readable code can be provided in the form of software. During use, the code can be executed by the processor 1905. In some cases, the code can be retrieved from the storage unit 1915 and stored on the memory 1910 for ready access by the processor 1905. In some situations, the electronic storage unit 1915 can be precluded, and machine-executable instructions are stored on memory 1910.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1901 can include or be in communication with an electronic display 1935 that comprises a user interface (UI) 1940 for providing, for example, sequence output data including chromatographs, sequences as well as bits, bytes, or bit streams encoded by or read by a machine or computer system that is encoding or decoding nucleic acids, raw data, files and compressed or decompressed zip files to be encoded or decoded into DNA stored data. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1905. The algorithm can, for example, be used with a DNA index and raw data or zip file compressed or decompressed data, to determine a customized method for coding digital information from the raw data or zip file compressed data, prior to encoding the digital information.

EXAMPLES

Example 1: Encoding, Writing and Reading a Single Poem in DNA Molecules

Data to be encoded is a textfile containing a poem. The data is encoded manually with pipettes to mix together DNA components from two layers of 96 components to construct identifiers using the product scheme implemented with overlap extension PCR. The first layer, X, comprises 96 total DNA components. The second layer, Y, also comprises 96 total components. Prior to writing the DNA, the data is mapped to binary and then recoded to a uniform weight format where every contiguous (adjacent disjoint) string of 61 bits of the original data is translated to a 96 bit string with exactly 17 bit-values of 1. This uniform weight format may have natural error checking qualities. The data is then hashed into a 96 by 96 table to form a reference map.

Figure 18A:
FIGS. 18A and 18B show examples of encoding, writing, and reading data encoded in nucleic acid molecules.

The middle panel of FIG. 18A shows the two-dimensional reference map of a 96 by 96 table encoding the poem into a plurality of identifiers. Dark points correspond to a '1' bit-value and white points corresponded to a '0' bit-value. The data is encoded into identifiers using two layers of 96 components. Each X value and Y value of the table is assigned a component and the X and Y components are assembled into an identifier using overlap extension PCR for each (X,Y) coordinate with a '1' value. The data was read back (e.g., decoded) by sequencing the identifier library to determine the presence or absence of each possible (X,Y) assembly.

The right panel of figure FIG. 18A shows a two-dimensional heat map of the abundances of sequences present in the identifier library as determined by sequencing. Each pixel represents a molecule comprising the corresponding X and Y components, and the greyscale intensity at that pixel represents the relative abundance of that molecule compared to other molecules. Identifiers are taken as the top 17 most abundant (X, Y) assemblies in each row (as the uniform weight encoding guarantees that each contiguous string of 96 bits may have exactly 17 '1' values, and hence 17 corresponding identifiers).

Example 2: Encoding a 62824 Bit Textfile

Data to be encoded is a textfile of three poems totaling 62824 bits. The data is encoded using a Labcyte Echo® Liquid Handler to mix together DNA components from two layers of 384 components to construct identifiers using the product scheme implemented with overlap extension PCR. The first layer, X, comprises 384 total DNA components. The second layer, Y, also comprises 384 total components. Prior to writing the DNA, the data is mapped to binary and then recoded to decrease the weight (number of bit-values of '1') and include checksums. The checksums are established so that there is an identifier that corresponds to a checksum for every contiguous string of 192 bits of data. The re-coded data has a weight of approximately 10,100, which corresponds to the number of identifiers to be constructed. The data may then be hashed into a 384 by 384 table to form a reference map.

Figure 18B:
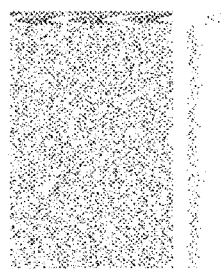

The middle panel of FIG. 18B shows a two-dimensional reference map of a 384 by 384 table encoding the textfile into a plurality of identifiers. Each coordinate (X,Y) corresponds to the bit of data at position X+(Y−1)*192. Black points correspond to a bit value of '1' and white points correspond to a bit value of '0'. The black points on the right side of the figure are the checksums and the pattern of black points on the top of the figure is the codebook (e.g., dictionary for de-coding the data). Each X value and Y value of the table may be assigned a component and the X and Y components are assembled into an identifier using overlap extension PCR for each (X, Y) coordinate with a '1' value. The data was read back (e.g., decoded) by sequencing the identifier library to determine the presence or absence of each possible (X, Y) assembly.

The right panel of FIG. 18B shows a two-dimensional heat map of the abundances of sequences present in the identifier library as determined by sequencing. Each pixel represents a molecule comprising the corresponding X and Y components, and the greyscale intensity at that pixel represents the relative abundance of that molecule compared to other molecules. Identifiers are taken as the top S most abundant (X, Y) assemblies in each row, where S for each row may be the checksum value.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for writing information into nucleic acid sequence(s), comprising:
   (a) constructing a plurality of components, wherein each individual component of said plurality of components comprises a nucleic acid sequence;
   (b) repeatedly ligating together two or more components of said plurality of components, thereby generating a plurality of identifiers, wherein each identifier of said plurality of identifiers comprises two or more components, wherein an individual identifier of said plurality of identifiers corresponds to an individual symbol, which symbol corresponds to at least a portion of said information; and
   (c) selectively capturing or amplifying an identifier library comprising at least a subset of said plurality of identifiers, wherein said subset of said plurality of identifiers comprises a barcode, wherein each individual identifier in said identifier library comprises a unique barcode.

2. The method of claim 1, wherein said individual symbol is one of one or more possible symbol values.

3. The method of claim 1, wherein said individual symbol is one of two possible symbol values.

4. The method of claim 1, wherein one symbol value is represented by the absence of a distinct identifier in the identifier library.

5. The method of claim 3, wherein said two possible symbol values are a bit-value of 0 and 1, wherein said individual symbol with said bit-value of 0 is represented by an absence of a distinct identifier in said identifier library, wherein said individual symbol with said bit-value of 1 is represented by a presence of said distinct identifier in said identifier library, or vice versa.

6. The method of claim 1, wherein generating said individual identifier in said identifier library comprises ligating said two or more components from two or more layers and wherein each layer of said two or more layers comprises a distinct set of components.

7. The method of claim 6, wherein said individual identifier from said identifier library comprises one component from each layer of said two or more layers.

8. The method of claim 7, wherein said two or more components are assembled in a fixed order.

9. The method of claim 7, wherein said two or more components are assembled in any order.

10. The method of claim 7, wherein said two or more components are assembled with one or more partitioning components disposed between two components from different layers of said two or more layers.

11. The method of claim 6, wherein said individual identifier comprises one component from each layer of a subset of said two or more layers.

12. The method of claim 6, wherein said individual identifier comprises at least one component from each of said two or more layers.

13. The method of claim 1, wherein said two or more components are ligated using sticky end ligation, ligase cycling reaction, or template directed ligation.

14. The method of claim 1, wherein said nucleic acid sequences store metadata of said information or conceals said information.

15. The method of claim 14, wherein said metadata comprises secondary information corresponding to a source of said information, an intended recipient of said information, an original format of said information, instrumentation and methods used to encode said information, a date and a time of writing said information into said identifier library, modifications made to said information, and/or a reference to other information.

16. The method of claim 1, wherein two or more identifier libraries are combined.

17. The method of claim 1, wherein said plurality of identifiers is selected for read, write, access, copy, and deletion operations.

18. The method of claim 1, further comprising error checking or error correction of said individual symbol.

19. The method of claim 18, wherein said error checking or error correction includes checksums.

20. The method of claim 1, wherein said information is copied by creating one or more copies of said identifier library.

21. The method of claim 1, wherein said information is queried by isolating a targeted subset of identifiers from said identifier library.

22. The method of claim 1, wherein said information is read by determining the nucleic acid sequences of a plurality of identifiers from said identifier library.

23. The method of claim 1, wherein said barcode stores metadata of said information or conceals said information.

24. A method for writing information into nucleic acid sequence(s), comprising:
(a) providing a parent identifier comprising a plurality of components, wherein each component of said plurality of components comprises a nucleic acid sequence;
(b) contacting said parent identifier with a reagent comprising at least one recombinase or nuclease to delete, replace, or insert at least one component, or a portion thereof, in said parent identifier, thereby generating a plurality of identifiers having at least one identifier that is different from said parent identifier, wherein an individual identifier of said plurality of identifiers corresponds to an individual symbol, which symbol corresponds to at least a portion of said information; and
(c) selectively capturing or amplifying an identifier library comprising at least a subset of said plurality of identifiers, wherein said subset of said plurality of identifiers comprises a barcode, wherein each individual identifier in said identifier library comprises a unique barcode.

25. The method of claim 24, wherein said plurality of components of said parent identifier is flanked by nuclease-specific target sites, recombinase recognition sites, or distinct spacer sequences.

26. The method of claim 24, wherein said nuclease is selected from the group consisting of Clustered Regularly Interspaced Short Palindromic Repeats (CRISPR)-Cas9, Transcription activator-like effector nucleases (TALENs), Zinc Finger Nucleases, and any combination thereof.

* * * * *